US006483010B1

(12) United States Patent
Kossmann et al.

(10) Patent No.: US 6,483,010 B1
(45) Date of Patent: Nov. 19, 2002

(54) DNA MOLECULES ENCODING ENZYMES INVOLVED IN STARCH SYNTHESIS, VECTORS, BACTERIA, TRANSGENIC PLANT CELLS AND PLANTS CONTAINING THESE MOLECULES

(76) Inventors: Jens Kossmann, Golmer Eichten 9, Golm (DE), D-14476; Franziska Springer, Muhlenstr. 1, Berlin (DE), D-14167; Gernot J. Abel, Pichlgut Au 36, Post Loibichl (AT), 5311

( * ) Notice: Subject to any disclaimer, the term of this patent is extended or adjusted under 35 U.S.C. 154(b) by 0 days.

(21) Appl. No.: 09/606,304

(22) Filed: Jun. 28, 2000

Related U.S. Application Data

(62) Division of application No. 08/836,567, filed as application No. PCT/EP95/04415 on Nov. 9, 1995, now Pat. No. 6,130,367.

(30) Foreign Application Priority Data

Nov. 10, 1994 (DE) .......................................... 44 41 408

(51) Int. Cl.[7] .................... C12N 15/29; C12N 15/82; C12N 5/04; A01H 5/00; C12P 19/04
(52) U.S. Cl. ..................... 800/284; 800/278; 800/286; 800/317.2; 435/417; 435/419; 536/23.6; 536/24.5
(58) Field of Search .................. 800/278, 284, 800/286, 317.2; 435/419, 417; 536/23.6, 24.5

(56) References Cited

U.S. PATENT DOCUMENTS

| 5,300,145 A | 4/1994 | Fergason et al. ............ 106/213 |
| 5,824,790 A | 10/1998 | Keeling et al. ............ 536/23.6 |

FOREIGN PATENT DOCUMENTS

| CA | 2061443 | 8/1993 |
| EP | 0 521 621 A2 | 1/1993 |
| JP | 6-70779 | 3/1994 |
| WO | WO 92/11376 | 7/1992 |
| WO | WO 92/14827 | 9/1992 |
| WO | WO 94/09144 | 4/1994 |
| WO | WO 94/11520 | 5/1994 |

OTHER PUBLICATIONS

T. Baba et al., "Identification, cDNA Cloning, and Gene Expression of Soluble Starch Synthesis in Rick (*Oryza sativa* L.) Immature Seeds", *Plant Physiol*, 103, pp. 565–573 (1993).

I. Dry et al., "Characterization of cDNAs Encoding Two Isoforms of Granule–Bound Starch Synthase Which Show Differential Expression in Developing Storage Organs of Pea and Potato", *The Plant Journal*, 2(2), pp. 193–202 (1992).

S.N.I.M. Salehuzzaman, et al., "Isolation and Characterization of a cDNA Encloding Granule–Bound Starch Synthase In Cassava (Manihot Esculenya Crantz) and its Antisense Expression in Potato", *Plant Molecular Biology*, 23, pp. 947–962 (1993).

Ainsworth et al., "Expression, Organisation and Structure of the Genes Encoding the Waxy Protein (Granule–Bound Starch Synthase) in Wheat," *Pl. Molec. Biol.*, 22:67–82 (1993).

Clark et al., "Nucleotide Sequence of a Wheat (*Triticum aestivum* L.) cDNA Clone Encoding the waxy Protein," Pl. Molec. Biol., 16, pp. 1099–1101 (1991).

Edwards et al., "Biochemical and Molecular Characterization of a Novel Starch Synthase form Potato Tubers,"*Plant J.*, 8:283–294 (1995).

Klösgen et al., "Molecular analysis of the *waxy* locus of Zea mays," *Molec. Gen. Genet.*, 203:237–244 (1986).

Kossmann et al., (1995) "Transgenic plants as a tool to understand starch biosynthesis," *Progress Biotechnol.*, 10, pp. 271–278.

Mu et al., "Association of a 76 kDa Polypeptide with Soluble Starch Synthase 1 Activity in Maize (cvB73) Endosperm," *Plant J.*, 6:151–159 (1994).

Müller–Röber et al., "Approaches to Influence Starch Quantity and Starch Quality in Transgenic Plants," Plant, Cell and Environ., 17:601–613 (1994).

Nakatani et al., "Relationship between Starch Content and Activity of Starch Synthase and ADP–glucose Pyrophosphorylase in Tuberous Root of Sweet Potato," *Japanese J. Crop Sci.*, 61:463–468 (1992).

Rahman et al., "The Major Proteins of Wheat Endosperm Starch Granules," *Aust. J. Plant Physiol.*, 22:792–803 (1995).

Visser et al., "Inhibition of the Expression of the Gene for Granule–bound Starch Synthase in Potato by Antisense Constructs," *Molec. Gen. Genet.*, 225:289–296 (1991).

*Primary Examiner*—David T. Fox
(74) *Attorney, Agent, or Firm*—Fish & Neave; James F. Haley, Jr.; Grant Kalinowski

(57) ABSTRACT

The present invention relates to DNA molecules encoding enzymes which are involved in the starch synthesis of plants. These enzymes represent two different isotypes of the soluble starch synthase as well as a starch granule-bound starch synthase. This invention furthermore relates to vectors, bacteria, as well as to plant cells transformed with the DNA molecules described and to plants regenerated from them. Furthermore, the invention relates to starch that can be isolated from plants having an increased or reduced activity of the proteins described.

8 Claims, 5 Drawing Sheets

```
a  ..........  ............  ......MQVL  HVCSEMFPLL  KTGGLADVIG
b  PKQSRKAHRG  SRRCLSVVVS    ATGS.GMNLV  FVGAEMAPWS  KTGGLGDVLG
c  PKQSRKPHRF  DRRCLSMVVR    ATGSGGMNLV  FVGAEMAPWS  KTGGLGDVLG
d  PRHQQQARRG  G.RFPSLVVC    A.SA.GMNVV  FVGAEMAPWS  KTGGLGDVLG
e  PKQQRSVQRG  SRRFPSVVVY    ATGA.GMNVV  FVGAEMAPWS  KTGGLGDVLG
f  KKV.SATGNG  RPA..AKIIC    GH...GMNLI  FVGAEVGPWS  KTGGLGDVLG
g  PKMASRTETK  RPGCSATIVC    GK...GMNLI  FVGTEVGPWS  KTGGLGDVLG
h  SKEVANEAEN  FESGGEKPPP    LAGTNVMNII  LVSAECAPWS  KTGGLGDVAG
i  SAEANEETED  PVNIDEKPPP    LAGTNVMNII  LVASECAPWS  KTGGLGDVAG
k  DKTIFVASEQ  ESEIMDVKEQ    AQAKVTRSVV  FVTGEASPYA  KSGGLGDVCG
l  DGGIFDNKSG  MDYHIPVFGG    VAKEPPMHIV  HIAVEMAPIA  KVGGLGDVVT
                                                    (I)

a  SHRIMGGADV  ILVPSRFEPC  GLTQLYGSKY  GTLPLVRRTG  GLADTVSDCS
b  AHQMMAGADL  LAVTSRFEPC  GLIQLQGMRY  GTPCVCASTG  GLVDTIVEGK
c  AHQMMAGADV  LAVTSRFEPC  GLIQLQGMRY  GTPCACASTG  GLVDTIVEGK
d  AHHIMAGADV  LAVTSRFEPC  GLIQLQGMRY  GTPCACASTG  GLVDTIIEGK
e  AHLIMAGADV  LAVPSRFEPC  GLIQLQGMRY  GTPCACASTG  GLVDTVIEGK
f  AHMITAGADF  MLVPSRFEPC  GLIQLHAMRY  GTVPIVASTG  GLVDTVKEGY
g  AHMITAGADF  MLVPSRFEPC  GLIQLHAMRY  GTVPICASTG  GLVDTVKEGY
h  AHRITAGSDI  LLMPSRFEPC  GLNQLYAMSY  GTVPVHGVG   GLRDTVQPFN
i  SHRITAGADI  LLMPSRFEAL  RLNQLYAMKY  GTIPVVHAVG  GLRDTVQPFD
k  SHRITAGCDI  LLMPSRFEPC  GLNQLYAMQY  GTVPVVHGTG  GLRDTVENFN
l  SHLIYAGADF  ILVPSIFEPC  GLTQLTAMRY  GSIPVVRKTG  GLYDTVFDVD
m  SHRITAGCDI  LLMPSRFEPC  GLNQLYAMRY  GTIPIVHSTG  GLRDTVKDFN (II)                    (III)
```

FIG. 7

DNA MOLECULES ENCODING ENZYMES INVOLVED IN STARCH SYNTHESIS, VECTORS, BACTERIA, TRANSGENIC PLANT CELLS AND PLANTS CONTAINING THESE MOLECULES

This application is a DIV of U.S. application Ser. No. 08/836,567, filed Jul. 24, 1997, now U.S. Pat. No. 6,130,367, which is a 371 of PCT/EP95/04415, filed Nov. 9, 1995.

FIELD OF THE INVENTION

The present invention relates to DNA molecules encoding enzymes which are involved in the starch synthesis of plants. These, enzymes represent two different isotypes of the soluble starch synthase as well as a starch granule-bound starch synthase. This invention furthermore relates to vectors, bacteria, as well as to plant cells transformed with the DNA molecules described and to plants regenerated from them.

Also, processes for the production of transgenic plants are described which, due to the introduction of DNA molecules encoding soluble or starch granule-bound starch synthases, synthesize a starch which is modified as regards its properties.

BACKGROUND OF THE INVENTION

With respect to its increasing significance which has recently been ascribed to vegetal substances as regenerative sources of raw materials, one of the objects of biotechnological research is to try to adapt vegetal raw materials to the demands of the processing industry. In order to enable the use of modified regenerative raw materials in as many areas as possible, it is furthermore important to obtain a large variety of substances. Apart from oils, fats and proteins, polysaccharides constitute the essential regenerative raw materials derived from plants. Apart from cellulose, starch maintains an important position among the polysaccharides, being one of the most significant storage substances in higher plants. Besides maize, rice and wheat, potato plays an important role as starch producer.

The polysaccharide starch is a polymer made up of chemically homogeneous basic components, namely the glucose molecules. However, it constitutes a highly complex mixture from various types of molecules which differ from each other in their degree of polymerization and in the degree of branching of the glucose chains. Therefore, starch is not a homogeneous raw material. One differentiates particularly between amylose-starch, a basically non-branched polymer made up of α-1,4-glycosidically branched glucose-molecules, and amylopectin-starch which in turn is a complex mixture of various branched glucose chains. The branching results from additional α-1,6-glycosidic interlinkings. In plants which are typically used for starch production, such as, e.g., maize or potato, the synthesized starch consists of about 25% of amylose starch and of about 75% of amylopectin starch.

In order to enable as wide a use of starch as possible, it seems to be desirable that plants be provided which are capable of synthesizing modified starch which is particularly suitable for various uses. A possibility of providing such plants is—apart from breeding—in the specific genetic modification of the starch metabolism of starch-producing plants by means of recombinant DNA techniques. However, a prerequisite therefor is to identify and to characterize the enzymes involved in the starch synthesis and/or the starch modification as well as to isolate the respective DNA molecules encoding these enzymes.

The biochemical pathways which lead to the production of starch are basically known. The starch synthesis in plant cells takes place in the plastids. In photosynthetically active tissues these are the chloroplasts, in photosynthetically inactive, starch-storing tissues the amyloplasts.

The most important enzymes involved in starch synthesis are starch synthases as well as branching enzymes. In the case of starch synthases various isotypes are described which all catalyze a polymerization reaction by transferring a glucosyl residue of ADP-glucose to α-1,4-glucans. Branching enzymes catalyze the introduction of α-1,6 branchings into linear α-1,4-glucans.

Furthermore, it is discussed that other enzyme activities, such as hydrolytic or phosphorolytic activities, are involved in the synthesis of starch (Preiss in Oxford Survey of Plant Molecular and Cell Biology, Oxford University Press, Vol. 7 (1991), 59–114). It can furthermore not be precluded that the "R enzyme", or the so-called disproportionizing enzyme, and the starch phosphorylases also are involved in starch synthesis, although these enzymes so far have been connected with the degradation of starch.

Starch synthases may be divided up in two groups: the granule-bound starch syntheses (GBSS), which are mainly present bound to starch granules but also in soluble form, and the soluble starch synthases (SSS). Within these classifications, various isotypes are described for various species of plants. These isotypes differ from each other in their dependency on primer molecules (so-called "primer dependent" (type II) and "primer independent" (type I) starch synthases).

So far only in the case of the isotype GBSS I its exact function during starch synthesis has been successfully determined. Plants in which this enzyme activity has been strongly or completely reduced, synthesize starch free of amylose (a so-called "waxy" starch) (Shure et al., Cell 35 (1983), 225–233; Visser et al., Mol. Gen. Genet. 225 (1991), 289–296; WO 92/11376); therefore this enzyme has been assigned a decisive role in synthesizing amylose-starch. This phenomenon is also observed in the cells of the green alga *Chlamydomonas reinhardtii* (Delrue et al., J. Bacteriol. 174 (1992), 3612–3620). In the case of Chlamydomonas it was furthermore demonstrated that GBSS I is not only involved in the synthesis of amylose but also has a certain influence on amylopectin synthesis. In mutants which do not show any GBSS I activity a certain fraction of the normally synthesized amylopectin, exhibiting long chain glucans, is missing.

The functions of the other isotypes of the granule-bound starch synthases, particularly GBSS II, and of the soluble starch synthases are so far not clear. It is assumed that soluble starch synthases, together with branching enzymes, are involved in the synthesis of amylopectin (see, e.g., Ponstein et al., Plant Physiol. 92 (1990), 234–241) and that they play an important role in the regulation of starch synthesis rate.

For potato, the isotypes GBSS I, GBSS II, as well as two or three isotypes of the soluble starch synthases, which so far have not been characterized further, have been identified (Ponstein et al. Plant Physiol. 92 (1990), 234–241; Smith et al., Planta 182 (1990), 599–604; Hawker et al., Phytochemistry 11 (1972), 1287–1293). Also for pea a GBSS II could be found (Dry et al., The Plant Journal 2,2 (1992), 193–202).

A cDNA encoding GBSS I from potato as well as a genomic DNA have already been described (Visser et al., Plant Sci. 64 (1989), 185–192; van der Leij et al., Mol. Gen. Genet. 228 (1991), 240–248). So far, no nucleic acid sequences encoding further granule-bound starch synthases or one of the soluble starch synthase isotypes from potato, have been reported.

Soluble starch synthases have been identified in several other plant species apart from potato. Soluble starch synthases have for example been isolated in homogeneous form from pea (Denyer and Smith, Planta 186 (1992), 609–617) and maize (WO 94/09144). In the case of pea it was found that the isotype of the soluble starch synthase identified as SSS II is identical with the granule-bound starch synthase GBSS II (Denyer et al., Plant J. 4 (1993), 191–198). In the case of other plant species the existence of several SSS-isotypes was described by means of chromatographic methods, as for example in the case of barley (Tyynelä and Schulman, Physiologia Plantarum 89 (1993) 835–841; Kreis, Planta 148 (1980), 412–416), maize (Pollock and Preiss, Arch. Biochem. Biophys. 204 (1980), 578–588) and wheat (Rijven, Plant Physiol. 81 (1986), 448–453). However, DNA sequences encoding these proteins have so far not been described.

A cDNA encoding a soluble starch synthase so far has only been described for rice (Baba et al., Plant Physiol. 103 (1993), 565–573).

SUMMARY OF THE INVENTION

In order to provide possibilities for modifying any desired starch-storing plant in such a way that they will synthesize a modified starch, respective DNA sequences encoding the various isotypes of granule-bound or soluble starch synthases have to be identified.

Therefore, it was the object of the present invention to provide DNA molecules—especially from potato—encoding enzymes involved in starch biosynthesis and by means of which genetically modified plants may be produced that show an elevated or reduced activity of those enzymes, thereby prompting a modification in the chemical and/or physical properties of the starch synthesized in these plants.

This object has been achieved by the provision of the embodiments described in the claims.

The invention therefore relates to DNA molecules encoding starch synthases, particularly such DNA molecules encoding the granule-bound starch synthases of the isotype II, as well as DNA molecules encoding soluble starch synthases.

The present invention particularly relates to DNA molecules encoding proteins with the biological activity of a granule-bound starch synthase of the isotype II (GBSSII) or a biologically active fragment of such a protein, such molecules preferably encoding proteins having the amino acid sequence indicated under Seq ID No. 8. Particularly, the invention relates to DNA molecules having the nucleotide sequence indicated under Seq ID No. 7, preferably molecules comprising the coding region indicated under Seq ID No. 7.

The subject matter of the invention are also DNA molecules encoding a GBSSII and the sequence of which differs from the nucleotide sequences of the above-described DNA molecules due to the degeneracy of the genetic code.

Furthermore, the invention relates to DNA molecules encoding GBSSII and hybridizing to any of the above-described DNA molecules. Such DNA molecules preferably are derived from starch-storing plants, particularly from dicotyledonous plants, and particularly preferred from potato.

The GBSSII proteins encoded by the DNA molecules according to the invention preferably have a molecular weight of 85±5 kD. GBSSII proteins are mainly present bound to starch granules, however, they may also be present in soluble form.

Furthermore, the invention relates to DNA molecules encoding proteins with the biological activity of a soluble starch synthase of the isotype B (SSSB) or a biologically active fragment of such a protein, with such molecules preferably encoding proteins having the amino acid sequence indicated under Seq ID No. 10. In particular, the invention relates to DNA molecules having the nucleotide sequence indicated under Seq ID No. 9, preferably molecules comprising the coding region indicated under Seq ID No. 9.

Another subject matter of the invention are DNA molecules encoding an SSSB and the sequence of which differs from the nucleotide sequences of the above-described DNA molecules due to the degeneracy of the genetic code.

Furthermore, the invention relates to DNA molecules encoding SSSB and hybridizing to any of the above-described DNA molecules. An exception are the DNA molecules from rice. The SSSB proteins encoded by the DNA molecules according to the invention preferably have a molecular weight of 78±5 kD.

The enzymatic properties of the SSSB proteins are described in the examples.

The invention furthermore relates to DNA molecules encoding proteins with the biological activity of a soluble starch synthase of the isotype A (SSSA). Such proteins can, for example, be characterized in that they are recognized by an antibody that is directed to the peptide having the amino acid sequence $NH_2$-GTGGLRDTVENC-COOH (Seq ID No. 13).

The enzymatic properties of the SSSA proteins are described in the examples.

An example of a DNA molecule encoding such a protein is a DNA molecule having the coding region depicted under Seq ID No. 11. This DNA molecule may be used to isolate from other organisms, in particular plants, DNA molecules encoding the SSSA proteins.

Thus, the present invention also relates to DNA molecules encoding proteins with the biological activity of a soluble starch synthase of the isotype A (SSSA) or a biologically active fragment of such a protein, with such molecules preferably encoding proteins having the amino acid sequence indicated under Seq ID No. 12. The invention particularly relates to DNA molecules having the nucleotide sequence indicated under Seq ID No. 11, preferably molecules comprising the coding region indicated under Seq ID No. 11.

Another subject matter of the invention are DNA molecules encoding SSSA and the sequence of which differs from the nucleotide sequences of the above-described DNA molecules due to a degeneracy of the genetic code.

Furthermore, the present invention relates to DNA molecules encoding SSSA and hybridizing to any of the above-described DNA molecules.

The SSSA protein preferably has an apparent molecular weight of about 120 to 140 kD, particularly of about 135 kD, in SDS gel electrophoresis.

DETAILED DESCRIPTION OF THE INVENTION

In this invention the term "hybridization" signifies hybridization under conventional hybridizing conditions, preferably under stringent conditions as described for example in Sambrook et al., Molecular Cloning, A Laboratory Manual, 2nd Edition (1989) Cold Spring Harbor Laboratory Press, Cold Spring Harbor, N.Y.). DNA molecules hybridizing to the DNA molecules according to the invention can basically be derived from any organism (i.e., prokaryotes or eukaryotes, particularly from bacteria, fungi, algae, plants or animal organisms) which possesses such DNA molecules. Preferably, they originate from monocotyledonous or dicotyledonous plants, in particular from useful plants, and particularly preferred from starch-storing plants.

DNA molecules hybridizing to the molecules according to the invention may be isolated, e.g., from genomic or from cDNA libraries from various organisms.

The identification and isolation of such DNA molecules from plants or other organisms may take place by using the DNA molecules according to the invention or parts of these DNA molecules or, as the case may be, the reverse complement strands of these molecules, e.g., by hybridization according to standard methods (see, e.g., Sambrook et al., 1989, Molecular Cloning, A Laboratory Manual, 2nd Edition, Cold Spring Harbor Laboratory Press, Cold Spring Harbor, N.Y.).

As a probe for hybridization, e.g., DNA molecules may be used which exactly or basically contain the nucleotide sequences indicated under Seq ID No. 7, 9 or 11 or parts thereof. The fragments used as hybridization probe may also be synthetic DNA fragments which were produced by means of the conventional DNA synthesizing methods and the sequence of which is basically identical with that of a DNA molecule according to the invention. After identifying and isolating the genes hybridizing to the DNA sequences according to the invention, the sequence has to be determined and the properties of the proteins encoded by this sequence have to be analyzed.

The molecules hybridizing to the DNA molecules of the invention also comprise fragments, derivatives and allelic variants of the above-described DNA molecules which encode one of the proteins described above. Thereby, fragments are defined as parts of the DNA molecules, which are long enough in order to encode one of the described proteins. In this context, the term derivatives means that the DNA sequences of these molecules differ from the sequences of the above-mentioned DNA molecules at one or more positions and that they exhibit a high degree of homology to these DNA sequences. Hereby, homology means a sequence identity of at least 40%, in particular an identity of at least 60%, preferably of more than 80% and still more preferably a sequence identity of more than 90%. The deviations occurring when comparing with the above-described DNA molecules might have been caused by deletion, substitution, insertion or recombination. Moreover, homology means that functional and/or structural equivalence exists between the respective DNA molecules or the proteins they encode. The DNA molecules, which are homologous to the above-described DNA molecules and represent derivatives of these DNA molecules, are generally variations of these molecules, that constitute modifications which exert the same biological function. These variations may be naturally occurring variations, for example sequences derived from other organisms, or mutations, whereby these mutations may have occurred naturally or they may have been introduced by means of a specific mutagenesis. Moreover, the variations may be synthetically produced sequences. The allelic variants may be naturally occurring as well as synthetically produced variants or variants produced by recombinant DNA techniques.

The proteins encoded by the various variants of the DNA molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability; pH-optimum, temperature-optimum etc.

Significant characteristics of a starch synthase are: i) their localization within the stroma of the plastids of plant cells; ii) their capability of synthesizing linear $\alpha$-1,4-linked polyglucans using ADP-glucose as substrate. This activity can be determined as shown in Denyer and Smith (Planta 186 (1992), 606–617) or as described in the examples.

The DNA molecules according to the invention may basically originate from any organism expressing the proteins described, preferably from plants, particularly from starch-synthesizing or starch-storing plants. These plants may be monocotyledonous but also dicotyledonous plants. Particularly preferred are, e.g., cereals (such as barley, rye, oats, wheat, etc.), maize, rice, pea, cassava, potato, etc.

Furthermore, the invention relates to vectors, especially plasmids, cosmids, viruses, bacteriophages and other vectors common in genetic engineering, which contain the above-mentioned DNA molecules of the invention.

In a preferred embodiment the DNA molecules contained in the vectors are linked to DNA elements that ensure the transcription and synthesis of a translatable RNA in prokaryotic and eukaryotic cells.

The expression of the DNA molecules of the invention in prokaryotic cells, e.g., in *Escherichia coli*, is interesting insofar as this enables a more precise characterization of the enzymatic activities of the enzymes encoding these molecules. In particular, it is possible to characterize the product being synthesized by the respective enzymes in the absence of other enzymes which are involved in the starch synthesis of the plant cell. This makes it possible to draw conclusions about the function, which the respective protein exerts during the starch synthesis within the plant cell.

Moreover, it is possible to introduce various mutations into the DNA molecules of the invention by means of conventional molecular-biological techniques (see, e.g., Sambrook et al., 1989, Molecular Cloning, A Laboratory Manual, 2nd Edition, Cold Spring Harbor Laboratory Press, Cold Spring Harbor, N.Y.), whereby the synthesis of proteins with possibly modified biological properties is induced. By means of this it is on the one hand possible to produce deletion mutants, in which DNA molecules are produced by continuing deletions at the 5'- or the 3'-end of the encoding DNA-sequence. These DNA molecules may lead to the synthesis of correspondingly shortened proteins. Such deletions at the 5'-end of the nucleotide sequence make it possible, for example, to identify amino acid sequences which are responsible for the translocation of the enzyme in the plastids (transit peptides). This allows for the specific production of enzymes which due to the removal of the respective sequences are no longer located in the plastids but within the cytosol, or which due to the addition of other signal sequences are located in other compartments.

On the other hand, point mutations might also be introduced at positions where a modification of the amino acid sequence influences, for example, the enzyme activity or the regulation of the enzyme. In this way, e.g., mutants with a modified $K_m$-value may be produced, or mutants which are no longer subject to the regulation mechanisms by allosteric regulation or covalent modification usually occurring in cells.

Furthermore, mutants may be produced exhibiting a modified substrate or product specificity such as mutants that use ADP-glucose-6-phosphate instead of ADP-glucose as substrate. Moreover, mutants with a modified activity-temperature-profile may be produced.

For the genetic manipulation in prokaryotic cells the DNA molecules of the invention or parts of these molecules may be integrated into plasmids which allow for a mutagenesis or a sequence modification by recombination of DNA sequences. By means of standard methods (cf. Sambrook et al., 1989, Molecular Cloning: A laboratory manual, 2nd edition, Cold Spring Harbor Laboratory Press, NY, USA) base exchanges may be carried out or natural or synthetic sequences may be added. In order to connect the DNA fragments, adapters or linkers may be attached to the fragments. Moreover, use can be made of manipulations which offer suitable restriction sites or which remove superfluous DNA or restriction sites. Wherever use is made of inserts, deletions or substitutions, in vitro mutagenesis, "primer repair", restriction or ligation may be used. For analyzing use is usually made of a sequence analysis, a restriction analysis or further biochemico-molecularbiological methods.

In a further embodiment the invention relates to host cells, in particular prokaryotic or eukaryotic cells, which contain a DNA molecule of the invention as described above or a vector of the invention. These are preferably bacterial cells or plant cells.

Furthermore, the proteins encoded by the DNA molecules of the invention are the subject-matter of the invention as well as methods for their production whereby a host cell of the invention is cultivated under conditions that allow for a synthesis of the protein and whereby the protein is then isolated from the cultivated cells and/or the culture medium.

It was found that by making available the nucleic acid molecules of the invention it is now possible—by means of recombinant DNA techniques—to interfere with the starch metabolism of plants in a way so far impossible and to modify it in such a way that a starch is synthesized which, e.g., is modified, compared to the starch synthesized in wild-type plants, with respect to its physico-chemical properties, especially the amylose/amylopectin ratio, the degree of branching, the average chain length, the phosphate content, the pastification behavior, the size and/or the shape of the starch granule. Soluble starch synthases, play, e.g., a central role in the regulation of the synthesis rate of starch. There is the possibility of increasing the yield of genetically modified plants by increasing the activity of these enzymes or by making mutants available which are no longer subject to cell-specific regulation schemes and/or different temperature-dependencies with respect to their activity. The economic significance of the chance to interfere with the starch synthesis, namely of potato plants, is obvious: In Europe, for example, potato is one of the most important plants for producing starch apart from maize and wheat. About 20% of the starch produced in Europe per year is obtained from potatoes. Furthermore, potato starch exhibits some advantageous properties as compared to starch from maize or wheat, such as, e.g., a low protein and lipid content as well as relatively large starch granules and phosphate content. Therefore, if possible, potato starch is preferably used.

Therefore, it is possible to express the DNA molecules of the invention in plant cells in order to increase the activity of one or more starch synthases. Furthermore, the DNA molecules of the invention may be modified by means of methods known to the skilled person, in order to produce starch synthases which are no longer subject to the cell-specific regulation mechanisms or show modified temperature-dependencies or substrate or product specificities.

The synthesized protein may in principle be located in any desired compartment within the plant cell. In order to locate it within a specific compartment, the sequence ensuring the localization in the plastids must be deleted and the remaining coding regions optionally have to be linked to DNA sequences which ensure localization in the respective compartment. Such sequences are known (see, e.g., Braun et al., 1992, EMBO J. 11:3219–3227; Wolter et al., 1988, Proc. Natl. Acad. Sci. USA 85: 846–850; Sonnewald et al., 1991, Plant J. 1:95–106).

Thus, the present invention also relates to transgenic plant cells containing a DNA molecule of the invention, this DNA molecule being linked to regulatory DNA elements, which ensure the transcription in plant cells, especially with a promoter which is heterologous with respect to the DNA molecule.

By means of methods known to the skilled person the transgenic plant cells can be regenerated to whole plants. Thus, the plants obtained by regenerating the transgenic plant cells of the invention are also the subject-matter of the present invention. A further subject-matter of the invention are plants which contain the above-described transgenic plant cells. The transgenic plants may in principle be plants of any desired species, i.e., they may be monocotyledonous as well as dicotyledonous plants. These are preferably useful plants, such as cereals (rye, barley, oats, wheat etc.), rice, maize, peas, cassava or potatoes. The invention also relates to propagation material of the plants of the invention, e.g., fruits, seeds, tubers, cuttings etc.

Due to the expression or, as the case may be, additional expression of a DNA molecule of the invention, the transgenic plant cells and plants of the invention synthesize a starch which compared to starch synthesized in wild-type plants, i.e., non-transformed plants, is modified, in particular with respect to the viscosity of aqueous solutions of this starch and/or the phosphate content. Thus, the starch derived from transgenic plant cells and plants according to the invention is the subject-matter of the present invention.

A further subject-matter of the invention are transgenic plant cells, in which the activity of a protein according to the invention is reduced when compared to non-transformed plants. It was found that plant cells exhibiting a reduced activity of a protein of the invention synthesize a starch having modified chemical and/or physical properties as compared to that of wild-type plant cells.

The production of plant cells with a reduced activity of a protein of the invention may for example be achieved by using the DNA molecules of the invention. Possibilities are the expression of a corresponding antisense-RNA, of a sense-RNA for achieving a cosupression effect or the expression of a correspondingly constructed ribozyme, which specifically cleaves transcripts encoding a protein of the invention.

Preferably, an antisense RNA is expressed to reduce the activity of a protein of the invention in plant cells.

For this purpose, a DNA molecule can be used which comprises the complete sequence encoding a protein of the invention, including possibly existing flanking sequences as well as DNA molecules, which only comprise parts of the encoding sequence whereby these parts have to be long enough in order to prompt an antisense-effect within the cells. Basically, sequences with a minimum length of 15 bp, preferably with a length of 100–500 bp and for an efficient antisense-inhibition, in particular sequences with a length of more than 500 bp may be used. Generally DNA-molecules are used which are shorter than 5000 bp, preferably sequences with a length of less than 2500 bp. Preferably, use is made of DNA molecules that are homologous with respect to the plant species to be transformed.

Use may also be made of DNA sequences which are highly homologous, but not completely identical to the sequences of the DNA molecules of the invention. The minimal homology should be more than about 65%. Preferably, use should be made of sequences with homologies between 95 and 100%.

The transgenic plant cells of the invention can be regenerated to whole plants by means of methods known to the skilled person. Thus, plants containing the transgenic plant cells of the invention are also the subject-matter of the present invention. These plants generally are plants of any species, i.e., monocotyledonous and dicotyledonous plant. Preferably these plants are useful plants, especially starch-storing plants such as cereals (rye, barley, oats, wheat, etc.), rice, maize, peas, cassava or potatoes. The invention also relates to propagation material of the plants of the invention, such as fruit, seeds, tubers, cuttings, etc.

Due to the reduction of the activity of one of the proteins of the invention, the transgenic plant cells and plants of the invention synthesize a starch which is modified, compared to the starch from non-transformed plant cells or plants, in its chemical and/or physical properties. This starch exhibits for example a modified viscosity of its aqueous solutions and/or a modified phosphate content.

Thus, starch derived from the above-mentioned transgenic plant cells and plants is also the subject-matter of the invention.

The starches of the invention may be modified according to techniques known to the skilled person; in unmodified as well as in modified form they are suitable for use in foodstuffs or non-foodstuffs.

Basically, the possibilities of uses of the starch can be subdivided into two major fields. One field comprises the hydrolysis products of starch which mainly include glucose and glucan components obtained by enzymatic or chemical processes. They serve as starting materials for further chemical modifications and processes such as fermentation. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g., increased surface of the grain, improved digestibility due to less branching or a steric structure, which limits the accessibility for the used enzymes.

The other area in which starch is used due to its polymer structure as so-called native starch, can be subdivided into two further areas:

1. Use in Foodstuffs

Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with, e.g., inorganic or organic ions.

2. Use in Non-foodstuffs

The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.

2.1 Paper and Cardboard Industry

Within the paper production process, a differentiation can be made between four fields of application, namely surface, coating, mass and spraying.

The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive Industry

A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textile and Textile Care Industry

Another possible use as adjuvant and additive is in the production of textiles and textile care products. Within the textile industry, a differentiation can be made between the following four fields of application: the use of starch as a sizing agent, i.e., as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as a thickener in the production of dye pastes for the prevention of dye diffusion and as an additive for warping agents for sewing yarns.

2.4 Building Industry

The fourth area of application of starch is its use as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground Stabilization

Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and incrustation-reducing effect as the products used so far; however, they are considerably less expensive.

2.6 Use of Starch in Plant Protectives and Fertilizers

Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, Medicine and Cosmetics Industry

Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

2.8 Starch as an Additive in Coal and Briquettes

The use of starch as an additive in coal and briquettes is also thinkable. By adding starch, coal can be quantitatively agglomerated and/or briquetted in high quality, thus preventing premature disintegration of the briquettes.

Barbecue coal contains between 4 and 6% added starch, calorated coal between 0.1 and 0.5%. Furthermore, the starch is suitable as a binding agent since adding it to coal and briquette can considerably reduce the emission of toxic substances.

2.9 Processing of Ore and Coal Slurry

Furthermore, the starch may be used as a flocculant in the processing of ore and coal slurry.

2.10 Starch as an Additive in Casting

Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill more prerequisites for the production process, such as dispersability in cold water, rehydratisability, good mixability in sand and high capability of binding water.

2.11 Use of Starch in Rubber Industry

In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

2.12 Production of Leather Substitutes

Another field of application for the modified starch is the production of leather substitutes.

2.13 Starch in Synthetic Polymers

In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes. Present disadvantages relate to insufficient transparency, reduced tensile strength as well as reduced extensibility.

Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. The fields of application of these super absorbers have extended over the last few years and they are used mainly in the hygiene field, e.g., in products such as diapers and sheets, as well as in the agricultural sector, e.g., in seed pellets.

What is decisive for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known to the person skilled in the art. These are particularly modifications by means of heat treatment acid treatment oxidation and esterification leading to the formation of phosphate, nitrate, sulfate, xanthate, acetate and citrate starches. Other organic acids may also be used for the esterification:

formation of starch ethers starch alkyl ether, O-allyl ether, hydroxylalkyl ether, O-carboxylmethyl ether, N-containing starch ethers, P-containing starch ethers and S-containing starch ethers.

formation of branched starches formation of starch graft polymers.

In order to express the DNA molecules of the invention in sense- or antisense-orientation in plant cells, these are linked to regulatory DNA elements which ensure the transcription in plant cells. Such regulatory DNA elements are particularly promoters.

The promoter may be selected in such a way that the expression takes place constitutively or in a certain tissue, at a certain point of time of the plant development or at a point of time determined by external circumstances. With respect to the plant the promoter may be homologous or heterologous. A suitable promoter for a constitutive expression is, e.g., the 35S RNA promoter of the Cauliflower Mosaic Virus. For a tuber-specific expression in potatoes the patatin gene promoter B33 (Rocha-Sosa et al., EMBO J. 8 (1989), 23–29) or a promoter which ensures expression only in photosynthetically active tissues, e.g., the ST-LS1 promoter (Stockhaus et al., Proc. Natl. Acad. Sci. USA 84 (1987), 7943–7947; Stockhaus et al., EMBO J. 8 (1989), 2445–2451) may be used. For an endosperm-specific expression the HMG promoter from wheat, or promoters from zein genes from maize are suitable.

Furthermore, a termination sequence may exist which serves to correctly end the transcription and to add a poly-A-tail to the transcript which is believed to stabilize the transcripts. Such elements are described in the literature (cf. Gielen et al., EMBO J. 8 (1989), 23–29) and can be exchanged as desired.

According to the invention, it is basically possible to produce plants in which only the activity of one isotype of the SSS or the GBSS II is modified, and also plants in which the activities of several starch synthase forms are simultaneously modified. Thereby, all kinds of combinations and permutations are thinkable.

By modifying the activities of one or more isotypes of the starch synthases in plants, a synthesis of a starch modified in its structure is brought about.

By increasing the activity of one or more isotypes of the starch synthases in the cells of the starch-storing tissue of transformed plants such as in the potato tuber or in the endosperm of maize or wheat, increased yields may be the result.

Since the DNA sequence encoding the GBSS I from potato is already known (Visser et al., Plant Sci. 64 (1989), 185–192), DNA sequences encoding all starch synthases so far identified in potato are available. This allows for the identification of the function of the individual isotypes in the starch biosynthesis as well as for the production of genetically modified plants in which the activity of at least one of these enzymes is modified. This enables the synthesis of starch with a modified structure and therefore with modified physico-chemical properties in the plants manipulated in such a way.

The DNA molecules of the invention may be used in order to produce plants in which the activity of the starch synthases mentioned is elevated or reduced and in which at the same time the activities of other enzymes involved in the starch biosynthesis are modified. Thereby, all kinds of combinations and permutations are thinkable. For example, DNA molecules encoding the SSS proteins or GBSS II may be introduced into plant cells according to the process described above in which the synthesis of endogenous GBSS I-proteins is already inhibited due to an antisense-effect (as described in Visser et al., Mol. Gen. Genet. 225 (1991), 289–296),or in which the synthesis of the branching enzyme is inhibited (as described in WO92/14827).

If the inhibition of the synthesis of several starch synthases in transformed plants is to be achieved, DNA molecules can be used for transformation, which at the same time contain several regions in antisense-orientation controlled by a suitable promoter and encoding the corresponding starch synthases. Hereby, each sequence may be controlled by its own promoter or else the sequences may be transcribed as a fusion of a common promoter. The last alternative will generally be preferred as in this case the synthesis of the respective proteins should be inhibited to approximately the same extent.

Furthermore, it is possible to construct DNA molecules in which apart from DNA sequences encoding starch synthases other DNA sequences are present encoding other proteins involved in the starch synthesis or modification and coupled to a suitable promoter in antisense orientation. Hereby, the sequences may again be connected up in series and be transcribed by a common promoter. For the length of the individual coding regions used in such a c construct the above-mentioned facts concerning the production of antisense-construct are also true. There is no upper limit for the number of antisense fragments transcribed from a promoter in such a DNA molecule. The resulting transcript, however, should not be longer than 10 kb, preferably 5 kb.

Coding regions which are located in antisense-orientation behind a suitable promoter in such DNA molecules in combination with other coding regions, may be derived from DNA sequences encoding the following proteins: granule-bound starch synthases (GBSS I and II), other soluble starch synthases (SSS I and II), branching enzymes (KoBmann et al., Mol. Gen. Genet. 230 (1991) 39–44), debranching enzymes (R enzymes), disproportionizing enzymes (Takaha et al., J. Biol. Chem. 268 (1993), 1391–1396) and starch phosphorylases. This enumeration merely serves as an example. The use of other DNA sequences within the framework of such a combination is also thinkable.

By means of such constructs it is possible to inhibit the synthesis of several enzymes at the same time within the plant cells transformed with these molecules.

In order to prepare the integration of foreign genes into higher plants a high number of cloning vectors are at disposal, containing a replication signal for E. coli and a marker gene for the selection of transformed bacterial cells. Examples for such vectors are pBR322, pUC series, M13mp series, pACYC184 etc. The desired sequence may be integrated into the vector at a suitable restriction site. The obtained plasmid is used for the transformation of *E. coli* cells. Transformed *E. coli* cells are cultivated in a suitable medium end subsequently harvested and lysed. The plasmid is recovered. As an analyzing method for the characterization of the obtained plasmid DNA use is generally made of restriction analysis, gel electrophoresis and other biochemico-molecularbiological methods. After each manipulation the plasmid DNA may be cleaved and the obtained DNA fragments may be linked to other DNA sequences. Each plasmid DNA may be cloned into the same or in other plasmids.

In order to integrate DNA into plant host cells a wide range of techniques are at disposal. These techniques comprise the transformation of plant cells with T-DNA by using *Agrobacterium tumefaciens* or *Agrobacterium rhizogenes* as transformation medium, the fusion of protoplasts, the injection and the electroporation of DNA, the integration of DNA by means of the biolistic method as well as further possibilities.

In the case of injection and electroporation of DNA into plant cells, there are no special demands made to the plasmids used. Simple plasmids such as pUC derivatives may be used. However, in case that whole plants are to be regenerated from cells transformed in such a way, a selectable marker gene should be present.

Depending on the method of integrating desired genes into the plant cell, further DNA sequences may be necessary. If the Ti- or Ri-plasmid is used, e.g., for the transformation of the plant cell, at least the right border, more frequently, however, the right and left border of the Ti- and Ri-plasmid T-DNA has to be connected to the foreign gene to be integrated as a flanking region.

If Agrobacteria are used for the transformation, the DNA which is to be integrated must be cloned into special plasmids, namely either into an intermediate vector or into a binary vector. Due to sequences homologous to the sequences within the T-DNA, the intermediate vectors may be integrated into the Ti- or Ri-plasmid of the Agrobacterium due to homologous recombination. This also contains the vir-region necessary for the transfer of the T-DNA. Intermediate vectors cannot replicate in Agrobacteria. By means of a helper plasmid the intermediate vector may be transferred to *Agrobacterium tumefaciens* (conjugation). Binary vectors may replicate in *E. coli* as well as in Agrobacteria. They contain a selectable marker gene as well as a linker or polylinker which is framed by the right and the left T-DNA border region. They may be transformed directly into the Agrobacteria (Holsters et al. Mol. Gen. Genet. 163 (1978), 181–187). The Agrobacterium acting as host cell should contain a plasmid carrying a vir-region. The vir-region is necessary for the transfer of the T-DNA into the plant cell. Additional T-DNA may be present. The Agrobacterium transformed in such a way is used for the transformation of plant cells.

The use of T-DNA for the transformation of plant cells was investigated intensely and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

For transferring the DNA into the plant cells, plant explants may suitably be co-cultivated with *Agrobacterium tumefaciens* or *Agrobacterium rhizogenes*. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the integrated DNA is present or not. Other possibilities in order to integrate foreign DNA by using the biolistic method or by transforming protoplasts are known to the skilled person (cf., e.g., Willmitzer, L., 1993 Transgenic plants. In: Biotechnology, A Multi-Volume Comprehensive Treatise (H. J. Rehm, G. Reed, A. Puhler, P. Stadler, editors), Vol. 2, 627–659, VCH Weinheim-New York-Basel-Cambridge).

Once the introduced DNA has been integrated in the genome of the plant cell, it usually continues to be stable there and also remains within the descendants of the originally transformed cell. It usually contains a selectable marker which confers resistance against a biozide or against an antibiotic such as kanamycin, G 418, bleomycin, hygromycin or phosphinotricine, etc. to the transformed plant cells. The individually selected marker should therefore allow for a selection of transformed cells to cells lacking the integrated DNA.

The transformed cells grow in the usual way within the plants (see also McCormick et al., 1986, Plant Cell Reports 5: 81–84).

The resulting plants can be cultivated in the usual way and cross-bred with plants having the same transformed genetic heritage or another genetic heritage. The resulting hybrid individuals have the corresponding phenotypic properties. Two or more generations should be grown in order to ensure whether the phenotypic feature is kept stably and whether it is transferred. Furthermore, seeds should be harvested in order to ensure that the corresponding phenotype or other properties will remain.

The plasmid pBinARHyg used in this invention was deposited with Deutsche Sammlung von Mikroorganismen (DSM) [German collection of microorganisms] in Brunswick, Federal Republic of Germany, as international recognized depositary authority in accordance with the stipulations of the Budapest Treaty on the International Recognition of the Deposit of Microorganisms for the Purposes of Patent Procedure on Jan. 20, 1994 under deposit no. DSM 9505.

Abbreviations used bp base pair

GBSS granule-bound starch synthase

IPTG isopropyl β-D-thiogalacto-pyranoside

SSS soluble starch synthase

PMSF phenylmethylsulfonylfluoride

VK full-length clone

Media and solutions used in the examples:

20×SSC
    175.3 g NaCl
    88.2 g sodium citrate
    ad 1000 ml with dd$H_2O$
    pH 7.0 with 10 N NaOH Buffer A
    50 mM Tris-HCl pH 8.0
    2.5mM DTT
    2 mM EDTA
    0.4 mM PMSF
    10% glycerol
    0.1% sodium dithionite Buffer B
    50 mM Tris-HCl pH 7.6
    2.5 mM DTT
    2 mM EDTA Buffer C
    0.5 M sodium citrate pH 7.6
    50 mM Tris-HCl pH 7.6
    2.5 mM DTT
    2 mM EDTA
10×TBS
    0.2 M Tris-HCl pH 7.5
    5.0 M NaCl
10×TBST
    10×TBS
    0.1% (vol./vol.) Tween 20
Elution buffer
    25 mM Tris pH 8.3
    250 mM glycine
Dialysis buffer
    50 mM Tris-HCl pH 7.0
    50 mM NaCl
    2 mM EDTA
    14.7 mM β-mercaptoethanol
    0.5 mM PMSF
Protein buffer
    50 mM sodium phosphate buffer pH 7.2
    10 mM EDTA
    0.5 mM PMSF
    14.7 mM β-mercaptoethanol

BRIEF DESCRIPTION OF THE DRAWINGS

FIG. 7 shows a partial comparison of the amino acid sequences of prokaryotic glycogen synthases, granule-bound starch synthases and soluble starch synthases from various organisms.
    a: glycogen synthase from *E. coli*
    b: GBSS I from barley
    c: GBSS I from wheat
    d: GBSS I from maize
    e: GBSS I from rice
    f: GBSS I from cassava
    g: GBSS I from potato
    h: GBSS II from pea
    i: GBSS II from potato
    k: SSS from rice
    l: SSS A from potato
    m: SSS B from potato
The marked regions (I), (II) and (III) indicate three peptide sequences which are strongly conserved between the various starch synthases and glycogen synthases.

Figure 1:
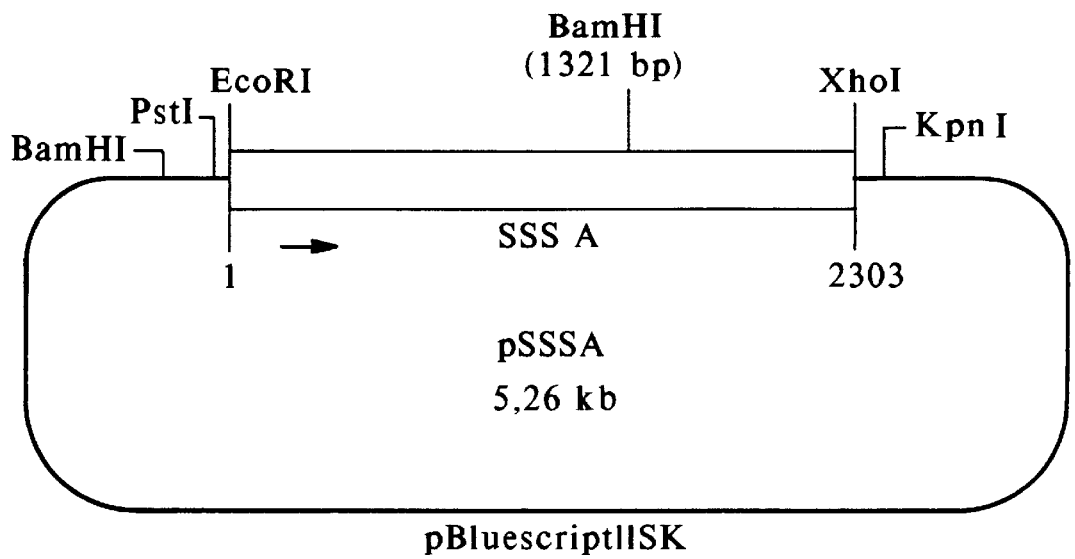
FIG. 1 shows plasmid PSSSA
The thin line corresponds to the sequence of pBluescript II SK(−). The thick line represents the cDNA encoding the SSS A isotype from *Solanum tuberosum*. The restriction sites of the insert are indicated. The cDNA insert is ligated between the EcoR I and Xho I restriction sites of the polylinker of the plasmid. The DNA sequence of the cDNA insert is indicated under Seq ID No. 1.

The examples serve to illustrate the invention.
In the examples, the following methods were used:
1. Cloning Methods
    Vector pBluescript II SK (Stratagene) was used for cloning in *E. coli*.
    For plant transformation, the gene constructs were cloned into the binary vector pBinAR Hyg (DSM 9505).
2. Bacterial Strains
    For the Bluescript vector and for the pBinAR Hyg constructs the *E. coli* strain DH5α (Bethesda Research Laboratories, Gaithersburg, USA) was used. For the in vivo excision the *E. coli* strain XL1-Blue was used.

The transformation of the plasmids in the potato plants was carried out using the *Agrobacterium tumefaciens* strain C58C1 pGV2260 (Deblaere et al., Nucl. Acids Res. 13 (1985), 4777–4788).

3. Transformation of *Agrobacterium tumefaciens*

The transfer of the DNA was carried out by direct transformation according to the method by Höfgen & Willmitzer (Nucl. Acids Res. 16 (1988), 9877). The plasmid DNA of transformed Agrobacteria was isolated according to the method by Birnboim & Doly (Nucl. Acids Res. 7 (1979), 1513–1523) and was analyzed gel electrophoretically after suitable restriction digestion.

4. Transformation of Potatoes

Ten small leaves of a potato sterile culture (*Solanum tuberosum* L.cv. Désirée) were wounded with a scalpel and placed in 10 ml MS medium (Murashige & Skoog, Physiol. Plant. 15 (1962), 473) containing 2% sucrose which contained 50 µl of a selectively grown overnight culture of *Agrobacterium tumefaciens*. After gently shaking the mixture for 3–5 minutes it was further incubated in the dark for 2 days. For callus induction the leaves were placed on MS medium containing 1.6% glucose, 5 mg/l naphthyl acetic acid, 0.2 mg/l benzyl aminopurine, 250 mg/l claforan, 50 mg/l kanamycin, and 0.80% Bacto Agar. After incubation at 25° C. and 3,000 lux for one week the leaves were placed for shoot induction on MS medium containing 1.6% glucose, 1.4 mg/l zeatin ribose, 20 mg/l naphthyl acetic acid, 20 mg/l giberellic acid, 250 mg/l claforan, 50 mg/l kanamycin and 0.80% Bacto Agar.

5. Radioactive Labeling of DNA Fragments

The DNA fragments were radioactively labeled using a DNA Random Primer Labelling Kit of Boehringer (Germany) according to the manufacturer's information.

6. Determination of the Starch Synthase Activity

The starch synthase activity was determined via the determination of the incorporation of $^{14}C$ glucose from ADP [$^{14}C$ glucose] into a product insoluble in methanol/KCl as described by Denyer and Smith (Planta 186 (1992), 609–617).

7. Detection of Soluble Starch Synthases in the Native Gel

In order to detect the activity of soluble starch synthases by non-denaturing gel electrophoresis tissue samples of potato tubers were extracted with 50 mM Tris-HCl pH 7.6, 2 mM DTT, 2.5 mM EDTA, 10% glycerol and 0.4 mM PMSF. Electrophoresis was carried out in a MiniProtean II chamber (BioRAD). The monomer concentration of the gels having 1.5 mm thickness was 7.5% (wt./vol.). 25 mM Tris-glycine pH 8.4 served as gel and running buffer. Equal amounts of protein extract were applied and separated for 2 hrs at 10 mA per gel.

The activity gels were subsequently incubated in 50 mM tricine NaOH pH 8.5, 25 mM potassium acetate, 2 mM EDTA, 2 mM DTT, 1 mM ADP glucose, 0.1% (wt./vol.) amylopectin and 0.5 M sodium citrate. The glucans formed were dyed with Lugol's solution.

8. Starch Analysis

The starch produced by the transgenic potato plants was characterized using the following methods:

a) Determination of the phosphate content

In potato starch some glucose units may be phosphorylated at the carbon atoms at positions C3 and C6. In order to determine the phosphorylation degree at the C6 position of the glucose 100 mg starch were hydrolyzed in 1 ml 0.7 M HCl at 95° C. for 4 hours (Nielsen et al., Plant Physiol. 105 (1994), 111–117). After neutralization with 0.7 M KOH, 50 µl of the hydrolysate were subjected to a photometric-enzymatic test to determine the glucose-6-phosphate content. The alteration of the absorption of the test mixture (100 mM imidazole/HCl; 10 mM $MgCl_2$; 0.4 mM NAD; 2 units glucose-6-phosphate dehydrogenase from *Leuconostoc mesenteroides*; 30° C.) was measured at 334 nm.

b) Analysis of the side chain length distribution

For an analysis of the side chains of the starch molecules 1 ml of a 0.1% starch solution was digested with about 1 unit isoamylase overnight at 37° C. in 100 mM sodium citrate buffer, pH 4.0 (Y. C. Lee, Analytical Biochemistry 189 (1990), 151–162). The individual glucan chains were separated via a complex gradient on HPLC (column PA1; elution with 150 mM NaOH with sodium acetate gradients).

c) Determination of granule size

The granule size was determined with a photosedimentometer of the "Lumosed" type by Retsch GmbH, Germany. For this purpose, 0.2 g starch were suspended in about 150 ml water and measured immediately. The program supplied by the manufacturer together with the photosedimentometer calculated the average diameter of the starch granules based on an average density of the starch of 1.5 g/l.

d) Pastification properties

The pastification curves of the starch were recorded with a Viskograph E of Brabender oHG, Germany, or with a Rapid Visco Analyser, Newport Scientific Pty Ltd, Investment Support Group, Warriewood NSW 2102, Australia. When the Viskograph E was used, a suspension of 30 g starch in 450 ml water was subjected to the following heating regimen: heating up from 50° C. to 96° C. at 3°/min, maintaining constant for 30 minutes, cooling off to 30° C. at 3°/min and maintaining constant for another 30 minutes. The temperature profile yielded characteristic pastification properties.

When the Rapid Visco Analyser was used, a suspension of 2 g starch in 25 ml water was subjected to the following heating regimen: suspending at 50° C. for 50 s, heating up from 50° C. to 95° C. at 12°/min, maintaining constant for 2.5 minutes, cooling off to 50° C. at 16.4°/min and maintaining constant for another 2 minutes. The temperature profile yielded the maximum and the final viscosity as well as the pastification temperature.

EXAMPLE 1

Identification, Isolation and Characterization of Two cDNAs Encoding the Isotypes SSS B and GBSS II of the Starch Synthase from *Solanum tuberosum*.

Although SSS proteins have already been detected in a variety of plant species, inter alia in potato, and cDNA sequences have been described for SSS proteins from rice (Baba et al., supra), the purification of these proteins from potato or other plants as well as the identification of such DNA sequences has not been successful. The problem in isolating such DNA sequences resides in that the homogeneous purification of soluble starch synthases so far has not been successful due to technical reasons, although it has been attempted many times. The soluble synthases co-purify in all purification steps with the branching enzyme and other impurities. Therefore, these proteins have not been amenable to the detection of partial amino acid sequences. It is hence extremely difficult to identify cDNA sequences by hybridization to degenerate oligonucleotides derived from the amino acid sequence. For the same reasons, it is not possible to develop antibodies which specifically recognize these enzymes and thus could be used to screen expression libraries.

The prerequisite for the isolation of DNA sequences encoding SSS proteins from potato by hybridization to heterologous probes encoding the soluble starch synthases from other plant species is that there is sufficiently high homology and at the same time no significant homologies to other encoding DNA sequences. In the case of the only heterologous DNA sequence from rice available (Baba et al., supra), however, it was known that it has high homologies to the granule-bound starch synthases from rice as well as to GBSS I and therefore presumably also to GBSS II from potato. Due to these high homologies to GBSS I and II cross-hybridizations occur to GBSS I and II cDNAs when screening cDNA libraries. The identification of cDNAs which encode SSS proteins can therefore only be achieved by differential screening. This, however, requires the availability of cDNA sequences for GBSS I and II proteins from potato. cDNA sequences encoding GBSS I from potato, however, have not been available so far.

In the following, the isolation of a cDNA encoding a soluble starch synthase from potato is described.

For this purpose, a DNA fragment from a cDNA from rice encoding a soluble starch synthase (Baba et al., 1993, Plant Physiol. 103:565–573) was amplified using the polymerase chain reaction.

The following oligonucleotides were used as primers:
oligonucleotide 1: 5'-ACAGGATCCTGTGCTATGC-GGCGTGTGAAG-3' (Seq ID No. 14)
Oligonucleotide 2: 5'-TTGGGATCCGCAATGCCCAC-AGCATTTTTTC-3' (Seq ID No. 15)

The fragment resulting from PCR was 1067 bp long. This DNA fragment was later on used as heterologous probe for the identification of cDNA sequences from potato encoding soluble starch synthases.

For the preparation of a cDNA library, poly(A$^+$) mRNA was isolated from potato tubers of the potato variety "Berolina". Starting from the poly(A$^+$) mRNA cDNA was prepared according to the method of Gubler and Hoffmann (1983, Gene 25:263–269) using an Xho I oligo d(t)$_{18}$ primer. This cDNA was first provided with an EcoR I linker and then digested with Xho I and ligated in a specific orientation into a lambda ZAP II vector (Stratagene) which had been digested with EcoR I and Xho I.

500,000 plaques of a thus constructed cDNA library were screened for DNA sequences which are homologous to the heterologous probe of rice using said probe. Since the probe from rice used strongly cross-hybridizes to various sequences from potato, a direct identification of cDNA molecules encoding soluble starch synthases was not possible. From homology comparisons it was known that the cDNA encoding the SSS protein from rice has a high homology to the GBSS I cDNA already isolated from potato. Since GBSS I and GBSS II exhibit high homologies in other organisms, it could be presumed that the probe from rice would also exhibit a high homology to GBSS II sequences from potato. In order to make an identification of cDNA sequences possible which encode a soluble starch synthase from potato, it was therefore necessary to have sequences available encoding GBSS I and II from potato. DNA sequences encoding GBSS I from potato had already been described, however, none encoding GBSS II from potato. Therefore, a cDNA was isolated encoding the GBSS II from potato.

For this purpose, granule-bound proteins from potato starch were isolated. The isolation was carried out by electroelution in an elution device which was constructed in analogy to the "Model 422 Electro-Eluter" (BIORAD Laboratories Inc., USA) but had a substantially greater volume (about 200 ml). 25 g dried starch were dissolved in elution buffer (final volume 80 ml). The suspension was heated in a water bath to 70–80° C. 72.07 g urea were added (final concentration 8 M) and the volume was filled up with elution buffer to give 180 ml. The starch was dissolved under constant stirring and developed a glue-like consistency.

The proteins were electroeluted overnight from the solution using the elution device (100 V; 50–60 mA). The proteins eluted were carefully removed from the device. Suspended matter was removed by short centrifugation. The supernatant was dialyzed 2–3 times for one hour each at 4° C. against dialysis buffer. Then, the volume of the protein solution was determined. The proteins were precipitated by adding ammonium sulfate (90% final concentration) while constantly stirring the solution at 0° C. The proteins precipitated were sedimented by centrifugation and dissolved in protein buffer.

The proteins isolated were used to prepare polyclonal antibodies from rabbits which specifically detect granule-bound proteins. With the help of such antibodies a cDNA expression library was then screened by standard methods for sequences encoding the granule-bound proteins. The expression library was prepared as described above.

Positive phage clones were purified further using standard techniques. By way of the in vivo excision method *E. coli* clones were obtained from positive phage clones which contain a double-stranded pBluescript plasmid exhibiting the respective cDNA insert. After ascertaining the size and the restriction pattern of the inserts suitable clones were analyzed further. A clone cGBSSII was identified as a clone encoding the GBSSII protein.

Figure 5:
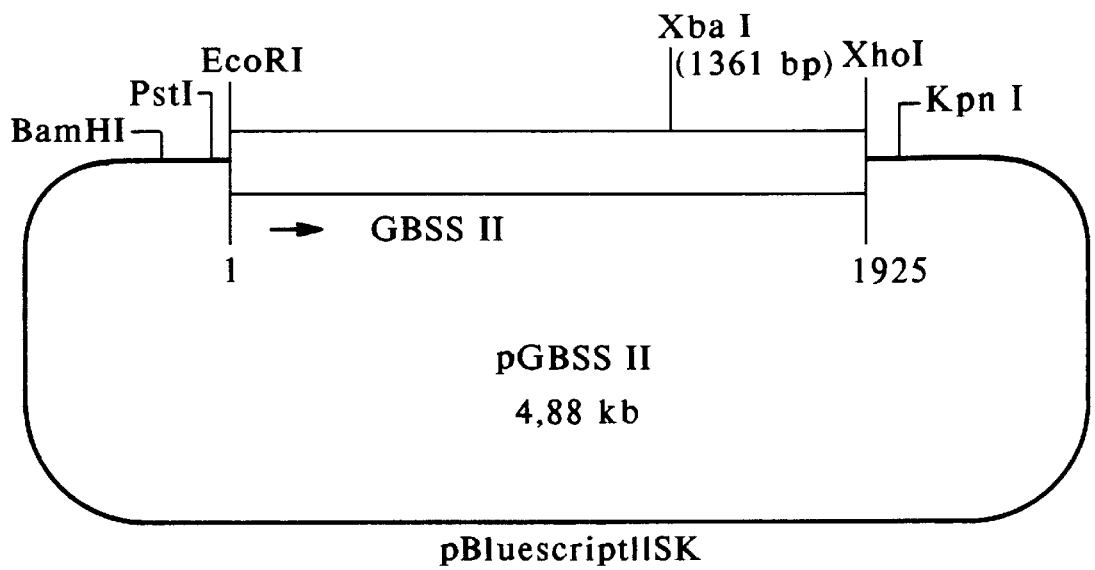
FIGS. 5A–5D show plasmid pGBSSII
The thin line corresponds to the sequence of pBluescript II SK(−). The thick line represents the cDNA encoding the GBSS II isotype from *Solanum tuberosum*. The restriction sites of the insert are indicated. The cDNA insert is ligated between the EcoR I and Xho I restriction sites of the polylinker of the plasmid. The DNA sequence of the cDNA insert is indicated under SEQ ID NO: 5.

From this clone, plasmid pGBSSII (FIG. 5) was isolated and its cDNA insert was determined by standard techniques by the dideoxynucleotide method (Sanger et al., Proc. Natl. Acad. Sci. USA 84 (1977), 5463–5467). The insert is 1925 bp long and is merely a partial cDNA sequence. The nucleotide sequence is indicated under Seq ID No. 5. Sequence comparisons showed that this DNA sequence, too, in various sites exhibited high homologies to the cDNA from rice encoding soluble starch synthase. Therefore, these sequences hybridize to the probe from rice when the cDNA library is screened.

The insert of this plasmid was later on used as probe in the screening of a cDNA library from potato to identify sequences encoding GBSS II proteins.

When screening the expression library with the polyclonal antibodies which are directed to the granule-bound proteins clones were isolated besides the clone cGBSSII that exhibited the cDNA inserts encoding GBSS I from potato. From one of these clones, cGBSSI, plasmid pGBSSI was isolated and the sequence of the cDNA insert was determined. This sequence substantially corresponded to the known DNA sequences encoding GBSSI from potato (Visser et al., Plant Sci. 64 (1989), 185–192; van der Leij et al., Mol. Gen. Genet. 228 (1990), 240–248). This cDNA insert, obtained in plasmid pGBSS I, was therefore later on used as probe when screening a cDNA library from potato tubers in order to identify sequences encoding the GBSS I proteins.

The above-described cDNA library from potato was first screened for sequences encoding GBSS I or GBSS II from potato. For this purpose, the phage plaques were transferred to nitrocellulose filters, the DNA was denatured by NaOH treatment, the filters were neutralized and the DNA was fixated on the filters by heat treatment. The filters were prehybridized for 2 hours at 42° C. in 0.25 M NaHPO$_4$, pH 7.2, 0.25 M NaCl, 7% SDS, 1 mM EDTA, 25% formamide, 10% PEG. Then the filters were hybridized overnight at 42°

C. in 0.25 M NaHPO$_4$, pH 7.2, 0.25 M NaCl, 7% SDS, 1 mM EDTA, 25% formamide, 10% PEG after the respective radioactively labeled probe had been added. As probe on the one hand the cDNA insert from plasmid pGBSSII was used and one the other hand the cDNA insert from plasmid pGBSSI.

The filters were subsequently washed 2×30 min in 0.1× SSC, 0.5% SDS at 65° C. and exposed on X-ray films.

In a parallel procedure, filters of the same cDNA library were hybridized under the same conditions as described for GBSS I and GBSS II with the radioactively labeled cDNA probe derived from rice. The washing of the filters was carried out in this case for 2×30 min at 40° C. with 2×SSC, 0.5% SDS. Phage clones that did not hybridize to GBSS I or GBSS II from potato but to the rice cDNA were purified further using standard techniques. By way of the in vivo excision method *E. coli* clones were obtained from positive phage clones, which contain a double-stranded pBluescript plasmid exhibiting the respective cDNA insert. After ascertaining the size and the restriction pattern of the inserts suitable clones were subjected to a sequence analysis.

EXAMPLE 2
Sequence Analysis of the cDNA Insert of Plasmid pSSSB

Figure 2:
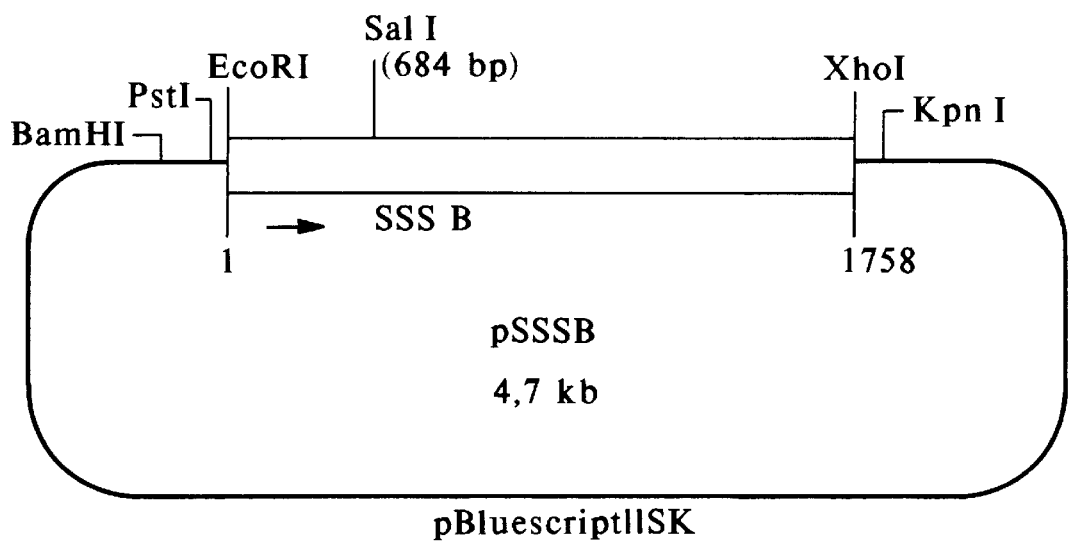
FIG. 2 shows plasmid pSSSB
The thin line corresponds to the sequence of pBluescript II SK(−). The thick line represents the cDNA encoding the SSS B isotype from *Solanum tuberosum*. The restriction sites of the insert are indicated. The cDNA insert is ligated between the EcoR I and Xho I restriction sites of the polylinker of the plasmid. The DNA sequence of the cDNA insert is indicated under SEQ ID No: 3.

Plasmid pSSSB (FIG. 2) was isolated from an *E. coli* clone obtained according to Example 1 and its cDNA insert was determined by standard techniques using the dideoxynucleotide method (Sanger et al., Proc. Natl. Acad. Sci. USA 74 (1977), 5463–5467). The insert is 1758 bp long and represents a partial cDNA. The nucleotide sequence is indicated under Seq ID No. 3. The corresponding amino acid sequence is depicted under Seq ID No. 4.

EXAMPLE 3
Isolation of the Full-length cDNA Encoding the GBSS II Isotype of the Granule-bound Starch Synthase from *Solanum tuberosum*

A leaf-specific cDNA expression library from *Solanum tuberosum* L. cv. Désirée (Koβmann et al., Planta 186 (1992), 7–12) was screened for full-length clones by standard techniques using hybridization to a 5' fragment of the cDNA insert of plasmid pGBSS II (1.9 kb). As a result, plasmid pGBSS II-VK could be isolated that contains a cDNA insert having a length of about 2.8 kb.

EXAMPLE 4
Sequence Analysis of the cDNA Insert of Plasmid pGBSS II-VK

Plasmid pGBSS II-VK was isolated from the *E. coli* clone obtained according to Example 3 and its cDNA insert was determined by standard techniques using the dideoxynucleotide method (Sanger et al., Proc. Natl. Acad. Sci. USA 74 (1977), 5463–5467). The insert is about 2.8 kb long. The nucleotide sequence is indicated under Seq ID No. 7 and comprises besides flanking regions the entire coding region for the GBSSII protein from potato. The molecular weight derived from the amino acid sequence of the protein is about 85.1 kD.

EXAMPLE 5
Isolation of the Full-length cDNA Encoding the SSS B Isotype of the Soluble Starch Synthase from *Solanum tuberosum*

A leaf-specific cDNA expression library from *Solanum tuberosum* L. cv. Désirée (Koβmann et al., Planta 186 (1992), 7–12) was screened for full-length clones by standard techniques using hybridization to a 5' fragment of the cDNA insert of plasmid pSSS B (1.6 kb). As a result, plasmid pSSS B-VK could be isolated that contains a cDNA insert having a length of about 2.3 kb.

EXAMPLE 6
Sequence Analysis of the cDNA Insert of Plasmid pSSS B-VK

Plasmid pSSS B-VK was isolated from the *E. coli* clone obtained according to Example 5 and its cDNA insert was determined by standard techniques using the dideoxynucleotide method (Sanger et al., Proc. Natl. Acad. Sci. USA 74 (1977), 5463–5467). The insert is about 2.3 kb long. The nucleotide sequence is indicated under Seq ID No. 9 and comprises besides flanking regions the entire coding region for the B isotype of the soluble starch synthase from potato. The molecular weight derived from the amino acid sequence of the protein is about 78.6 kD.

EXAMPLE 7
Identification, Isolation and Characterization of a cDNA Encoding the SSS A Isotype of the Soluble Starch Synthase from *Solanum tuberosum*

A sequence comparison between the sequences encoding soluble and granule-bound starch synthase from plants known so far (FIG. 7) showed that there are three strongly conserved regions between the various proteins (regions (I), (II) and (III) in FIG. 7).

In order for a soluble starch synthase from potato to be isolated, these three regions were selected to generate polyclonal peptide antibodies. For this purpose, three synthetic polypeptides having the following amino acid sequences were prepared:

Peptide 1: NH$_2$-PWSKTGGLGDVC-COOH (Seq ID No. 16)

Peptide 2: NH$_2$-PSRFEPCGLNQLY-COOH (Seq ID No. 17)

Peptide 3: NH$_2$-GTGGLRDTVENC-COOH (Seq ID No. 13)

These peptides were coupled to the KLH carrier (keyhole limpet homocyanin) and then used to prepare polyclonal antibodies in rabbits (Eurogentec, Seraing, Belgium).

The resulting antibodies were designated as follows:

anti-SS1 polyclonal antibody against peptide 1 anti-SS2 polyclonal antibody against peptide 2 anti-SS3 polyclonal antibody against peptide 3.

The antibodies were examined for their specificity with partially purified soluble starch synthase from potato.

The purification of the soluble starch synthases was carried out as follows:

2.5 kg potatoes were processed in 2 l buffer A. After removal of the starch by centrifugation at 1000 g for 5 min the protein extract was bound to DEAE-FastFlow column material (Pharmacia LKB)(equilibrated with buffer B). After washing the column with a five-fold column volume of buffer B, bound proteins were eluted with 300 mM NaCl in buffer B. The eluted proteins were collected fractionwise and fractions having a high starch synthase activity were pooled. The pooled fractions were desalted by chromatography on a gel filtration column (G25) which was equilibrated with buffer B. 1 volume sodium citrate, 50 mM Tris-HCl pH 7.6, 2.5 mM DTT, 2 mM EDTA were added to the eluate. The protein solution was applied to an amylose resin column (AR column) equilibrated with buffer C. The column was washed with the 20-fold column volume of buffer C. Bound proteins were then eluted with buffer B.

The fractions exhibiting high starch synthase activity were pooled and desalted by gel filtration on a G25 column.

The fractions having high starch synthase activity were applied to a MonoQ column equilibrated with buffer B. The column was washed with a five-fold column volume of buffer B. Bound proteins were eluted using a linear NaCl gradient of 0–300 mM and pooled fractionwise.

The analysis of the fractions for their starch synthase activity and for their molecular weight was carried out using various methods:

a) analysis of the fractions on a native polyacrylamide gel b) analysis of the fractions on a denaturing SDS polyacrylamide gel and subsequent silver staining c) determination of the synthase activity by incorporation of radioactively labeled ADP glucose (Amersham, UK) in newly synthesized starch d) analysis of the fractions in a Western blot.

For a Western blot analysis, 50 μg, 5 μg and 0.5 μg protein of a protein crude extract were electrophoretically separated on an SDS polyacrylamide gel along with 15 μg protein of the fractions eluted from the DEAE FastFlow column, 10 μg protein of the factions eluted from the AR column and 3 μg protein of the fractions eluted from the MonoQ column. The proteins were transferred onto a nitrocellulose membrane using the semidry electroblot method.

Proteins that were recognized by the antibodies anti-SS1, anti-SS2 or anti-SS3 were identified using the "Blotting detection kit for rabbit antibodies RPN 23" (Amersham, UK) according to the manufacturer's instructions.

Three parallel Western blot analyses were performed with the above-described polyclonal antibodies anti-SS1, anti-SS2 ana anti-SS3. It was found that the antibody anti-SS1 specifically recognized GBSS I and GBSS II and that the antibody anti-SS2 exhibited no specificity. Only antibody anti-SS3 specifically recognized in the Western blot new proteins, particularly proteins with molecular weights of 120–140 kD, besides GBSS I and GBSS II.

Antibody anti-SS3 was then used to screen a cDNA library from potato tubers for sequences encoding the soluble starch synthases from potato. For this purpose, a cDNA library prepared as described in Example 1 was used. For an analysis of the phage plaques they were transferred onto nitrocellulose filters which were previously incubated for 30–60 min in a 10 mM IPTG solution and then dried on filter paper. The transfer was carried out for 3 hrs at 37° C. The filters were then incubated for 30 min at room temperature in block reagent and washed twice for 5–10 min in TBST buffer. The filters were shaken for 1 hr at room temperature or for 16 hrs at 4° C. with the polyclonal antibody anti-SS3 in suitable dilution. Plaques expressing a protein that was recognized by antibody anti-SS3 were identified using the "Blotting detection kit for rabbit antibodies RPN 23" (Amersham, UK) according to the manufacturer's instructions.

Phage clones of the cDNA library expressing a protein that was recognized by antibody anti-SS3 were further purified using standard techniques. With the help of the in vivo excision method (Stratagene) E. coli clones were obtained from positive phage clones, which contain a double-stranded pBluescript II SK plasmid with the corresponding cDNA insert between the EcoRI and the Xho I restriction site of the polylinker. After ascertaining the size and the restriction pattern of the inserts a suitable clone was subjected to sequence analysis.

EXAMPLE 8

Sequence Analysis of the cDNA Insert of Plasmid pSSSA

Plasmid pSSA (FIG. 1) was isolated from an E. coli clone obtained according to Example 7 and its cDNA insert was determined by standard techniques using the dideoxynucleotide method (Sanger et al., Proc. Natl. Acad. Sci. USA 74 (1977), 5463–5467). The insert is 2303 bp long. The nucleotide sequence is indicated under Seq ID No. 1. The corresponding amino acid sequence is depicted under Seq ID No. 2.

A sequence analysis and a sequence comparison with known DNA sequences showed that the sequence depicted under Seq ID No. 1 is new and comprises a partial coding region encoding a protein having homology to starch synthases from various organisms. The protein encoded by this cDNA insert or by sequences hybridizing thereto is designated SSSA within this application.

This DNA sequence differs from the DNA sequence depicted under SEQ ID NO: 3 which likewise encodes a soluble starch synthase from potato and could not be isolated from a cDNA library from potato tubers using the method described in Example 1.

EXAMPLE 9

Isolation of the Full-length cDNA Encoding the SSS A Isotype of the Soluble Starch Synthase from Solanum tuberosum A leaf-specific cDNA expression library from Solanum tuberosum L. cv. Désirée (Koβmann et al., Planta 186 (1992), 7–12) was screened for full-length clones by standard techniques using hybridization to a 5' fragment of the cDNA insert of plasmid pSSSA (2.3 kb). As a result, a clone could be isolated that contains a cDNA insert that is about 1.86 kb longer in the 5' region. The cDNA insert had an entire length of about 4.16 kb.

EXAMPLE 10

Sequence Analysis of the cDNA Insert of Plasmid pSSSA-VK

Plasmid pSSSA-VK was isolated from an E. coli clone obtained according to Example 9 and its cDNA insert was determined by standard techniques using the dideoxynucleotide method (Sanger et al., Proc. Natl. Acad. Sci. USA 74 (1977), 5463–5467). The insert is about 4.16 kb long. The nucleotide sequence is indicated under Seq ID No. 11. The corresponding amino acid sequence is depicted under Seq ID No. 12. The molecular weight derived from the amino acid sequence of the SSSA protein is about 135 kD.

EXAMPLE 11

Construction of Plasmid p35S-anti-SSSA and Introduction of the Plasmid into the Genome of Potato Plants From plasmid pSSSA a DNA fragment of about 2.1 kb was isolated using the restriction endonucleases Xba I and Asp 718 which =comprises the coding region for the A isotype of the soluble starch synthase from potato, and was ligated into vector pBinAR Hyg (DSM 9505) which was digested with Xba I and Asp 718.

Figure 3:
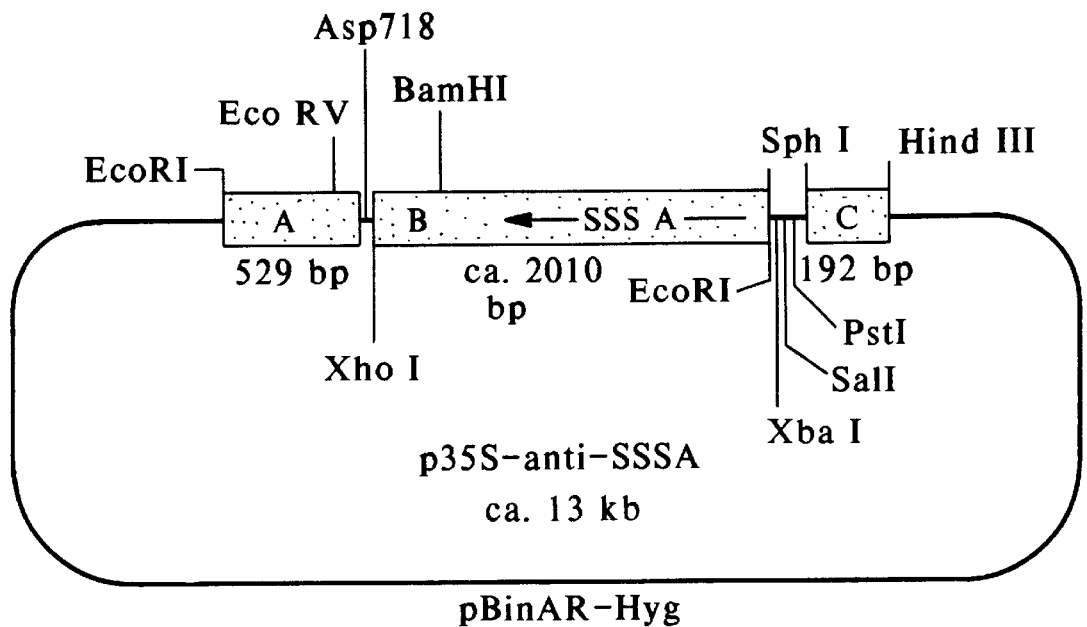
FIG. 3 shows plasmid p35S-anti-SSSA
Structure of the plasmid:
    A=fragment A: CaMV 35S promoter, nt 6909-7437 (Franck et al., Cell 21 (1980), 285–294)
    B=fragment B: cDNA from *Solanum tuberosum* encoding soluble starch synthase; SSSA isotype; Xba I/Asp718 fragment from pSSSA, about 2.1 kb orientation with respect to the promoter: antisense
    C fragment C: nt 11748-11939 of the T-DNA of the Ti plasmid pTiACH5 (Gielen et al., EMBO J. 3 (1984), 835–846)

The insertion of the cDNA fragment results in an expression cassette which is composed of fragments A, B and C as follows (FIG. 3):

Fragment A (529 bp) contains the 35S promoter of the Cauliflower mosaic virus (CaMV). The fragment comprises nucleotides 6909 to 7437 of the CaMV (Franck et al., Cell 21 (1980), 285–294).

Fragment B contains besides flanking regions the protein-encoding region of the A isotype of the soluble starch synthase from *Solanum tuberosum*. This region was isolated as Xba I/Asp 718 fragment from pSSSA as described above and was fused to the 35S promoter in pBinAR Hyg in antisense orientation.

Fragment C (192 bp) contains the polyadenylation signal of gene 3 of the T-DNA of the Ti plasmid pTiACH5 (Gielen et al., EMBO J. 3 (1984), 835–846).

The size of plasmid p35S-anti-SSSA is about 13 kb.

The plasmid was transferred to potato plants using Agrobacteria-mediated transformation as described above. Whole plants were regenerated from the transformed cells.

Figure 8A:
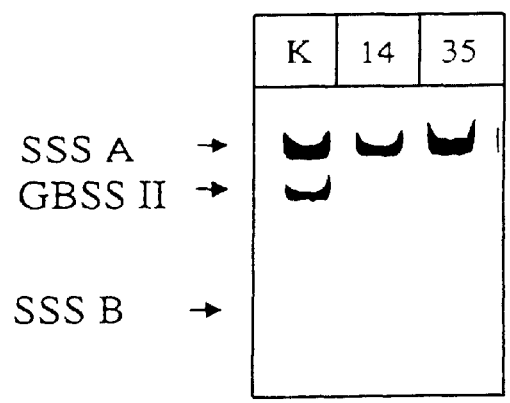
FIGS. 8A–8C show activity gels of the soluble starch synthase isotypes from tuber extracts from wild-type and starch synthase "antisense" potato plants.
    A) GBSS II "antisense" plant, lines 14 and 35, K=wild-type plant
    B) SSS A "antisense" plant, lines 25 and 39, K=wild-type plant
    C) SSS B "antisense" plant, lines 1 and 4, K=wild-type plant
50 μg each of the protein extracts were separated on a 7.5% native gel and the activities of the synthase isotypes were determined in the citrate-stimulated mixture with 0.1% amylopectin as primer. The synthesized glucans were dyed with Lugol's solution.
Figure 8B:
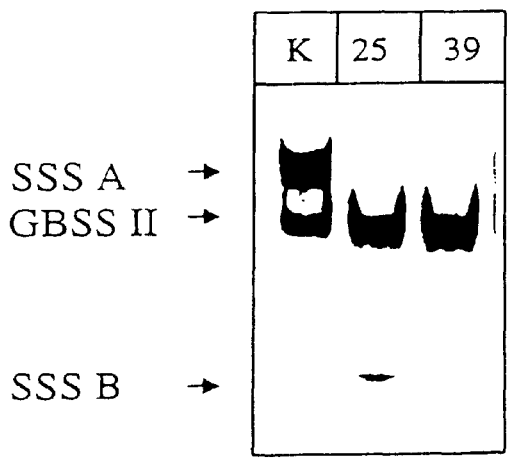
Figure 8C:
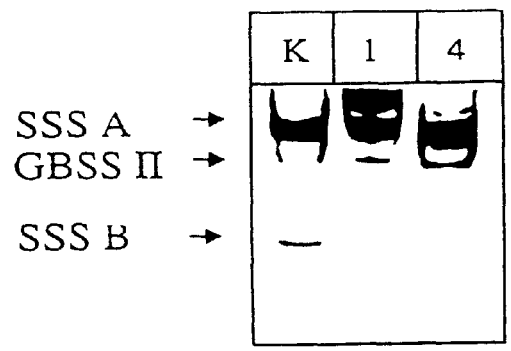

As a result of transformation the transgenic potato plants exhibited a reduced activity of A isotype of the soluble starch synthase (cf. FIG. 8).

The starch produced by these plants differs from the starch synthesized by wild-type plants in its phosphate content, in the viscosity of aqueous solutions, its pastification properties and the mean granule size. The results are depicted in Table I.

The phosphate content of the starch produced in transgenic plants is at least 30%, preferably 50%, particularly 70% higher than that of-the starch synthesized by the wild-type plants.

The final viscosity of the starch from SSS A "antisense" plants exhibits values that are at least 10%, preferably 20%, particularly 30% lower than those of the starch synthesized by wild-type plants.

The pastification temperature, the maximum viscosity and the mean granule size of the modified starch is clearly lower than that of the starch produced in wild-type plants (see Table I).

TABLE I

Characteristics of the starch from wild-type and SSS A "antisense" potato plants

|  | Wild-type | Line 25 | Line 39 |
| --- | --- | --- | --- |
| Phosphate content [nmol mg$^{-1}$ starch$^{-1}$] | 8.50 ± 0.4 | 14.61 ± 0.3 | 14.54 ± 0.2 |
| Pastification temperature [° C.] | 69.5 | 67.4 | 66.2 |
| Maximum viscosity [cP] | 4044 | 3720 | 3756 |
| Final viscosity at 50° C. [cP] | 3312 | 2904 | 2400 |
| Mean granule size [μm] | 29 | 24 | 27 |

EXAMPLE 12

Construction of Plasmid p35S-anti-SSSB and Introduction of the Plasmid into the Genome of Potato Plants From plasmid pSSSB a DNA fragment of about 1.8 kb was isolated using the restriction endonucleases Xho I and Spe I which comprises the coding region for the B isotype of the soluble starch synthase from potato, and was ligated into vector pBinAR Hyg (DSM 9505) which was digested with Sma I.

Figure 4:
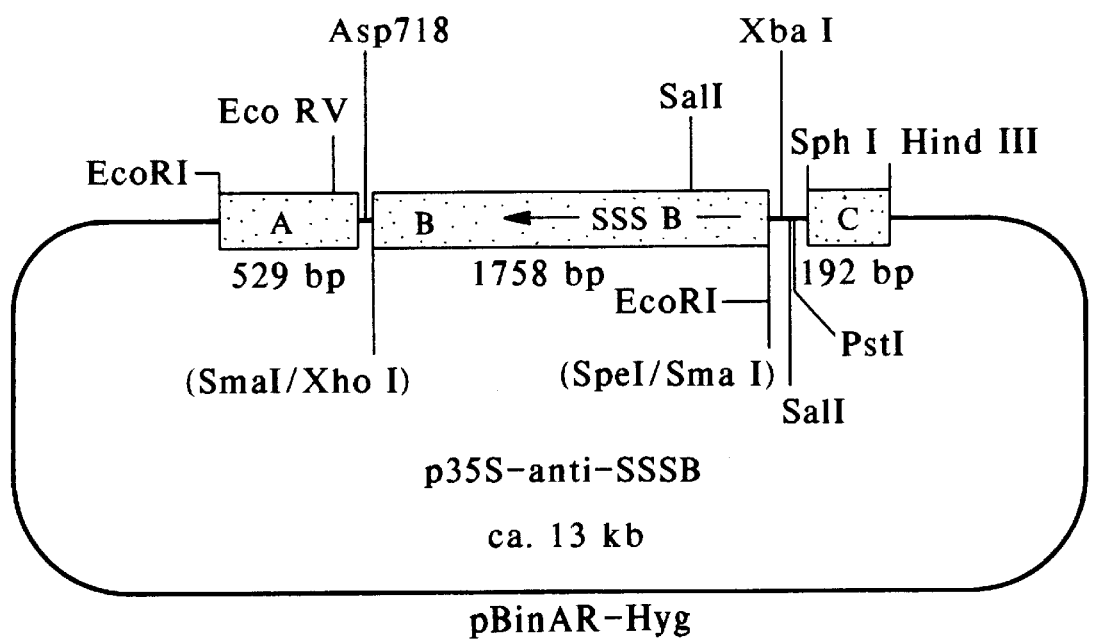
FIGS. 4A–4D show plasmid p35S-anti-SSSB
Structure of the plasmid:
    A=fragment A: CaMV 35S promoter, nt 6909-7437 (Franck et al., Cell 21 (1980), 285–294)
    B=fragment B: cDNA from *Solanum tuberosum* encoding soluble starch synthase; SSSB isotype; Xho I/Spe I fragment from pSSSB, about 1.8 kb orientation with respect to the promoter: antisense
    C=fragment C: nt 11748-11939 of the T-DNA of the Ti plasmid pTiACH5 (Gielen et al., EMBO J. 3 (1984), 835–846)

The insertion of the cDNA fragment results in an expression cassette which is composed of fragments A, B and C as follows (FIG. 4):

Fragment A (529 bp) contains the 35S promoter of the Cauliflower mosaic virus (CaMV). The fragment comprises nucleotides 6909 to 7437 of-the CaMV (Franck et al., Cell 21 (1980), 285–294).

Fragment B contains besides flanking regions the protein-encoding region of the B isotype of the soluble starch synthase from *Solanum tuberosum*. This region was isolated as Xho I/Spe I fragment from pSSSB as described above and was fused to the 35S promoter in pBinAR Hyg in antisense orientation.

Fragment C (192 bp) contains the polyadenylation signal of gene 3 of the T-DNA of the Ti plasmid pTiACH5 (Gielen et al., EMBO J. 3 (1984), 835–846).

The size of plasmid p35S-anti-SSSB is about 13 kb.

The plasmid was transferred to potato plants using Agrobacteria-mediated transformation as described above. Whole plants were regenerated from the transformed cells.

As a result of transformation the transgenic potato plants exhibited a reduced activity of B isotype of the soluble starch synthase (cf. FIG. 8).

EXAMPLE 13

Construction of Plasmid p35S-anti-GBSS I and Introduction of the Plasmid Into the Genome of Potato Plants From plasmid pGBSS II a DNA fragment of about 1.9 kb was isolated using the restriction endonucleases Asp 718 and Sma I which comprises the coding region for the GBSS II isotype of the soluble starch synthase from potato. The ends of the fragment were filled in with the T4 polymerase and the fragment was ligated into vector pBinAR Hyg (DSM 9505) which was digested with Sma I.

Figure 6:
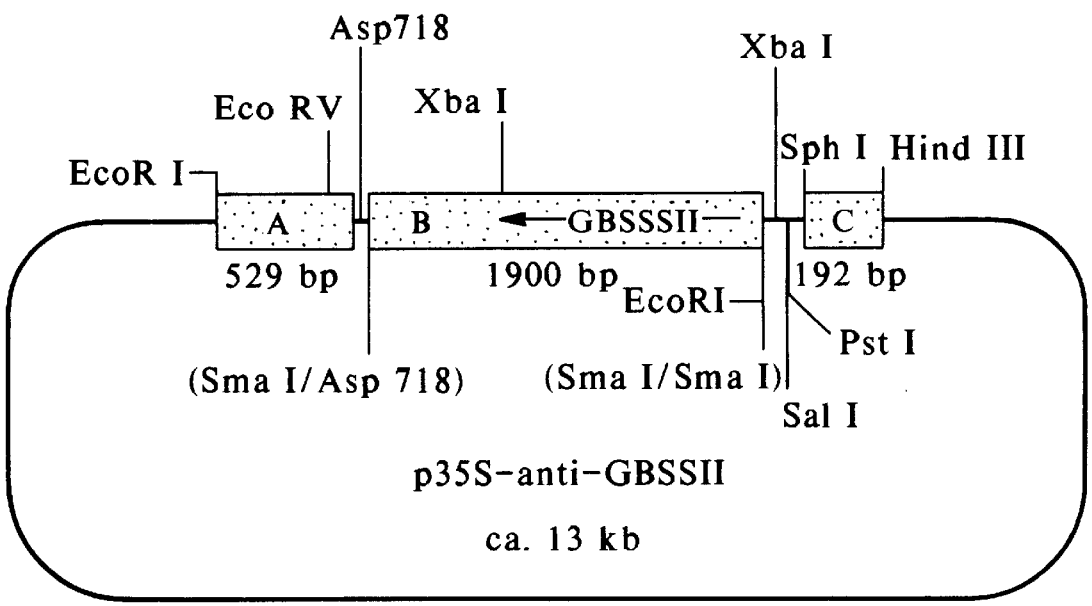
FIG. 6 shows plasmid p35S-anti-GBSSII
Structure of the plasmid:
    A=fragment A: CaMV 35S promoter, nt 6909-7437 (Franck et al., Cell 21 (1980), 285–294)
    B=fragment B: cDNA from *Solanum tuberosum* encoding granule-bound starch synthase; GBSS II isotype; Sma I/Asp 718 fragment from pGBSS II, about 1.9 kb orientation with respect to the promoter: antisense
    C=fragment C: nt 11748-11939 of the T-DNA of the Ti plasmid pTiACH5 (Gielen et al., EMBO J. 3 (1984), 835–846)

The insertion of the cDNA fragment results in an expression cassette which is composed of fragments A, B and C as follows (FIG. 6):

Fragment A (529 bp) contains the 35S promoter of the Cauliflower mosaic virus (CaMV). The fragment comprises nucleotides 6909 to 7437 of the CaMV (Franck et al., Cell 21 (1980), 285–294).

Fragment B contains besides flanking regions part of the protein-encoding region of the GBSS II isotype of the starch synthase from *Solanum tuberosum*. This region was isolated as Asp 718/Sma I fragment from pGBSS II as described above and was fused to the 35S promoter in pBinAR Hyg in antisense orientation once the ends of the fragment had been filled in.

Fragment C (192 bp) contains the polyadenylation signal of gene 3 of the T-DNA of the Ti plasmid pTiACH5 (Gielen et al., EMBO J. 3 (1984), 835–846).

The size of plasmid p35S-anti-GBSS II is about 13 kb.

The plasmid was transferred to potato plants using Agrobacteria-mediated transformation as described above. Whole plants were regenerated from the transformed cells.

As a result of transformation the transgenic potato plants exhibited a reduced activity of GBSS II isotype of the starch synthase (cf. FIG. 8).

The starch produced by these plants differs from the starch synthesized by wild-type plants in its phosphate content, in the viscosity, its pastification properties and the mean granule size. The results are depicted in Table II.

TABLE II

Characteristics of the starch from wild-type and GBSS II "antisense" potato plants

|  | Wild-type | Line 14 | Line 35 | Line 44 |
| --- | --- | --- | --- | --- |
| Phosphate content [nmol mg$^{-1}$ starch$^{-1}$] | 6.99 ± 0.19 | 4.52 ± 0.2 | 4.13 ± 0.06 | 3.76 ± 0.12 |
| Pastification temperature [° C.] | 64.1 | 62.55 | 63.25 | 63.55 |
| Maximum viscosity [cP] | 4057 | 2831 | 2453 | 2587 |

TABLE II-continued

Characteristics of the starch from wild-type and GBSS II "antisense" potato plants

|  | Wild-type | Line 14 | Line 35 | Line 44 |
|---|---|---|---|---|
| Final viscosity at 50° C. [cP] | 2849 | 2816 | 2597 | 2587 |
| Mean granule size [μm] | 37 | 32 | 31 | 32 |

The phosphate content of the starch produced in transgenic plants is at least 35%, preferably 40%, particularly 45% lower than that of the starch synthesized by the wild-type plants.

The maximum viscosity of the starch from GBSS II "antisense" plants exhibits values that are at least 30%, preferably 35%, particularly 40% lower than those of the starch synthesized by wild-type plants.

The pastification temperature and the final viscosity of the modified starch is below that of the starch produced in wild-type plants. The mean granule size of the starch produced in transgenic plants is clearly smaller than that of wild-type starch.

EXAMPLE 14

Overexpression of the Soluble Starch Syntheses SSS A and SSS B in E. coli

For an overexpression of soluble starch synthases in *E. coli* strain G6MD2 was cultivated, which is a mutant which exhibits a deletion both in the glg and in the mal operon. Hence it possesses neither the glycogen synthase (glgA), the branching enzyme (glgB) and the AGPase (glgC) nor the amylomaltase (malQ), the maltodextrin phosphorylase (malp) nor the other proteins involved in the metabolization of maltose. Therefore, mutant G6MD2 is not capable of synthesizing glycogen via the ADP glucose pathway nor α-1,4 glucans starting from maltose.

Cells of this mutant were transformed with the cDNA clones pSSSA-VK and pSSSB-VK. The *E. coli* cells expressing starch synthases were broken up after 2 hrs induction with IPTG in 50 mM Tris-HCl pH 7.6, 10% glycerol, 2 mM EDTA, 2 mM DTT and 0.4 mM PMSF by ultrasonification. As a control, cells transformed with pBluescript were used. Intact cells and cell wall material were removed by centrifugation for 10 min at 13,000 g. Then, the protein concentration of the supernatant was determined. 100 μg protein extract were added to the reaction buffer (final concentration: 50 mM tricine NaOH pH 8.5, 25 mM potassium acetate, 2 mM EDTA and 2 mM DTT, 1 mM ADP glucose). For an examination of the citrate-stimulated reaction (primer-independent) the reaction buffer additionally contained 0.5 M sodium citrate, while the primer-dependent reaction was performed in the presence of 0.02% (wt./vol.) maltooligosaccharides (Glucidex 19; 1–30 glucose units). The reaction was carried out overnight at room temperature. The synthesized glucans were detected via Lugol's solution and examined spectralphotometrically for further characterization.

Both the SSS A isotype and the SSS B isotype synthesized glucans in the primer-dependent reaction (absence of citrate). The absorption maximum of the glucan synthesized by SSS A was at 614 nm which corresponds to a glucan of about 150 glucose units. The glucan produced by SSS A absorbed at 575 nm, which points to the synthesis of short-chain glucans having a polymerization degree of about 50 glucose units.

In the primer-independent, i.e., citrate-stimulated, reaction SSS B isotype alone yielded a glucan which absorbed at 612 nm after dyeing with Lugol's solution. The SSS A isotype showed no activity in the primer-independent reaction and therefore did not synthesize any glucan.

The protein extracts from the cells transformed with pBluescript did not yield any products in any of the reactions.

What is claimed is:

1. A transgenic plant cell that expresses an RNA molecule transcribed from a DNA sequence, or a biologically active fragment of said DNA sequence, wherein said fragment is sufficient to modify starch metabolism when expressed in antisense orientation, which DNA sequence or fragment thereof is in antisense orientation with respect to an operably linked plant promoter, and which DNA sequence is selected from the group consisting of:

(1) a DNA sequence comprising:
    (a) a nucleotide sequence encoding a protein having the amino acid sequence of SEQ ID NO: 8;
    (b) the coding region of SEQ ID NO: 7; or
    (c) a nucleotide sequence that is more than 90% homologous to the nucleotide sequence of (a) or (b);
  (2) a DNA sequence comprising:
    (d) a nucleotide sequence encoding a protein having the amino acid sequence of SEQ ID NO: 10;
    (e) the coding regon of SEQ ID NO:9; or
    (f) a nucleotide sequence that is more than 90% homologous to the nucleotide sequence of (d) or (e), excluding DNA molecules encoding a starch synthase from rice; and
  (3) a DNA sequence comprising:
    (e) a nucleotide sequence encoding a protein having the amino acid sequence of SEQ ID NO: 12;

(f) the coding region of SEQ ID NO: 11; or
(g) a nucleotide sequence that is more than 90% homologous to the nucleotide sequence of (e) or (f).

2. The transgenic plant cell according to claim 1, wherein the DNA sequence encodes a protein with the biological activity of a soluble starch synthase of isotype A (SSSA), or a biologically active fragment of said protein, wherein the protein encoded by the DNA sequence is recognized by an antibody that is directed to the peptide NH2-GTGGLRDTVENC-COOH (SEQ ID NO: 13).

3. The transgenic plant cell according to claim 1, wherein the DNA sequence is more than 95% homologous to a DNA sequence selected from the group consisting of:
(a) a nucleotide sequence encoding a protein having the amino acid sequence of SEQ ID NO: 8;
(b) the coding region of SEQ ID NO: 7;
(c) a nucleotide sequence encoding a protein having the amino acid sequence of SEQ ID NO: 10;
(d) the coding regon of SEQ ID NO:9;
(e) a nucleotide sequence encoding a protein having the amino acid sequence of SEQ ID NO: 12; and
(f) the coding region of SEQ ID NO: 11.

4. The transgenic plant cell according to claim 1, wherein the DNA sequence is selected from the group consisting of:
(a) a nucleotide sequence encoding a protein having the amino acid sequence of SEQ ID NO: 8;
(b) the coding region of SEQ ID NO: 7;
(c) a nucleotide sequence encoding a protein having the amino acid sequence of SEQ ID NO: 10;
(d) the coding regon of SEQ ID NO:9;
(e) a nucleotide sequence encoding a protein having the amino acid sequence of SEQ ID NO: 12; and
(f) the coding region of SEQ ID NO: 11.

5. A transgenic plant comprising the transgenic plant cell according to any one of claims 1–4 .

6. The plant according to claim 5, wherein the plant is a starch-storing plant.

7. The plant according to claim 5, wherein the plant is a potato plant.

8. A propagation material of the plant comprising the transgenic plant cell according to any one of claims 1–4.

* * * * *

UNITED STATES PATENT AND TRADEMARK OFFICE
CERTIFICATE OF CORRECTION

PATENT NO. : 6,483,010 B1
DATED : November 19, 2002
INVENTOR(S) : Jens Kossmann et al.

It is certified that error appears in the above-identified patent and that said Letters Patent is hereby corrected as shown below:

Title page,
Item [76], Inventors, change "Eichten" to -- Fichten --.

Column 2,
Line 23, change "syntheses" to -- synthases --.

Column 14,
Line 40, change "a c construct" to -- a construct --.
Line 51, change "KoBmann" to -- Kossmann --.

Column 16,
Line 8, change "Puhler" to -- Puehler --.

Column 17,
Line 53, change "C fragment" to -- C=fragment --.

Column 25,
Line 24, change "factions" to -- fractions --.
Line 32, change "ana" to -- and --.

Column 26,
Line 2, change "pSSA" to -- pSSSA --.
Line 55, change "=comprises" to -- comprises --.

Column 88,
Line 66, change "(e)" to -- (g) --.

UNITED STATES PATENT AND TRADEMARK OFFICE
CERTIFICATE OF CORRECTION

PATENT NO. : 6,483,010 B1
DATED : November 19, 2002
INVENTOR(S) : Jens Kossmann et al.

It is certified that error appears in the above-identified patent and that said Letters Patent is hereby corrected as shown below:

Column 89,
Line 1, change "(f)" to -- (h) --.
Line 2, change "(g)" to -- (i) --.

Signed and Sealed this

Thirteenth Day of May, 2003

JAMES E. ROGAN
*Director of the United States Patent and Trademark Office*

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 2303 base pairs
      (B) TYPE: nucleotide
      (C) STRANDEDNESS: unknown
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Solanum tuberosum
      (B) STRAIN: cv Berolina
      (F) TISSUE TYPE: tuber tissue (vii) IMMEDIATE SOURCE:
      (A) LIBRARY: cDNA-library in pBluescriptSKII+
      (D) OTHER INFORMATION: CDS -continued (ix) FEATURE:
   (B) LOCATION:3..2033
   (D) OTHER INFORMATION:/function= "Polymerization of starch"
       /product= "Starch synthase"

(xi) SEQUENCE DESCRIPTION: SEQ ID NO: 1:

```
GG CAC GAG GTC AAA AAG CTT GTT AAA TCT GAG AGA ATA GAT GGT GAT        47
   His Glu Val Lys Lys Leu Val Lys Ser Glu Arg Ile Asp Gly Asp
   1               5                  10                  15

TGG TGG TAT ACA GAG GTT GTT ATT CCT GAT CAG GCA CTT TTC TTG GAT       95
Trp Trp Tyr Thr Glu Val Val Ile Pro Asp Gln Ala Leu Phe Leu Asp
                20                  25                  30

TGG GTT TTT GCT GAT GGT CCA CCC AAG CAT GCC ATT GCT TAT GAT AAC      143
Trp Val Phe Ala Asp Gly Pro Pro Lys His Ala Ile Ala Tyr Asp Asn
            35                  40                  45

AAT CAC CGC CAA GAC TTC CAT GCC ATT GTC CCC AAC CAC ATT CCG GAG      191
Asn His Arg Gln Asp Phe His Ala Ile Val Pro Asn His Ile Pro Glu
        50                  55                  60

GAA TTA TAT TGG GTT GAG GAA GAA CAT CAG ATC TTT AAG ACA CTT CAG      239
Glu Leu Tyr Trp Val Glu Glu Glu His Gln Ile Phe Lys Thr Leu Gln
    65                  70                  75

GAG GAG AGA AGG CTT AGA GAA GCG GCT ATG CGT GCT AAG GTT GAA AAA      287
Glu Glu Arg Arg Leu Arg Glu Ala Ala Met Arg Ala Lys Val Glu Lys
80                  85                  90                  95

ACA GCA CTT CTG AAA ACT GAA ACA AAG GAA AGA ACT ATG AAA TCA TTT      335
Thr Ala Leu Leu Lys Thr Glu Thr Lys Glu Arg Thr Met Lys Ser Phe
                100                 105                 110

TTA CTG TCT CAG AAG CAT GTA GTA TAT ACT GAG CCT CTT GAT ATC CAA      383
Leu Leu Ser Gln Lys His Val Val Tyr Thr Glu Pro Leu Asp Ile Gln
            115                 120                 125

GCT GGA AGC AGC GTC ACA GTT TAC TAT AAT CCC GCC AAT ACA GTA CTT      431
Ala Gly Ser Ser Val Thr Val Tyr Tyr Asn Pro Ala Asn Thr Val Leu
        130                 135                 140

AAT GGT AAA CCT GAA ATT TGG TTC AGA TGT TCA TTT AAT CGC TGG ACT      479
Asn Gly Lys Pro Glu Ile Trp Phe Arg Cys Ser Phe Asn Arg Trp Thr
    145                 150                 155

CAC CGC CTG GGT CCA TTG CCA CCT CAG AAA ATG TCG CCT GCT GAA AAT      527
His Arg Leu Gly Pro Leu Pro Pro Gln Lys Met Ser Pro Ala Glu Asn
160                 165                 170                 175

GGC ACC CAT GTC AGA GCA ACT GTG AAG GTT CCA TTG GAT GCA TAT ATG      575
Gly Thr His Val Arg Ala Thr Val Lys Val Pro Leu Asp Ala Tyr Met
                180                 185                 190

ATG GAT TTT GTA TTT TCC GAG AGA GAA GAT GGT GGG ATT TTT GAC AAT      623
Met Asp Phe Val Phe Ser Glu Arg Glu Asp Gly Gly Ile Phe Asp Asn
            195                 200                 205

AAG AGC GGA ATG GAC TAT CAC ATA CCT GTG TTT GGA GGA GTC GCT AAA      671
Lys Ser Gly Met Asp Tyr His Ile Pro Val Phe Gly Gly Val Ala Lys
        210                 215                 220

GAA CCT CCA ATG CAT ATT GTC CAT ATT GCT GTC GAA ATG GCA CCA ATT      719
Glu Pro Pro Met His Ile Val His Ile Ala Val Glu Met Ala Pro Ile
225                 230                 235

GCA AAG GTG GGA GGC CTT GGT GAT GTT GTT ACT AGT CTT TCC CGT GCT      767
Ala Lys Val Gly Gly Leu Gly Asp Val Val Thr Ser Leu Ser Arg Ala
240                 245                 250                 255

GTT CAA GAT TTA AAC CAT AAT GTG GAT ATT ATC TTA CCT AAG TAT GAC      815
Val Gln Asp Leu Asn His Asn Val Asp Ile Ile Leu Pro Lys Tyr Asp
                260                 265                 270

TGT TTG AAG ATG AAT AAT GTG AAG GAC TTT CGG TTT CAC AAA AAC TAC      863
Cys Leu Lys Met Asn Asn Val Lys Asp Phe Arg Phe His Lys Asn Tyr
            275                 280                 285
```

```
TTT TGG GGT GGG ACT GAA ATA AAA GTA TGG TTT GGA AAG GTG GAA GGT        911
Phe Trp Gly Gly Thr Glu Ile Lys Val Trp Phe Gly Lys Val Glu Gly
        290                 295                 300

CTC TCG GTC TAT TTT TTG GAG CCT CAA AAC GGG TTA TTT TCG AAA GGG        959
Leu Ser Val Tyr Phe Leu Glu Pro Gln Asn Gly Leu Phe Ser Lys Gly
    305                 310                 315

TGC GTC TAT GGT TGT AGC AAT GAT GGT GAA CGA TTT GGT TTC TTC TGT       1007
Cys Val Tyr Gly Cys Ser Asn Asp Gly Glu Arg Phe Gly Phe Phe Cys
320                 325                 330                 335

CAC GCG GCT TTG GAG TTT CTT CTG CAA GGT GGA TTT AGT CCG GAT ATC       1055
His Ala Ala Leu Glu Phe Leu Leu Gln Gly Gly Phe Ser Pro Asp Ile
                340                 345                 350

ATT CAT TGC CAT GAT TGG TCT AGT GCT CCT GTT GCT TGG CTC TTT AAG       1103
Ile His Cys His Asp Trp Ser Ser Ala Pro Val Ala Trp Leu Phe Lys
            355                 360                 365

GAA CAA TAT ACA CAC TAT GGT CTA AGC AAA TCT CGT ATA GTC TTC ACG       1151
Glu Gln Tyr Thr His Tyr Gly Leu Ser Lys Ser Arg Ile Val Phe Thr
        370                 375                 380

ATA CAT AAT CTT GAA TTT GGG GCA GAT CTC ATT GGG AGA GCA ATG ACT       1199
Ile His Asn Leu Glu Phe Gly Ala Asp Leu Ile Gly Arg Ala Met Thr
    385                 390                 395

AAC GCA GAC AAA GCT ACA ACA GTT TCA CCA ACT TAC TCA CAG GAG GTG       1247
Asn Ala Asp Lys Ala Thr Thr Val Ser Pro Thr Tyr Ser Gln Glu Val
400                 405                 410                 415

TCT GGA AAC CCT GTA ATT GCG CCT CAC CTT CAC AAG TTC CAT GGT ATA       1295
Ser Gly Asn Pro Val Ile Ala Pro His Leu His Lys Phe His Gly Ile
                420                 425                 430

GTG AAT GGG ATT GAC CCA GAT ATT TGG GAT CCT TTA AAC GAT AAG TTC       1343
Val Asn Gly Ile Asp Pro Asp Ile Trp Asp Pro Leu Asn Asp Lys Phe
            435                 440                 445

ATT CCG ATT CCG TAC ACC TCA GAA AAC GTT GTT GAA GGC AAA ACA GCA       1391
Ile Pro Ile Pro Tyr Thr Ser Glu Asn Val Val Glu Gly Lys Thr Ala
        450                 455                 460

GCC AAG GAA GCT TTG CAG CGA AAA CTT GGA CTG AAA CAG GCT GAC CTT       1439
Ala Lys Glu Ala Leu Gln Arg Lys Leu Gly Leu Lys Gln Ala Asp Leu
    465                 470                 475

CCT TTG GTA GGA ATT ATC ACC CGC TTA ACT CAC CAG AAA GGA ATC CAC       1487
Pro Leu Val Gly Ile Ile Thr Arg Leu Thr His Gln Lys Gly Ile His
480                 485                 490                 495

CTC ATT AAA CAT GCT ATT TGG CGC ACC TTG GAA CGG AAC GGA CAG GTA       1535
Leu Ile Lys His Ala Ile Trp Arg Thr Leu Glu Arg Asn Gly Gln Val
                500                 505                 510

GTC TTG CTT GGT TCT GCT CCT GAT CCT AGG GTA CAA AAC GAT TTT GTT       1583
Val Leu Leu Gly Ser Ala Pro Asp Pro Arg Val Gln Asn Asp Phe Val
            515                 520                 525

AAT TTG GCA AAT CAA TTG CAC TCC AAA TAT AAT GAC CGC GCA CGA CTC       1631
Asn Leu Ala Asn Gln Leu His Ser Lys Tyr Asn Asp Arg Ala Arg Leu
        530                 535                 540

TGT CTA ACA TAT GAC GAG CCA CTT TCT CAC CTG ATA TAT GCT GGT GCT       1679
Cys Leu Thr Tyr Asp Glu Pro Leu Ser His Leu Ile Tyr Ala Gly Ala
    545                 550                 555

GAT TTT ATT CTA GTT CCT TCA ATA TTT GAG CCA TGT GGA CTA ACA CAA       1727
Asp Phe Ile Leu Val Pro Ser Ile Phe Glu Pro Cys Gly Leu Thr Gln
560                 565                 570                 575

CTT ACC GCT ATG AGA TAT GGT TCA ATT CCA GTC GTG CGT AAA ACT GGA       1775
Leu Thr Ala Met Arg Tyr Gly Ser Ile Pro Val Val Arg Lys Thr Gly
                580                 585                 590

GGA CTT TAT GAT ACT GTA TTT GAT GTT GAC CAT GAC AAA GAG AGA GCA       1823
Gly Leu Tyr Asp Thr Val Phe Asp Val Asp His Asp Lys Glu Arg Ala
            595                 600                 605
```

```
CAA CAG TGT GGT CTT GAA CCA AAT GGA TTC AGC TTT GAT GGA GCA GAT      1871
Gln Gln Cys Gly Leu Glu Pro Asn Gly Phe Ser Phe Asp Gly Ala Asp
        610                 615                 620

GCT GGC GGA GTT GAT TAT GCT CTG AAT AGA GCT CTC TCT GCT TGG TAC      1919
Ala Gly Gly Val Asp Tyr Ala Leu Asn Arg Ala Leu Ser Ala Trp Tyr
            625                 630                 635

GAT GGT CGG GAT TGG TTC AAC TCT TTA TGC AAG CAG GTC ATG GAA CAA      1967
Asp Gly Arg Asp Trp Phe Asn Ser Leu Cys Lys Gln Val Met Glu Gln
640                 645                 650                 655

GAT TGG TCT TGG AAC CGA CCT GCT CTT GAT TAT TTG GAG CTT TAC CAT      2015
Asp Trp Ser Trp Asn Arg Pro Ala Leu Asp Tyr Leu Glu Leu Tyr His
                660                 665                 670

GCT GCT AGA AAG TTA GAA TAGTTAGTTT GTGAGATGCT AGCAGAAAAA             2063
Ala Ala Arg Lys Leu Glu
                675

TTCACGAGAT CTGCAATCTG TACAGGTTCA GTGTTTGCGT CTGGACAGCT TTTTATTT      2123

TATATCAAAG TATAAATCAA GTCTACACTG AGATCAATAG CAGACAGTCC TCAGTTCA      2183

TCATTTTTTG TGCAACATAT GAAAGAGCTT AGCCTCTAAT AATGTAGTCA TTGATGAT      2243

TTTGTTTTGG GAAGAAATGA GAAATCAAAG GATGCAAAAT ACTCTGAAAA AAAAAAAA      2303

(2) INFORMATION FOR SEQ ID NO: 2:

(i) SEQUENCE CHARACTERISTICS:
        (A) LENGTH: 677 amino acids
        (B) TYPE: amino acid
        (D) TOPOLOGY: linear (ii) MOLECULE TYPE: protein (xi) SEQUENCE DESCRIPTION: SEQ ID NO: 2:

His Glu Val Lys Lys Leu Val Lys Ser Glu Arg Ile Asp Gly Asp Trp
1               5                   10                  15

Trp Tyr Thr Glu Val Val Ile Pro Asp Gln Ala Leu Phe Leu Asp Trp
            20                  25                  30

Val Phe Ala Asp Gly Pro Pro Lys His Ala Ile Ala Tyr Asp Asn Asn
        35                  40                  45

His Arg Gln Asp Phe His Ala Ile Val Pro Asn His Ile Pro Glu Glu
    50                  55                  60

Leu Tyr Trp Val Glu Glu His Gln Ile Phe Lys Thr Leu Gln Glu
65                  70                  75                  80

Glu Arg Arg Leu Arg Glu Ala Ala Met Arg Ala Lys Val Glu Lys Thr
                85                  90                  95

Ala Leu Leu Lys Thr Glu Thr Lys Glu Arg Thr Met Lys Ser Phe Leu
            100                 105                 110

Leu Ser Gln Lys His Val Val Tyr Thr Glu Pro Leu Asp Ile Gln Ala
        115                 120                 125

Gly Ser Ser Val Thr Val Tyr Tyr Asn Pro Ala Asn Thr Val Leu Asn
    130                 135                 140

Gly Lys Pro Glu Ile Trp Phe Arg Cys Ser Phe Asn Arg Trp Thr His
145                 150                 155                 160

Arg Leu Gly Pro Leu Pro Pro Gln Lys Met Ser Pro Ala Glu Asn Gly
                165                 170                 175

Thr His Val Arg Ala Thr Val Lys Val Pro Leu Asp Ala Tyr Met Met
            180                 185                 190

Asp Phe Val Phe Ser Glu Arg Glu Asp Gly Gly Ile Phe Asp Asn Lys
        195                 200                 205
```

-continued

```
Ser Gly Met Asp Tyr His Ile Pro Val Phe Gly Gly Val Ala Lys Glu
    210                 215                 220
Pro Pro Met His Ile Val His Ile Ala Val Glu Met Ala Pro Ile Ala
225                 230                 235                 240
Lys Val Gly Gly Leu Gly Asp Val Val Thr Ser Leu Ser Arg Ala Val
                245                 250                 255
Gln Asp Leu Asn His Asn Val Asp Ile Ile Leu Pro Lys Tyr Asp Cys
            260                 265                 270
Leu Lys Met Asn Asn Val Lys Asp Phe Arg Phe His Lys Asn Tyr Phe
        275                 280                 285
Trp Gly Gly Thr Glu Ile Lys Val Trp Phe Gly Lys Val Glu Gly Leu
    290                 295                 300
Ser Val Tyr Phe Leu Glu Pro Gln Asn Gly Leu Phe Ser Lys Gly Cys
305                 310                 315                 320
Val Tyr Gly Cys Ser Asn Asp Gly Glu Arg Phe Gly Phe Phe Cys His
                325                 330                 335
Ala Ala Leu Glu Phe Leu Leu Gln Gly Gly Phe Ser Pro Asp Ile Ile
            340                 345                 350
His Cys His Asp Trp Ser Ser Ala Pro Val Ala Trp Leu Phe Lys Glu
        355                 360                 365
Gln Tyr Thr His Tyr Gly Leu Ser Lys Ser Arg Ile Val Phe Thr Ile
    370                 375                 380
His Asn Leu Glu Phe Gly Ala Asp Leu Ile Gly Arg Ala Met Thr Asn
385                 390                 395                 400
Ala Asp Lys Ala Thr Thr Val Ser Pro Thr Tyr Ser Gln Glu Val Ser
                405                 410                 415
Gly Asn Pro Val Ile Ala Pro His Leu His Lys Phe His Gly Ile Val
            420                 425                 430
Asn Gly Ile Asp Pro Asp Ile Trp Asp Pro Leu Asn Asp Lys Phe Ile
        435                 440                 445
Pro Ile Pro Tyr Thr Ser Glu Asn Val Val Glu Gly Lys Thr Ala Ala
    450                 455                 460
Lys Glu Ala Leu Gln Arg Lys Leu Gly Leu Lys Gln Ala Asp Leu Pro
465                 470                 475                 480
Leu Val Gly Ile Ile Thr Arg Leu Thr His Gln Lys Gly Ile His Leu
                485                 490                 495
Ile Lys His Ala Ile Trp Arg Thr Leu Glu Arg Asn Gly Gln Val Val
            500                 505                 510
Leu Leu Gly Ser Ala Pro Asp Pro Arg Val Gln Asn Asp Phe Val Asn
        515                 520                 525
Leu Ala Asn Gln Leu His Ser Lys Tyr Asn Asp Arg Ala Arg Leu Cys
    530                 535                 540
Leu Thr Tyr Asp Glu Pro Leu Ser His Leu Ile Tyr Ala Gly Ala Asp
545                 550                 555                 560
Phe Ile Leu Val Pro Ser Ile Phe Glu Pro Cys Gly Leu Thr Gln Leu
                565                 570                 575
Thr Ala Met Arg Tyr Gly Ser Ile Pro Val Val Arg Lys Thr Gly Gly
            580                 585                 590
Leu Tyr Asp Thr Val Phe Asp Val Asp His Asp Lys Glu Arg Ala Gln
        595                 600                 605
Gln Cys Gly Leu Glu Pro Asn Gly Phe Ser Phe Asp Gly Ala Asp Ala
    610                 615                 620
```

```
Gly Gly Val Asp Tyr Ala Leu Asn Arg Ala Leu Ser Ala Trp Tyr Asp
625                 630                 635                 640

Gly Arg Asp Trp Phe Asn Ser Leu Cys Lys Gln Val Met Glu Gln Asp
                645                 650                 655

Trp Ser Trp Asn Arg Pro Ala Leu Asp Tyr Leu Glu Leu Tyr His Ala
                660                 665                 670

Ala Arg Lys Leu Glu
        675
```

(2) INFORMATION FOR SEQ ID NO: 3:

(i) SEQUENCE CHARACTERISTICS:
        (A) LENGTH: 1758 base pairs
        (B) TYPE: nucleotide
        (C) STRANDEDNESS: unknown
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Solanum tuberosum
        (B) STRAIN: cv. Berolina
        (F) TISSUE TYPE: tuber tissue (vii) IMMEDIATE SOURCE:
        (A) LIBRARY: cDNA-library in pBluescriptSKII+
        (D) OTHER INFORMATION: CDS (ix) FEATURE:
        (B) LOCATION:1..1377
        (D) OTHER INFORMATION:/function= "Polymerization of
            starch"
            /product= "Starch synthase"

(xi) SEQUENCE DESCRIPTION: SEQ ID NO: 3:

```
GGC ACG AGC AAT GCT GTT GAC CTT GAT GTG CGG GCC ACT GTC CAT TGC        48
Gly Thr Ser Asn Ala Val Asp Leu Asp Val Arg Ala Thr Val His Cys
  1               5                  10                  15

TTT GGT GAT GCA CAG GAA GTA GCC TTC TAC CAT GAA TAC AGG GCA GGT        96
Phe Gly Asp Ala Gln Glu Val Ala Phe Tyr His Glu Tyr Arg Ala Gly
                 20                  25                  30

GTT GAT TGG GTA TTT GTG GAC CAC TCT TCT TAC CGC AGA CCT GGA ACG       144
Val Asp Trp Val Phe Val Asp His Ser Ser Tyr Arg Arg Pro Gly Thr
         35                  40                  45

CCA TAT GGT GAT ATT TAT GGT GCA TTT GGT GAT AAT CAG TTT CGC TTC       192
Pro Tyr Gly Asp Ile Tyr Gly Ala Phe Gly Asp Asn Gln Phe Arg Phe
 50                  55                  60

ACT TTG CTT TCT CAC GCA GCA TGT GAA GCG CCA TTG GTT CTT CCA CTG       240
Thr Leu Leu Ser His Ala Ala Cys Glu Ala Pro Leu Val Leu Pro Leu
 65                  70                  75                  80

GGA GGG TTC ACT TAT GGA GAG AAG TGC TTG TTT CTC GCT AAT GAT TGC       288
Gly Gly Phe Thr Tyr Gly Glu Lys Cys Leu Phe Leu Ala Asn Asp Cys
                 85                  90                  95

AAC GCT GCC TTG GTT CCT TTA CTT TTA GCG GCC AAG TAT CGT CCT TAT       336
Asn Ala Ala Leu Val Pro Leu Leu Leu Ala Ala Lys Tyr Arg Pro Tyr
                100                 105                 110

GGT GTT TAC AAG GAT GCT CGT AGT ATT GTC GCA ATA CAC AAC ATT GCA       384
Gly Val Tyr Lys Asp Ala Arg Ser Ile Val Ala Ile His Asn Ile Ala
         115                 120                 125

CAT CAG GGA GTG GAG CCT GCA GTA ACC TAC AAT AAT TTG GGT TTG CCT       432
His Gln Gly Val Glu Pro Ala Val Thr Tyr Asn Asn Leu Gly Leu Pro
130                 135                 140
```

```
CCA CAA TGG TAT GGA GCA GTT GAA TGG ATA TTT CCC ACA TGG GCA AGG         480
Pro Gln Trp Tyr Gly Ala Val Glu Trp Ile Phe Pro Thr Trp Ala Arg
145                 150                 155                 160

GCG CAT GCG CTT GAC ACT GGT GAA ACA GTG AAC GTT TTG AAA GGG GCA         528
Ala His Ala Leu Asp Thr Gly Glu Thr Val Asn Val Leu Lys Gly Ala
            165                 170                 175

ATA GCA GTT GCT GAT CGG ATA CTG ACA GTT AGC CAG GGA TAC TCA TGG         576
Ile Ala Val Ala Asp Arg Ile Leu Thr Val Ser Gln Gly Tyr Ser Trp
                180                 185                 190

GAA ATA ACA ACT CCT GAA GGG GGA TAT GGG CTA CAT GAG CTG TTG AGC         624
Glu Ile Thr Thr Pro Glu Gly Gly Tyr Gly Leu His Glu Leu Leu Ser
            195                 200                 205

AGT AGA CAG TCT GTT CTT AAT GGA ATT ACT AAT GGA ATA GAT GTT AAT         672
Ser Arg Gln Ser Val Leu Asn Gly Ile Thr Asn Gly Ile Asp Val Asn
210                 215                 220

GAT TGG AAC CCG TCG ACA GAT GAG CAT ATC GCT TCG CAT TAC TCC ATC         720
Asp Trp Asn Pro Ser Thr Asp Glu His Ile Ala Ser His Tyr Ser Ile
225                 230                 235                 240

AAT GAC CTC TCC CCC CCT GGA AAG GTT CAG TGC AAG ACT GAT CTG CAA         768
Asn Asp Leu Ser Pro Pro Gly Lys Val Gln Cys Lys Thr Asp Leu Gln
                245                 250                 255

AAG GAA CTG GGC CTT CCA ATT CGA CCC GAT TGT CCA CTG ATT GGA TTT         816
Lys Glu Leu Gly Leu Pro Ile Arg Pro Asp Cys Pro Leu Ile Gly Phe
            260                 265                 270

ATT GGA AGG CTG GAC TAC CAG AAA GGT GTT GAC ATA ATC CTG TCA GCA         864
Ile Gly Arg Leu Asp Tyr Gln Lys Gly Val Asp Ile Ile Leu Ser Ala
                275                 280                 285

ATT CCA GAA CTT ATG CAG AAT GAT GTC CAA GTT GTA ATG CTT GGA TCT         912
Ile Pro Glu Leu Met Gln Asn Asp Val Gln Val Val Met Leu Gly Ser
            290                 295                 300

GGT GAG AAA CAA TAT GAA GAC TGG ATG AGA CAT ACA GAA AAT CTT TTT         960
Gly Glu Lys Gln Tyr Glu Asp Trp Met Arg His Thr Glu Asn Leu Phe
305                 310                 315                 320

AAA GAC AAA TTT CGT GCT TGG GTT GGA TTT AAT GTT CCA GTT TCT CAT        1008
Lys Asp Lys Phe Arg Ala Trp Val Gly Phe Asn Val Pro Val Ser His
                325                 330                 335

AGG ATA ACA GCA GGA TGC GAC ATA CTA TTG ATG CCC TCA AGA TTC GAA        1056
Arg Ile Thr Ala Gly Cys Asp Ile Leu Leu Met Pro Ser Arg Phe Glu
            340                 345                 350

CCG TGT GGC TTA AAC CAA TTG TAT GCA ATG AGA TAT GGC ACC ATA CCT        1104
Pro Cys Gly Leu Asn Gln Leu Tyr Ala Met Arg Tyr Gly Thr Ile Pro
                355                 360                 365

ATT GTT CAT AGC ACG GGG GGC CTA AGA GAC ACA GTG AAG GAT TTT AAT        1152
Ile Val His Ser Thr Gly Gly Leu Arg Asp Thr Val Lys Asp Phe Asn
            370                 375                 380

CCA TAT GCT CAA GAA GGA AAA GGT GAA GGT ACC GGG TGG ACA TTT TCT        1200
Pro Tyr Ala Gln Glu Gly Lys Gly Glu Gly Thr Gly Trp Thr Phe Ser
385                 390                 395                 400

CCT CTA ACG AGT GAA AAG TTG TTT GAT ACA CTG AAG CTG GCG ATC AGG        1248
Pro Leu Thr Ser Glu Lys Leu Phe Asp Thr Leu Lys Leu Ala Ile Arg
                405                 410                 415

ACT TAT ACA GAA CAT AAG TCA TCT TGG GAG GGA TTG ATG AAG AGA GGT        1296
Thr Tyr Thr Glu His Lys Ser Ser Trp Glu Gly Leu Met Lys Arg Gly
            420                 425                 430

ATG GGA AGG GAC TAT TCC TGG GAA AAT GCA GCC ATT CAA TAT GAG CAA        1344
Met Gly Arg Asp Tyr Ser Trp Glu Asn Ala Ala Ile Gln Tyr Glu Gln
                435                 440                 445

GTT TTC ACC TGG GCC TTT ATA GAT CCT CCA TAT GTCAGATGAT TTATCAAG        1397
Val Phe Thr Trp Ala Phe Ile Asp Pro Pro Tyr
450                 455
```

-continued

```
AGATTGCAAA CGGGATACAT CATTAAACTA TACGCAGAGC TTTTGGTGCT ATTAGCTA     1457

GTCATTGGGC GCGGAATGTT TGTGGTTCTT TCTGATTCAG AGAGATCAAG TTAGTTCC     1517

AGACATGTAG CCTGCCCCTG TCTGTGATGA AGTAAAACTA CAAAGGCAAT TAGAAACC     1577

CCAACAACTG CCTCCTTTGG GAGAAGAGTG GAAATATGTA AAAAGAATT  TTGAGTTT     1637

TGTCAATTGA ATTAATTATT CTCATTTTTA AAAAAAACAT CTCATCTCAT ACAATATA     1697

AAATTGATCA TGATTGATGC CCCCTAAAAA AAAAAAAAAA AAAAAAAAAA AAAAAAA      1757

A                                                                  1758
```

(2) INFORMATION FOR SEQ ID NO: 4:

(i) SEQUENCE CHARACTERISTICS:
        (A) LENGTH: 459 amino acids
        (B) TYPE: amino acid
        (D) TOPOLOGY: linear (ii) MOLECULE TYPE: protein (xi) SEQUENCE DESCRIPTION: SEQ ID NO: 4:

```
Gly Thr Ser Asn Ala Val Asp Leu Asp Val Arg Ala Thr Val His Cys
 1               5                  10                  15

Phe Gly Asp Ala Gln Glu Val Ala Phe Tyr His Glu Tyr Arg Ala Gly
                20                  25                  30

Val Asp Trp Val Phe Val Asp His Ser Ser Tyr Arg Arg Pro Gly Thr
            35                  40                  45

Pro Tyr Gly Asp Ile Tyr Gly Ala Phe Gly Asp Asn Gln Phe Arg Phe
 50                  55                  60

Thr Leu Leu Ser His Ala Ala Cys Glu Ala Pro Leu Val Leu Pro Leu
 65                  70                  75                  80

Gly Gly Phe Thr Tyr Gly Glu Lys Cys Leu Phe Leu Ala Asn Asp Cys
                85                  90                  95

Asn Ala Ala Leu Val Pro Leu Leu Ala Ala Lys Tyr Arg Pro Tyr
                100                 105                 110

Gly Val Tyr Lys Asp Ala Arg Ser Ile Val Ala Ile His Asn Ile Ala
            115                 120                 125

His Gln Gly Val Glu Pro Ala Val Thr Tyr Asn Asn Leu Gly Leu Pro
130                 135                 140

Pro Gln Trp Tyr Gly Ala Val Glu Trp Ile Phe Pro Thr Trp Ala Arg
145                 150                 155                 160

Ala His Ala Leu Asp Thr Gly Glu Thr Val Asn Val Leu Lys Gly Ala
                165                 170                 175

Ile Ala Val Ala Asp Arg Ile Leu Thr Val Ser Gln Gly Tyr Ser Trp
            180                 185                 190

Glu Ile Thr Thr Pro Glu Gly Gly Tyr Gly Leu His Glu Leu Leu Ser
        195                 200                 205

Ser Arg Gln Ser Val Leu Asn Gly Ile Thr Asn Gly Ile Asp Val Asn
210                 215                 220

Asp Trp Asn Pro Ser Thr Asp Glu His Ile Ala Ser His Tyr Ser Ile
225                 230                 235                 240

Asn Asp Leu Ser Pro Pro Gly Lys Val Gln Cys Lys Thr Asp Leu Gln
                245                 250                 255

Lys Glu Leu Gly Leu Pro Ile Arg Pro Asp Cys Pro Leu Ile Gly Phe
            260                 265                 270

Ile Gly Arg Leu Asp Tyr Gln Lys Gly Val Asp Ile Ile Leu Ser Ala
        275                 280                 285
```

-continued

```
Ile Pro Glu Leu Met Gln Asn Asp Val Gln Val Val Met Leu Gly Ser
    290                 295                 300

Gly Glu Lys Gln Tyr Glu Asp Trp Met Arg His Thr Glu Asn Leu Phe
305                 310                 315                 320

Lys Asp Lys Phe Arg Ala Trp Val Gly Phe Asn Val Pro Val Ser His
                325                 330                 335

Arg Ile Thr Ala Gly Cys Asp Ile Leu Leu Met Pro Ser Arg Phe Glu
            340                 345                 350

Pro Cys Gly Leu Asn Gln Leu Tyr Ala Met Arg Tyr Gly Thr Ile Pro
        355                 360                 365

Ile Val His Ser Thr Gly Gly Leu Arg Asp Thr Val Lys Asp Phe Asn
    370                 375                 380

Pro Tyr Ala Gln Glu Gly Lys Gly Glu Gly Thr Gly Trp Thr Phe Ser
385                 390                 395                 400

Pro Leu Thr Ser Glu Lys Leu Phe Asp Thr Leu Lys Leu Ala Ile Arg
                405                 410                 415

Thr Tyr Thr Glu His Lys Ser Ser Trp Glu Gly Leu Met Lys Arg Gly
            420                 425                 430

Met Gly Arg Asp Tyr Ser Trp Glu Asn Ala Ala Ile Gln Tyr Glu Gln
        435                 440                 445

Val Phe Thr Trp Ala Phe Ile Asp Pro Pro Tyr
    450                 455
```

(2) INFORMATION FOR SEQ ID NO: 5:

(i) SEQUENCE CHARACTERISTICS:
        (A) LENGTH: 1926 base pairs
        (B) TYPE: nucleotide
        (C) STRANDEDNESS: unknown
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Solanum tuberosum
        (B) STRAIN: cv. Berolina
        (F) TISSUE TYPE: tuber tissue (vii) IMMEDIATE SOURCE:
        (A) LIBRARY: cDNA-library in pBluescriptSK+
        (D) OTHER INFORMATION: CDS (ix) FEATURE:
        (B) LOCATION:2..1675
        (D) OTHER INFORMATION:/function= "Polymerization of
            starch"
            /product= "Starch synthase"

(xi) SEQUENCE DESCRIPTION: SEQ ID NO: 5:

```
C GGC ACG AGC AAA AGT TTA GTA GAT GTT CCT GGA AAG AAG ATC CAG         46
  Gly Thr Ser Lys Ser Leu Val Asp Val Pro Gly Lys Lys Ile Gln
    1               5                   10                  15

TCT TAT ATG CCT TCA TTA CGT AAA GAA TCC TCA GCA TCC CAT GTG GAA       94
Ser Tyr Met Pro Ser Leu Arg Lys Glu Ser Ser Ala Ser His Val Glu
            20                  25                  30

CAG AGG AAT GAA AAT CTT GAA GGA TCA AGT GCT GAG GCA AAC GAA GAG      142
Gln Arg Asn Glu Asn Leu Glu Gly Ser Ser Ala Glu Ala Asn Glu Glu
        35                  40                  45
```

```
ACT GAA GAT CCT GTG AAT ATA GAT GAG AAA CCC CCT CCA TTG GCA GGA         190
Thr Glu Asp Pro Val Asn Ile Asp Glu Lys Pro Pro Pro Leu Ala Gly
         50                  55                  60

ACA AAT GTT ATG AAC ATT ATT TTG GTG GCT TCA GAA TGC GCT CCA TGG         238
Thr Asn Val Met Asn Ile Ile Leu Val Ala Ser Glu Cys Ala Pro Trp
 65                  70                  75

TCT AAA ACA GGT GGG CTT GGA GAT GTT GCT GGA GCA TTA CCC AAA GCT         286
Ser Lys Thr Gly Gly Leu Gly Asp Val Ala Gly Ala Leu Pro Lys Ala
 80                  85                  90                  95

TTG GCT CGA CGT GGC CAC AGA GTT ATG GTT GTG GCA CCT CGT TAT GAC         334
Leu Ala Arg Arg Gly His Arg Val Met Val Val Ala Pro Arg Tyr Asp
                    100                 105                 110

AAC TAT CCT GAA CCT CAA GAT TCT GGT GTA AGA AAA ATT TAT AAA GTT         382
Asn Tyr Pro Glu Pro Gln Asp Ser Gly Val Arg Lys Ile Tyr Lys Val
            115                 120                 125

GAT GGT CAG GAT GTG GAA GTG ACT TAC TTC CAA GCT TTT ATT GAT GGT         430
Asp Gly Gln Asp Val Glu Val Thr Tyr Phe Gln Ala Phe Ile Asp Gly
        130                 135                 140

GTG GAT TTT GTT TTC ATT GAC AGT CAT ATG TTT AGA CAC ATT GGG AAC         478
Val Asp Phe Val Phe Ile Asp Ser His Met Phe Arg His Ile Gly Asn
145                 150                 155

AAC ATT TAC GGA GGG AAC CGT GTG GAT ATT TTA AAA CGC ATG GTT TTA         526
Asn Ile Tyr Gly Gly Asn Arg Val Asp Ile Leu Lys Arg Met Val Leu
160                 165                 170                 175

TTT TGC AAA GCA GCG ATT GAG GTT CCT TGG CAT GTT CCA TGT GGT GGG         574
Phe Cys Lys Ala Ala Ile Glu Val Pro Trp His Val Pro Cys Gly Gly
                    180                 185                 190

GTC TGC TAT GGA GAT GGA AAT TTA GTG TTC ATT GCT AAT GAT TGG CAT         622
Val Cys Tyr Gly Asp Gly Asn Leu Val Phe Ile Ala Asn Asp Trp His
                195                 200                 205

ACT GCT TTA TTG CCA GTA TAT CTG AAA GCT TAT TAT CGT GAC AAT GGA         670
Thr Ala Leu Leu Pro Val Tyr Leu Lys Ala Tyr Tyr Arg Asp Asn Gly
            210                 215                 220

ATT ATG AAC TAT ACA AGA TCT GTC CTG GTG ATT CAT AAC ATC GCT CAT         718
Ile Met Asn Tyr Thr Arg Ser Val Leu Val Ile His Asn Ile Ala His
        225                 230                 235

CAG GGT CGT GGT CCT TTG GAG GAT TTT TCA TAT GTA GAT CTT CCA CCA         766
Gln Gly Arg Gly Pro Leu Glu Asp Phe Ser Tyr Val Asp Leu Pro Pro
240                 245                 250                 255

CAC TAT ATG GAC CCT TTC AAG TTG TAT GAC CCA GTA GGA GGT GAG CAT         814
His Tyr Met Asp Pro Phe Lys Leu Tyr Asp Pro Val Gly Gly Glu His
                    260                 265                 270

TTC AAC ATT TTT GCG GCT GGT CTA AAG ACA GCA GAT CGT GTA GTT ACA         862
Phe Asn Ile Phe Ala Ala Gly Leu Lys Thr Ala Asp Arg Val Val Thr
                275                 280                 285

GTT AGT CAT GGA TAT TCA TGG GAA CTA AAG ACT TCC CAA GGT GGT TGG         910
Val Ser His Gly Tyr Ser Trp Glu Leu Lys Thr Ser Gln Gly Gly Trp
            290                 295                 300

GGA TTG CAT CAG ATA ATT AAT GAG AAC GAT TGG AAA TTA CAG GGT ATT         958
Gly Leu His Gln Ile Ile Asn Glu Asn Asp Trp Lys Leu Gln Gly Ile
        305                 310                 315

GTG AAT GGG ATT GAT ACA AAA GAG TGG AAC CCT GAG TTG GAC GTT CAC        1006
Val Asn Gly Ile Asp Thr Lys Glu Trp Asn Pro Glu Leu Asp Val His
320                 325                 330                 335

TTA CAG TCA GAT GGT TAC ATG AAC TAC TCC TTG GAC ACG CTA CAG ACT        1054
Leu Gln Ser Asp Gly Tyr Met Asn Tyr Ser Leu Asp Thr Leu Gln Thr
                    340                 345                 350

GGC AAG CCT CAA TGT AAA GCT GCA TTG CAG AAG GAA CTT GGT TTA CCA        1102
Gly Lys Pro Gln Cys Lys Ala Ala Leu Gln Lys Glu Leu Gly Leu Pro
                355                 360                 365
```

| | | | | | | | | | | | | | | |
|---|---|---|---|---|---|---|---|---|---|---|---|---|---|---|
| GTT | CGT | GAT | GAT | GTC | CCA | CTG | ATC | GGT | TTC | ATT | GGG | AGG | CTT | GAC | CCA | 1150 |
| Val | Arg | Asp | Asp | Val | Pro | Leu | Ile | Gly | Phe | Ile | Gly | Arg | Leu | Asp | Pro |
| | | 370 | | | | 375 | | | | 380 | | | | | |
| CAA | AAG | GGT | GTT | GAT | CTG | ATT | GCT | GAG | GCC | AGT | GCT | TGG | ATG | ATG | GGT | 1198 |
| Gln | Lys | Gly | Val | Asp | Leu | Ile | Ala | Glu | Ala | Ser | Ala | Trp | Met | Met | Gly |
| 385 | | | | | 390 | | | | | 395 | | | | | |
| CAG | GAT | GTA | CAA | CTG | GTC | ATG | TTG | GGG | ACG | GGG | AGG | CGT | GAC | CTT | GAA | 1246 |
| Gln | Asp | Val | Gln | Leu | Val | Met | Leu | Gly | Thr | Gly | Arg | Arg | Asp | Leu | Glu |
| 400 | | | | | 405 | | | | | 410 | | | | | 415 |
| CAG | ATG | CTA | AGG | CAA | TTT | GAG | TGT | CAA | CAC | AAT | GAT | AAA | ATT | AGA | GGA | 1294 |
| Gln | Met | Leu | Arg | Gln | Phe | Glu | Cys | Gln | His | Asn | Asp | Lys | Ile | Arg | Gly |
| | | | 420 | | | | | 425 | | | | | 430 | | |
| TGG | GTT | GGT | TTC | TCT | GTG | AAG | ACT | TCT | CAT | CGT | ATA | ACT | GCT | GGT | GCA | 1342 |
| Trp | Val | Gly | Phe | Ser | Val | Lys | Thr | Ser | His | Arg | Ile | Thr | Ala | Gly | Ala |
| | | | 435 | | | | | 440 | | | | | 445 | | |
| GAC | ATT | CTG | CTC | ATG | CCT | TCT | AGA | TTT | GAG | GCC | TTG | CGA | CTG | AAC | CAG | 1390 |
| Asp | Ile | Leu | Leu | Met | Pro | Ser | Arg | Phe | Glu | Ala | Leu | Arg | Leu | Asn | Gln |
| | | | 450 | | | | | 455 | | | | | 460 | | |
| CTT | TAT | GCA | ATG | AAA | TAT | GGG | ACT | ATT | CCT | GTT | GTT | CAT | GCA | GTA | GGA | 1438 |
| Leu | Tyr | Ala | Met | Lys | Tyr | Gly | Thr | Ile | Pro | Val | Val | His | Ala | Val | Gly |
| | | 465 | | | | | 470 | | | | | 475 | | | |
| GGA | CTC | AGA | GAT | ACT | GTG | CAG | CCC | TTT | GAT | CCT | TTT | AAT | GAG | TCA | GGA | 1486 |
| Gly | Leu | Arg | Asp | Thr | Val | Gln | Pro | Phe | Asp | Pro | Phe | Asn | Glu | Ser | Gly |
| 480 | | | | | 485 | | | | | 490 | | | | | 495 |
| CTG | GGG | TGG | ACC | TTC | AGT | AGG | GCT | GAA | GCT | AGC | CAG | CTG | ATC | CAC | GCA | 1534 |
| Leu | Gly | Trp | Thr | Phe | Ser | Arg | Ala | Glu | Ala | Ser | Gln | Leu | Ile | His | Ala |
| | | | 500 | | | | | 505 | | | | | 510 | | |
| TTA | GGA | AAT | TGC | TTA | CTG | ACT | TAT | CGT | GAG | TAC | AAA | AAG | AGT | TGG | GAG | 1582 |
| Leu | Gly | Asn | Cys | Leu | Leu | Thr | Tyr | Arg | Glu | Tyr | Lys | Lys | Ser | Trp | Glu |
| | | 515 | | | | | 520 | | | | | 525 | | | |
| GGG | ATT | CAG | ACA | CGT | TGT | ATG | ACA | CAA | GAC | TTA | AGT | TGG | GAT | AAT | GCT | 1630 |
| Gly | Ile | Gln | Thr | Arg | Cys | Met | Thr | Gln | Asp | Leu | Ser | Trp | Asp | Asn | Ala |
| | 530 | | | | | 535 | | | | | 540 | | | | |
| GCT | CAG | AAC | TAT | GAA | GAA | GTT | CTC | ATC | GCT | GCT | AAG | TAT | CAG | TGG | | 1675 |
| Ala | Gln | Asn | Tyr | Glu | Glu | Val | Leu | Ile | Ala | Ala | Lys | Tyr | Gln | Trp |
| 545 | | | | | 550 | | | | | 555 | | | | | |

| | |
|---|---|
| TGAGGTTCAT TACTTGTAGA TATTTGGGGA TTTTGGCCAT TGTATCAAGT TCTAATGA | 1735 |
| GGATTTCAGA GACATGTTTC TGGTATCGAC ACGAGAGGAT GCATGCAACA AGTTGGCT | 1795 |
| CTATCATACT ACTACCACGT CAGGAATGAT TGCCGCACTT GATCATGTAA TCATGTAT | 1855 |
| ACTCTATTTT GTTTGCAAAA TGTAGTTACA TGTTGCAATT CTAAAAAAA AAAAAAA | 1915 |
| AAAAAAAAA A | 1926 |

(2) INFORMATION FOR SEQ ID NO: 6:

(i) SEQUENCE CHARACTERISTICS:
        (A) LENGTH: 558 amino acids
        (B) TYPE: amino acid
        (D) TOPOLOGY: linear (ii) MOLECULE TYPE: protein (xi) SEQUENCE DESCRIPTION: SEQ ID NO: 6:

| | | | | | | | | | | | | | | |
|---|---|---|---|---|---|---|---|---|---|---|---|---|---|---|
| Gly | Thr | Ser | Lys | Ser | Leu | Val | Asp | Val | Pro | Gly | Lys | Lys | Ile | Gln | Ser |
| 1 | | | | 5 | | | | | 10 | | | | | 15 | |

| | | | | | | | | | | | | | | |
|---|---|---|---|---|---|---|---|---|---|---|---|---|---|---|
| Tyr | Met | Pro | Ser | Leu | Arg | Lys | Glu | Ser | Ser | Ala | Ser | His | Val | Glu | Gln |
| | | | 20 | | | | | 25 | | | | | 30 | | |

| | | | | | | | | | | | | | | |
|---|---|---|---|---|---|---|---|---|---|---|---|---|---|---|
| Arg | Asn | Glu | Asn | Leu | Glu | Gly | Ser | Ser | Ala | Glu | Ala | Asn | Glu | Glu | Thr |
| | | 35 | | | | | 40 | | | | | 45 | | | |

-continued

```
Glu Asp Pro Val Asn Ile Asp Glu Lys Pro Pro Leu Ala Gly Thr
 50                  55                  60

Asn Val Met Asn Ile Ile Leu Val Ala Ser Glu Cys Ala Pro Trp Ser
 65                  70                  75                  80

Lys Thr Gly Gly Leu Gly Asp Val Ala Gly Ala Leu Pro Lys Ala Leu
                 85                  90                  95

Ala Arg Arg Gly His Arg Val Met Val Val Ala Pro Arg Tyr Asp Asn
            100                 105                 110

Tyr Pro Glu Pro Gln Asp Ser Gly Val Arg Lys Ile Tyr Lys Val Asp
        115                 120                 125

Gly Gln Asp Val Glu Val Thr Tyr Phe Gln Ala Phe Ile Asp Gly Val
    130                 135                 140

Asp Phe Val Phe Ile Asp Ser His Met Phe Arg His Ile Gly Asn Asn
145                 150                 155                 160

Ile Tyr Gly Gly Asn Arg Val Asp Ile Leu Lys Arg Met Val Leu Phe
                165                 170                 175

Cys Lys Ala Ala Ile Glu Val Pro Trp His Val Pro Cys Gly Gly Val
            180                 185                 190

Cys Tyr Gly Asp Gly Asn Leu Val Phe Ile Ala Asn Asp Trp His Thr
        195                 200                 205

Ala Leu Leu Pro Val Tyr Leu Lys Ala Tyr Tyr Arg Asp Asn Gly Ile
    210                 215                 220

Met Asn Tyr Thr Arg Ser Val Leu Val Ile His Asn Ile Ala His Gln
225                 230                 235                 240

Gly Arg Gly Pro Leu Glu Asp Phe Ser Tyr Val Asp Leu Pro Pro His
                245                 250                 255

Tyr Met Asp Pro Phe Lys Leu Tyr Asp Pro Val Gly Gly Glu His Phe
            260                 265                 270

Asn Ile Phe Ala Ala Gly Leu Lys Thr Ala Asp Arg Val Val Thr Val
        275                 280                 285

Ser His Gly Tyr Ser Trp Glu Leu Lys Thr Ser Gln Gly Gly Trp Gly
    290                 295                 300

Leu His Gln Ile Ile Asn Glu Asn Asp Trp Lys Leu Gln Gly Ile Val
305                 310                 315                 320

Asn Gly Ile Asp Thr Lys Glu Trp Asn Pro Glu Leu Asp Val His Leu
                325                 330                 335

Gln Ser Asp Gly Tyr Met Asn Tyr Ser Leu Asp Thr Leu Gln Thr Gly
            340                 345                 350

Lys Pro Gln Cys Lys Ala Ala Leu Gln Lys Glu Leu Gly Leu Pro Val
        355                 360                 365

Arg Asp Asp Val Pro Leu Ile Gly Phe Ile Gly Arg Leu Asp Pro Gln
    370                 375                 380

Lys Gly Val Asp Leu Ile Ala Glu Ala Ser Ala Trp Met Met Gly Gln
385                 390                 395                 400

Asp Val Gln Leu Val Met Leu Gly Thr Gly Arg Arg Asp Leu Glu Gln
                405                 410                 415

Met Leu Arg Gln Phe Glu Cys Gln His Asn Asp Lys Ile Arg Gly Trp
            420                 425                 430

Val Gly Phe Ser Val Lys Thr Ser His Arg Ile Thr Ala Gly Ala Asp
        435                 440                 445

Ile Leu Leu Met Pro Ser Arg Phe Glu Ala Leu Arg Leu Asn Gln Leu
    450                 455                 460
```

```
Tyr Ala Met Lys Tyr Gly Thr Ile Pro Val Val His Ala Val Gly Gly
465                 470                 475                 480

Leu Arg Asp Thr Val Gln Pro Phe Asp Pro Phe Asn Glu Ser Gly Leu
                485                 490                 495

Gly Trp Thr Phe Ser Arg Ala Glu Ala Ser Gln Leu Ile His Ala Leu
                500                 505                 510

Gly Asn Cys Leu Leu Thr Tyr Arg Glu Tyr Lys Lys Ser Trp Glu Gly
                515                 520                 525

Ile Gln Thr Arg Cys Met Thr Gln Asp Leu Ser Trp Asp Asn Ala Ala
                530                 535                 540

Gln Asn Tyr Glu Glu Val Leu Ile Ala Ala Lys Tyr Gln Trp
545                 550                 555
```

(2) INFORMATION FOR SEQ ID NO: 7:

(i) SEQUENCE CHARACTERISTICS:
        (A) LENGTH: 2793 base pairs
        (B) TYPE: nucleotide
        (C) STRANDEDNESS: single
        (D) TOPOLOGY: linear (ii) MOLECULE TYPE: cDNA to mRNA (vi) ORIGINAL SOURCE:
        (A) ORGANISM: Solanum tuberosum
        (B) STRAIN: cv D,sir,e
        (F) TISSUE TYPE: leaf tissue (vii) IMMEDIATE SOURCE:
        (A) LIBRARY: cDNA-library in Lambda ZAPII
        (D) OTHER INFORMATION: CDS (ix) FEATURE:
        (B) LOCATION:242..2542

(xi) SEQUENCE DESCRIPTION: SEQ ID NO: 7:

```
CCGCCCATTT TTCACCAAAC GTTTTTGACA TTGACCTCCA TTGTCGTTAC TTCTTGGTTT      60

CTCTTTCAAT ATTGCTTCAC AATCCCTAAT TCTCTGTACT AGTCTCTATC TCAATTGGGT     120

TTTCTTTACT TGTCAATTAT CTCTACTGGG TCGGCTTCTA TTTCCACTAG GTCACTCTGG     180

TTCTTGAAAT CTTGGATTCC TATTATCCCT GTGAACTTCA TCTTTTGTGA TTTCTACTGT     240

A ATG GAG AAT TCC ATT CTT CTT CAT AGT GGA AAT CAG TTC CAC CCC         286
  Met Glu Asn Ser Ile Leu Leu His Ser Gly Asn Gln Phe His Pro
  1               5                  10                  15

AAC TTA CCC CTT TTA GCA CTT AGG CCC AAA AAA TTA TCT CTA ATT CAT       334
Asn Leu Pro Leu Leu Ala Leu Arg Pro Lys Lys Leu Ser Leu Ile His
                20                  25                  30

GGC TCC AGT AGA GAG CAA ATG TGG AGG ATC AAG CGC GTT AAA GCA ACA       382
Gly Ser Ser Arg Glu Gln Met Trp Arg Ile Lys Arg Val Lys Ala Thr
            35                  40                  45

GGT GAA AAT TCT GGG GAA GCT GCA AGT GCT GAT GAA TCG AAT GAT GCC       430
Gly Glu Asn Ser Gly Glu Ala Ala Ser Ala Asp Glu Ser Asn Asp Ala
        50                  55                  60

TTA CAG GTT ACA ATT GAA AAG AGC AAA AAG GTT TTA GCC ATG CAA CAG       478
Leu Gln Val Thr Ile Glu Lys Ser Lys Lys Val Leu Ala Met Gln Gln
65                  70                  75

GAC CTA CTT CAA CAG ATT GCA GAA AGA AGA AAA GTA GTC TCT TCA ATA       526
Asp Leu Leu Gln Gln Ile Ala Glu Arg Arg Lys Val Val Ser Ser Ile
    80                  85                  90                  95

AAA AGC AGT CTT GCC AAT GCC AAA GGT ACT TAT GAT GGT GGG AGT GGT       574
Lys Ser Ser Leu Ala Asn Ala Lys Gly Thr Tyr Asp Gly Gly Ser Gly
                100                 105                 110
```

```
AGC TTA TCA GAT GTT GAT ATC CCT GAC GTG GAT AAA GAT TAT AAT GTT         622
Ser Leu Ser Asp Val Asp Ile Pro Asp Val Asp Lys Asp Tyr Asn Val
        115                 120                 125

ACT GTA CCT AGT ACT GCT GCT ACT CCA ATT ACT GAT GTC GAT AAA AAT         670
Thr Val Pro Ser Thr Ala Ala Thr Pro Ile Thr Asp Val Asp Lys Asn
            130                 135                 140

ACA CCG CCT GCT ATA AGC CAA GAT TTT GTT GAA AGT AAA AGA GAA ATC         718
Thr Pro Pro Ala Ile Ser Gln Asp Phe Val Glu Ser Lys Arg Glu Ile
    145                 150                 155

AAA AGG GAC CTG GCC GAT GAA AGG GCA CCC CCA CTG TCG AGA TCA TCT         766
Lys Arg Asp Leu Ala Asp Glu Arg Ala Pro Pro Leu Ser Arg Ser Ser
160                 165                 170                 175

ATC ACA GCC AGT AGC CAG ATT TCC TCT ACT GTA AGT TCC AAA AGA ACG         814
Ile Thr Ala Ser Ser Gln Ile Ser Ser Thr Val Ser Ser Lys Arg Thr
        180                 185                 190

TTG AAT GTC CCT CCA GAA ACT CCG AAG TCC AGT CAA GAG ACA CTT TTG         862
Leu Asn Val Pro Pro Glu Thr Pro Lys Ser Ser Gln Glu Thr Leu Leu
            195                 200                 205

GAT GTG AAT TCA CGC AAA AGT TTA GTA GAT GTT CCT GGA AAG AAG ATC         910
Asp Val Asn Ser Arg Lys Ser Leu Val Asp Val Pro Gly Lys Lys Ile
    210                 215                 220

CAG TCT TAT ATG CCT TCA TTA CGT AAA GAA TCC TCA GCA TCC CAT GTG         958
Gln Ser Tyr Met Pro Ser Leu Arg Lys Glu Ser Ser Ala Ser His Val
225                 230                 235

GAA CAG AGG AAT GAA AAT CTT GAA GGA TCA AGT GCT GAG GCA AAC GAA        1006
Glu Gln Arg Asn Glu Asn Leu Glu Gly Ser Ser Ala Glu Ala Asn Glu
240                 245                 250                 255

GAG ACT GAA GAT CCT GTG AAT ATA GAT GAG AAA CCC CCT CCA TTG GCA        1054
Glu Thr Glu Asp Pro Val Asn Ile Asp Glu Lys Pro Pro Pro Leu Ala
        260                 265                 270

GGA ACA AAT GTT ATG AAC ATT ATT TTG GTG GCT TCA GAA TGC GCT CCA        1102
Gly Thr Asn Val Met Asn Ile Ile Leu Val Ala Ser Glu Cys Ala Pro
            275                 280                 285

TGG TCT AAA ACA GGT GGG CTT GGA GAT GTT GCT GGA GCA TTA CCC AAA        1150
Trp Ser Lys Thr Gly Gly Leu Gly Asp Val Ala Gly Ala Leu Pro Lys
    290                 295                 300

GCT TTG GCT CGA CGT GGC CAC AGA GTT ATG GTT GTG GCA CCT CGT TAT        1198
Ala Leu Ala Arg Arg Gly His Arg Val Met Val Val Ala Pro Arg Tyr
305                 310                 315

GAC AAC TAT CCT GAA CCT CAA GAT TCT GGT GTA AGA AAA ATT TAT AAA        1246
Asp Asn Tyr Pro Glu Pro Gln Asp Ser Gly Val Arg Lys Ile Tyr Lys
320                 325                 330                 335

GTT GAT GGT CAG GAT GTG GAA GTG ACT TAC TTC CAA GCT TTT ATT GAT        1294
Val Asp Gly Gln Asp Val Glu Val Thr Tyr Phe Gln Ala Phe Ile Asp
        340                 345                 350

GGT GTG GAT TTT GTT TTC ATT GAC AGT CAT ATG TTT AGA CAC ATT GGG        1342
Gly Val Asp Phe Val Phe Ile Asp Ser His Met Phe Arg His Ile Gly
            355                 360                 365

AAC AAC ATT TAC GGA GGG AAC CGT GTG GAT ATT TTA AAA CGC ATG GTT        1390
Asn Asn Ile Tyr Gly Gly Asn Arg Val Asp Ile Leu Lys Arg Met Val
    370                 375                 380

TTA TTT TGC AAA GCA GCG ATT GAG GTT CCT TGG CAT GTT CCA TGT GGT        1438
Leu Phe Cys Lys Ala Ala Ile Glu Val Pro Trp His Val Pro Cys Gly
385                 390                 395

GGG GTC TGC TAT GGA GAT GGA AAT TTA GTG TTC ATT GCT AAT GAT TGG        1486
Gly Val Cys Tyr Gly Asp Gly Asn Leu Val Phe Ile Ala Asn Asp Trp
400                 405                 410                 415

CAT ACT GCT TTA TTG CCA GTA TAT CTG AAA GCT TAT TAT CGT GAC AAT        1534
His Thr Ala Leu Leu Pro Val Tyr Leu Lys Ala Tyr Tyr Arg Asp Asn
        420                 425                 430
```

```
GGA ATT ATG AAC TAT ACA AGA TCT GTC CTG GTG ATT CAT AAC ATC GCT        1582
Gly Ile Met Asn Tyr Thr Arg Ser Val Leu Val Ile His Asn Ile Ala
            435                 440                 445

CAT CAG GGT CGT GGT CCT TTG GAG GAT TTT TCA TAT GTA GAT CTT CCA        1630
His Gln Gly Arg Gly Pro Leu Glu Asp Phe Ser Tyr Val Asp Leu Pro
        450                 455                 460

CCA CAC TAT ATG GAC CCT TTC AAG TTG TAT GAC CCA GTA GGA GGT GAG        1678
Pro His Tyr Met Asp Pro Phe Lys Leu Tyr Asp Pro Val Gly Gly Glu
465                 470                 475

CAT TTC AAC ATT TTT GCG GCT GGT CTA AAG ACA GCA GAT CGT GTA GTT        1726
His Phe Asn Ile Phe Ala Ala Gly Leu Lys Thr Ala Asp Arg Val Val
480                 485                 490                 495

ACA GTT AGT CAT GGA TAT TCA TGG GAA CTA AAG ACT TCC CAA GGT GGT        1774
Thr Val Ser His Gly Tyr Ser Trp Glu Leu Lys Thr Ser Gln Gly Gly
                500                 505                 510

TGG GGA TTG CAT CAG ATA ATT AAT GAG AAC GAT TGG AAA TTA CAG GGT        1822
Trp Gly Leu His Gln Ile Ile Asn Glu Asn Asp Trp Lys Leu Gln Gly
            515                 520                 525

ATT GTG AAT GGG ATT GAT ACA AAA GAG TGG AAC CCT GAG TTG GAC GTT        1870
Ile Val Asn Gly Ile Asp Thr Lys Glu Trp Asn Pro Glu Leu Asp Val
        530                 535                 540

CAC TTA CAG TCA GAT GGT TAC ATG AAC TAC TCC TTG GAC ACG CTA CAG        1918
His Leu Gln Ser Asp Gly Tyr Met Asn Tyr Ser Leu Asp Thr Leu Gln
545                 550                 555

ACT GGC AAG CCT CAA TGT AAA GCT GCA TTG CAG AAG GAA CTT GGT TTA        1966
Thr Gly Lys Pro Gln Cys Lys Ala Ala Leu Gln Lys Glu Leu Gly Leu
560                 565                 570                 575

CCA GTT CGT GAT GAT GTC CCA CTG ATC GGT TTC ATT GGG AGG CTT GAC        2014
Pro Val Arg Asp Asp Val Pro Leu Ile Gly Phe Ile Gly Arg Leu Asp
                580                 585                 590

CCA CAA AAG GGT GTT GAT CTG ATT GCT GAG GCC AGT GCT TGG ATG ATG        2062
Pro Gln Lys Gly Val Asp Leu Ile Ala Glu Ala Ser Ala Trp Met Met
            595                 600                 605

GGT CAG GAT GTA CAA CTG GTC ATG TTG GGG ACG GGG AGG CGT GAC CTT        2110
Gly Gln Asp Val Gln Leu Val Met Leu Gly Thr Gly Arg Arg Asp Leu
        610                 615                 620

GAA CAG ATG CTA AGG CAA TTT GAG TGT CAA CAC AAT GAT AAA ATT AGA        2158
Glu Gln Met Leu Arg Gln Phe Glu Cys Gln His Asn Asp Lys Ile Arg
625                 630                 635

GGA TGG GTT GGT TTC TCT GTG AAG ACT TCT CAT CGT ATA ACT GCT GGT        2206
Gly Trp Val Gly Phe Ser Val Lys Thr Ser His Arg Ile Thr Ala Gly
640                 645                 650                 655

GCA GAC ATT CTG CTC ATG CCT TCT AGA TTT GAG CCT TGC GGA CTG AAC        2254
Ala Asp Ile Leu Leu Met Pro Ser Arg Phe Glu Pro Cys Gly Leu Asn
                660                 665                 670

CAG CTT TAT GCA ATG AAA TAT GGG ACT ATT CCT GTT GTT CAT GCA GTA        2302
Gln Leu Tyr Ala Met Lys Tyr Gly Thr Ile Pro Val Val His Ala Val
            675                 680                 685

GGA GGA CTC AGA GAT ACT GTG CAG CCC TTT GAT CCT TTT AAT GAG TCA        2350
Gly Gly Leu Arg Asp Thr Val Gln Pro Phe Asp Pro Phe Asn Glu Ser
        690                 695                 700

GGA CTG GGG TGG ACC TTC AGT AGG GCT GAA GCT AGC CAG CTG ATC CAC        2398
Gly Leu Gly Trp Thr Phe Ser Arg Ala Glu Ala Ser Gln Leu Ile His
705                 710                 715

GCA TTA GGA AAT TGC TTA CTG ACT TAT CGT GAG TAC AAA AAG AGT TGG        2446
Ala Leu Gly Asn Cys Leu Leu Thr Tyr Arg Glu Tyr Lys Lys Ser Trp
720                 725                 730                 735

GAG GGG ATT CAG ACA CGT TGT ATG ACA CAA GAC TTA AGT TGG GAT AAT        2494
Glu Gly Ile Gln Thr Arg Cys Met Thr Gln Asp Leu Ser Trp Asp Asn
                740                 745                 750
```

```
GCT GCT CAG AAC TAT GAA GAA GTT CTC ATC GCT GCT AAG TAT CAG TGG    2542
Ala Ala Gln Asn Tyr Glu Glu Val Leu Ile Ala Ala Lys Tyr Gln Trp
            755                 760                 765

TGAGGTTCAT TACTTGTAGA TATTTGGGGA TTTTGGCCAT TGTATCAAGT TCTAATGATG   2602

GGATTTCAGA GACATGTTTC TGGTATCGAC ACGAGAGGAT GCATGCAACA AGTTGGCTAA   2662

CTATCATACT ACTACCACGT CAGGAATGAT TGCCGCACTT GATCATGTAA TCATGTATAT   2722

ACTCTATTTT GTTTGCAAAA TGTAGTTACA TGTTGCAATT TCTAAAAAAA AAAAAAAAA    2782

AAAAAAAAA A                                                        2793

(2) INFORMATION FOR SEQ ID NO: 8:

(i) SEQUENCE CHARACTERISTICS:
        (A) LENGTH: 767 amino acids
        (B) TYPE: amino acid
        (D) TOPOLOGY: linear (ii) MOLECULE TYPE: protein (xi) SEQUENCE DESCRIPTION: SEQ ID NO: 8:

Met Glu Asn Ser Ile Leu Leu His Ser Gly Asn Gln Phe His Pro Asn
 1               5                  10                  15

Leu Pro Leu Leu Ala Leu Arg Pro Lys Lys Leu Ser Leu Ile His Gly
            20                  25                  30

Ser Ser Arg Glu Gln Met Trp Arg Ile Lys Arg Val Lys Ala Thr Gly
        35                  40                  45

Glu Asn Ser Gly Glu Ala Ala Ser Ala Asp Glu Ser Asn Asp Ala Leu
    50                  55                  60

Gln Val Thr Ile Glu Lys Ser Lys Val Leu Ala Met Gln Gln Asp
65                  70                  75                  80

Leu Leu Gln Gln Ile Ala Glu Arg Arg Lys Val Val Ser Ser Ile Lys
                85                  90                  95

Ser Ser Leu Ala Asn Ala Lys Gly Thr Tyr Asp Gly Gly Ser Gly Ser
            100                 105                 110

Leu Ser Asp Val Asp Ile Pro Asp Val Asp Lys Asp Tyr Asn Val Thr
        115                 120                 125

Val Pro Ser Thr Ala Ala Thr Pro Ile Thr Asp Val Asp Lys Asn Thr
130                 135                 140

Pro Pro Ala Ile Ser Gln Asp Phe Val Glu Ser Lys Arg Glu Ile Lys
145                 150                 155                 160

Arg Asp Leu Ala Asp Glu Arg Ala Pro Pro Leu Ser Arg Ser Ile
                165                 170                 175

Thr Ala Ser Ser Gln Ile Ser Ser Thr Val Ser Ser Lys Arg Thr Leu
            180                 185                 190

Asn Val Pro Pro Glu Thr Pro Lys Ser Ser Gln Glu Thr Leu Leu Asp
        195                 200                 205

Val Asn Ser Arg Lys Ser Leu Val Asp Val Pro Gly Lys Lys Ile Gln
    210                 215                 220

Ser Tyr Met Pro Ser Leu Arg Lys Glu Ser Ala Ser His Val Glu
225                 230                 235                 240

Gln Arg Asn Glu Asn Leu Glu Gly Ser Ser Ala Glu Ala Asn Glu Glu
                245                 250                 255

Thr Glu Asp Pro Val Asn Ile Asp Glu Lys Pro Pro Leu Ala Gly
            260                 265                 270

Thr Asn Val Met Asn Ile Ile Leu Val Ala Ser Glu Cys Ala Pro Trp
        275                 280                 285
```

-continued

```
Ser Lys Thr Gly Gly Leu Gly Asp Val Ala Gly Ala Leu Pro Lys Ala
290                 295                 300

Leu Ala Arg Arg Gly His Arg Val Met Val Val Ala Pro Arg Tyr Asp
305                 310                 315                 320

Asn Tyr Pro Glu Pro Gln Asp Ser Gly Val Arg Lys Ile Tyr Lys Val
                325                 330                 335

Asp Gly Gln Asp Val Glu Val Thr Tyr Phe Gln Ala Phe Ile Asp Gly
                340                 345                 350

Val Asp Phe Val Phe Ile Asp Ser His Met Phe Arg His Ile Gly Asn
            355                 360                 365

Asn Ile Tyr Gly Gly Asn Arg Val Asp Ile Leu Lys Arg Met Val Leu
        370                 375                 380

Phe Cys Lys Ala Ala Ile Glu Val Pro Trp His Val Pro Cys Gly Gly
385                 390                 395                 400

Val Cys Tyr Gly Asp Gly Asn Leu Val Phe Ile Ala Asn Asp Trp His
                405                 410                 415

Thr Ala Leu Leu Pro Val Tyr Leu Lys Ala Tyr Tyr Arg Asp Asn Gly
                420                 425                 430

Ile Met Asn Tyr Thr Arg Ser Val Leu Val Ile His Asn Ile Ala His
            435                 440                 445

Gln Gly Arg Gly Pro Leu Glu Asp Phe Ser Tyr Val Asp Leu Pro Pro
450                 455                 460

His Tyr Met Asp Pro Phe Lys Leu Tyr Asp Pro Val Gly Gly Glu His
465                 470                 475                 480

Phe Asn Ile Phe Ala Ala Gly Leu Lys Thr Ala Asp Arg Val Val Thr
                485                 490                 495

Val Ser His Gly Tyr Ser Trp Glu Leu Lys Thr Ser Gln Gly Gly Trp
                500                 505                 510

Gly Leu His Gln Ile Ile Asn Glu Asn Asp Trp Lys Leu Gln Gly Ile
            515                 520                 525

Val Asn Gly Ile Asp Thr Lys Glu Trp Asn Pro Glu Leu Asp Val His
530                 535                 540

Leu Gln Ser Asp Gly Tyr Met Asn Tyr Ser Leu Asp Thr Leu Gln Thr
545                 550                 555                 560

Gly Lys Pro Gln Cys Lys Ala Ala Leu Gln Lys Glu Leu Gly Leu Pro
                565                 570                 575

Val Arg Asp Asp Val Pro Leu Ile Gly Phe Ile Gly Arg Leu Asp Pro
                580                 585                 590

Gln Lys Gly Val Asp Leu Ile Ala Glu Ala Ser Ala Trp Met Met Gly
            595                 600                 605

Gln Asp Val Gln Leu Val Met Leu Gly Thr Gly Arg Arg Asp Leu Glu
610                 615                 620

Gln Met Leu Arg Gln Phe Glu Cys Gln His Asn Asp Lys Ile Arg Gly
625                 630                 635                 640

Trp Val Gly Phe Ser Val Lys Thr Ser His Arg Ile Thr Ala Gly Ala
                645                 650                 655

Asp Ile Leu Leu Met Pro Ser Arg Phe Glu Pro Cys Gly Leu Asn Gln
                660                 665                 670

Leu Tyr Ala Met Lys Tyr Gly Thr Ile Pro Val Val His Ala Val Gly
            675                 680                 685

Gly Leu Arg Asp Thr Val Gln Pro Phe Asp Pro Phe Asn Glu Ser Gly
690                 695                 700
```

```
Leu Gly Trp Thr Phe Ser Arg Ala Glu Ala Ser Gln Leu Ile His Ala
705                 710                 715                 720

Leu Gly Asn Cys Leu Leu Thr Tyr Arg Glu Tyr Lys Lys Ser Trp Glu
                725                 730                 735

Gly Ile Gln Thr Arg Cys Met Thr Gln Asp Leu Ser Trp Asp Asn Ala
                740                 745                 750

Ala Gln Asn Tyr Glu Glu Val Leu Ile Ala Ala Lys Tyr Gln Trp
            755                 760                 765

(2) INFORMATION FOR SEQ ID NO: 9:

(i) SEQUENCE CHARACTERISTICS:
        (A) LENGTH: 2360 base pairs
        (B) TYPE: nucleotide
        (C) STRANDEDNESS: single
        (D) TOPOLOGY: linear (ii) MOLECULE TYPE: cDNA (vi) ORIGINAL SOURCE:
        (A) ORGANISM: Solanum tuberosum
        (B) STRAIN: cv. D,sir,e
        (F) TISSUE TYPE: leaf tissue (vii) IMMEDIATE SOURCE:
        (A) LIBRARY: cDNA-library in Lambda ZAPII
        (D) OTHER INFORMATION: CDS (ix) FEATURE:
        (B) LOCATION:68..1990

(xi) SEQUENCE DESCRIPTION: SEQ ID NO: 9:

AGATTTTCTA TATTGAAAGA TTTTGTCTTT ACATGATTCT TGATTTTACA GCAGGTGTCA      60

ATACCAA ATG GGG TCT CTG CAA ACA CCC ACA AAT CTT AGC AAT AAG TCA      109
        Met Gly Ser Leu Gln Thr Pro Thr Asn Leu Ser Asn Lys Ser
        1               5                   10

TGT TTA TGT GTG TCA GGG AGA GTT GTG AAG GGT TTG AGG GTA GAA AGA      157
Cys Leu Cys Val Ser Gly Arg Val Val Lys Gly Leu Arg Val Glu Arg
15              20                  25                  30

CAA GTG GGG TTG GGG TTT TCT TGG TTG TTG AAG GGA CGA AGA AAC AGA      205
Gln Val Gly Leu Gly Phe Ser Trp Leu Leu Lys Gly Arg Arg Asn Arg
                35                  40                  45

AAA GTT CAA TCT TTG TGT GTT ACA AGT AGT GTT TCA GAT GGT TCA TCA      253
Lys Val Gln Ser Leu Cys Val Thr Ser Ser Val Ser Asp Gly Ser Ser
            50                  55                  60

ATT GCT GAA AAT AAG AAT GTG TCA GAA GGG CTT CTT TTG GGT GCT GAG      301
Ile Ala Glu Asn Lys Asn Val Ser Glu Gly Leu Leu Leu Gly Ala Glu
        65                  70                  75

AGA GAT GGT TCT GGC TCT GTT GTT GGT TTT CAA TTG ATT CCA CAT TCT      349
Arg Asp Gly Ser Gly Ser Val Val Gly Phe Gln Leu Ile Pro His Ser
80                  85                  90

GTT GCA GGA GAT GCA ACA ATG GTA GAA TCT CAT GAT ATT GTA GCC AAT      397
Val Ala Gly Asp Ala Thr Met Val Glu Ser His Asp Ile Val Ala Asn
95                  100                 105                 110

GAT AGA GAT GAC TTG AGT GAG GAT ACT GAG GAG ATG GAG GAA ACC CCA      445
Asp Arg Asp Asp Leu Ser Glu Asp Thr Glu Glu Met Glu Glu Thr Pro
            115                 120                 125

ATC AAA TTA ACT TTC AAT ATC ATT TTT GTT ACT GCT GAA GCA GCT CCA      493
Ile Lys Leu Thr Phe Asn Ile Ile Phe Val Thr Ala Glu Ala Ala Pro
        130                 135                 140

TAT TCT AAG ACT GGT GGA TTA GGA GAT GTT TGT GGT TCT TTG CCA ATG      541
Tyr Ser Lys Thr Gly Gly Leu Gly Asp Val Cys Gly Ser Leu Pro Met
    145                 150                 155
```

```
GCA CTA GCT GCT CGG GGT CAT CGT GTA ATG GTC GTT TCA CCT AGG TAT        589
Ala Leu Ala Ala Arg Gly His Arg Val Met Val Val Ser Pro Arg Tyr
    160                 165                 170

TTG AAT GGA GGT CCT TCA GAT GAA AAG TAC GCC AAT GCT GTT GAC CTT        637
Leu Asn Gly Gly Pro Ser Asp Glu Lys Tyr Ala Asn Ala Val Asp Leu
175                 180                 185                 190

GAT GTG CGG GCC ACT GTC CAT TGC TTT GGT GAT GCA CAG GAA GTA GCC        685
Asp Val Arg Ala Thr Val His Cys Phe Gly Asp Ala Gln Glu Val Ala
                195                 200                 205

TTC TAC CAT GAA TAC AGG GCA GGT GTT GAT TGG GTA TTT GTG GAC CAC        733
Phe Tyr His Glu Tyr Arg Ala Gly Val Asp Trp Val Phe Val Asp His
        210                 215                 220

TCT TCT TAC TGC AGA CCT GGA ACG CCA TAT GGT GAT ATT TAT GGT GCA        781
Ser Ser Tyr Cys Arg Pro Gly Thr Pro Tyr Gly Asp Ile Tyr Gly Ala
            225                 230                 235

TTT GGT GAT AAT CAG TTT CGC TTC ACT TTG CTT TCT CAC GCA GCA TGT        829
Phe Gly Asp Asn Gln Phe Arg Phe Thr Leu Leu Ser His Ala Ala Cys
                240                 245                 250

GAA GCG CCA TTG GTT CTT CCA CTG GGA GGG TTC ACT TAT GGA GAG AAG        877
Glu Ala Pro Leu Val Leu Pro Leu Gly Gly Phe Thr Tyr Gly Glu Lys
255                 260                 265                 270

TGC TTG TTT CTC GCT AAT GAT TGG CAT GCT GCC CTG GTT CCT TTA CTT        925
Cys Leu Phe Leu Ala Asn Asp Trp His Ala Ala Leu Val Pro Leu Leu
                275                 280                 285

TTA GCG GCC AAG TAT CGT CCT TAT GGT GTT TAC AAG GAT GCT CGT AGT        973
Leu Ala Ala Lys Tyr Arg Pro Tyr Gly Val Tyr Lys Asp Ala Arg Ser
            290                 295                 300

ATT GTC GCA ATA CAC AAC ATT GCA CAT CAG GGA GTG GAG CCT GCA GTA       1021
Ile Val Ala Ile His Asn Ile Ala His Gln Gly Val Glu Pro Ala Val
                305                 310                 315

ACC TAC AAT AAT TTG GGT TTG CCT CCA CAA TGG TAT GGA GCA GTT GAA       1069
Thr Tyr Asn Asn Leu Gly Leu Pro Pro Gln Trp Tyr Gly Ala Val Glu
320                 325                 330

TGG ATA TTT CCC ACA TGG GCA AGG GCG CAT GCG CTT GAC ACT GGT GAA       1117
Trp Ile Phe Pro Thr Trp Ala Arg Ala His Ala Leu Asp Thr Gly Glu
335                 340                 345                 350

ACA GTG AAC GTT TTG AAA GGG GCA ATA GCA GTT GCT GAT CGG ATA CTG       1165
Thr Val Asn Val Leu Lys Gly Ala Ile Ala Val Ala Asp Arg Ile Leu
                355                 360                 365

ACA GTT AGC CAG GGA TAC TCA TGG GAA ATA ACA ACT CCT GAA GGG GGA       1213
Thr Val Ser Gln Gly Tyr Ser Trp Glu Ile Thr Thr Pro Glu Gly Gly
            370                 375                 380

TAT GGG CTA CAT GAG CTG TTG AGC AGT AGA CAG TCT GTT CTT AAT GGA       1261
Tyr Gly Leu His Glu Leu Leu Ser Ser Arg Gln Ser Val Leu Asn Gly
                385                 390                 395

ATT ACT AAT GGA ATA GAT GTT AAT GAT TGG AAC CCG TCG ACA GAT GAG       1309
Ile Thr Asn Gly Ile Asp Val Asn Asp Trp Asn Pro Ser Thr Asp Glu
400                 405                 410

CAT ATT GCT TCG CAT TAC TCC ATC AAT GAC CTC TCC GGA AAG GTT CAG       1357
His Ile Ala Ser His Tyr Ser Ile Asn Asp Leu Ser Gly Lys Val Gln
415                 420                 425                 430

TGC AAG ACT GAT CTG CAA AAG GAA CTG GGC CTT CCA ATT CGA CCT GAT       1405
Cys Lys Thr Asp Leu Gln Lys Glu Leu Gly Leu Pro Ile Arg Pro Asp
                435                 440                 445

TGT CCT CTG ATT GGA TTT ATT GGA AGG CTG GAC TAC CAG AAA GGT GTT       1453
Cys Pro Leu Ile Gly Phe Ile Gly Arg Leu Asp Tyr Gln Lys Gly Val
            450                 455                 460

GAC ATA ATC CTG TCA GCA ATT CCA GAA CTT ATG CAG AAT GAT GTC CAA       1501
Asp Ile Ile Leu Ser Ala Ile Pro Glu Leu Met Gln Asn Asp Val Gln
                465                 470                 475
```

```
GTT GTA ATG CTT GGA TCT GGT GAG AAA CAA TAT GAA GAC TGG ATG AGA    1549
Val Val Met Leu Gly Ser Gly Glu Lys Gln Tyr Glu Asp Trp Met Arg
    480                 485                 490

CAT ACA GAA AAT CTT TTT AAA GAC AAA TTT CGT GCT TGG GTT GGA TTT    1597
His Thr Glu Asn Leu Phe Lys Asp Lys Phe Arg Ala Trp Val Gly Phe
495                 500                 505                 510

AAT GTT CCA GTT TCT CAT AGG ATA ACA GCA GGA TGC GAC ATA CTA TTG    1645
Asn Val Pro Val Ser His Arg Ile Thr Ala Gly Cys Asp Ile Leu Leu
                    515                 520                 525

ATG CCC TCA AGA TTC GAA CCG TGT GGC TTA AAC CAA TTG TAT GCA ATG    1693
Met Pro Ser Arg Phe Glu Pro Cys Gly Leu Asn Gln Leu Tyr Ala Met
            530                 535                 540

AGA TAT GGC ACC ATA CCT ATT GTT CAT AGC ACG GGG GGC CTA AGA GAC    1741
Arg Tyr Gly Thr Ile Pro Ile Val His Ser Thr Gly Gly Leu Arg Asp
        545                 550                 555

ACA GTG AAG GAT TTT AAT CCA TAT GCT CAA GAA GGA ATA GGT GAA GGT    1789
Thr Val Lys Asp Phe Asn Pro Tyr Ala Gln Glu Gly Ile Gly Glu Gly
    560                 565                 570

ACC GGG TGG ACA TTT TCT CCT CTA ACG AGT GAA AAG TTG CTT GAT ACA    1837
Thr Gly Trp Thr Phe Ser Pro Leu Thr Ser Glu Lys Leu Leu Asp Thr
575                 580                 585                 590

CTG AAG CTG GCA ATC GGG ACT TAT ACA GAA CAT AAG TCA TCT TGG GAG    1885
Leu Lys Leu Ala Ile Gly Thr Tyr Thr Glu His Lys Ser Ser Trp Glu
                    595                 600                 605

GGA TTG ATG AGG AGA GGT ATG GGA AGG GAC TAT TCC TGG GAA AAT GCA    1933
Gly Leu Met Arg Arg Gly Met Gly Arg Asp Tyr Ser Trp Glu Asn Ala
            610                 615                 620

GCC ATT CAA TAT GAA CAA GTT TTC ACC TGG GCC TTT ATA GAT CCT CCA    1981
Ala Ile Gln Tyr Glu Gln Val Phe Thr Trp Ala Phe Ile Asp Pro Pro
        625                 630                 635

TAT GTC AGA TGATTTATCA AGAAAGATTG CAAACGGGAT ACATCATTAA            2030
Tyr Val Arg
    640

ACTATACGCG GAGCTTTTGG TGCTATTAGC TACTGTCATT GGGCGCGGAA TGTTTGTG    2090

TCTTTCTGAT TCAGAGAGAT CAAGTTAGTT CCAAAGACAT ACGTAGCCTG TCCCTGTC    2150

TGAGGGAGTA AAACTACAAA AGGCAATTAG AAACCACCAA GAACTGGCTC CTTTGGGA    2210

AGAGTGGAAA TATGTAAAAA AGAATTTTGA GTTTAATGTC AATTGATTAA TTGTTCTC    2270

TTTTAAAAAA AACATCTCAT CTCATACAAT ATATAAAATT GATCATGATT GATGAAAA    2330

AAAAAAAAAA AAAAAAAAA AAAAAAAAA                                    2360

(2) INFORMATION FOR SEQ ID NO: 10:

(i) SEQUENCE CHARACTERISTICS:
        (A) LENGTH: 641 amino acids
        (B) TYPE: amino acid
        (D) TOPOLOGY: linear (ii) MOLECULE TYPE: protein (xi) SEQUENCE DESCRIPTION: SEQ ID NO: 10:

Met Gly Ser Leu Gln Thr Pro Thr Asn Leu Ser Asn Lys Ser Cys Leu
1               5                   10                  15

Cys Val Ser Gly Arg Val Val Lys Gly Leu Arg Val Glu Arg Gln Val
            20                  25                  30

Gly Leu Gly Phe Ser Trp Leu Leu Lys Gly Arg Arg Asn Arg Lys Val
        35                  40                  45

Gln Ser Leu Cys Val Thr Ser Ser Val Ser Asp Gly Ser Ser Ile Ala
    50                  55                  60
```

-continued

```
Glu Asn Lys Asn Val Ser Glu Gly Leu Leu Leu Gly Ala Glu Arg Asp
 65                  70                  75                  80

Gly Ser Gly Ser Val Val Gly Phe Gln Leu Ile Pro His Ser Val Ala
                 85                  90                  95

Gly Asp Ala Thr Met Val Glu Ser His Asp Ile Val Ala Asn Asp Arg
                100                 105                 110

Asp Asp Leu Ser Glu Asp Thr Glu Glu Met Glu Thr Pro Ile Lys
            115                 120                 125

Leu Thr Phe Asn Ile Ile Phe Val Thr Ala Glu Ala Pro Tyr Ser
130                 135                 140

Lys Thr Gly Gly Leu Gly Asp Val Cys Gly Ser Leu Pro Met Ala Leu
145                 150                 155                 160

Ala Ala Arg Gly His Arg Val Met Val Val Ser Pro Arg Tyr Leu Asn
                165                 170                 175

Gly Gly Pro Ser Asp Glu Lys Tyr Ala Asn Ala Val Asp Leu Asp Val
                180                 185                 190

Arg Ala Thr Val His Cys Phe Gly Asp Ala Gln Glu Val Ala Phe Tyr
                195                 200                 205

His Glu Tyr Arg Ala Gly Val Asp Trp Val Phe Val Asp His Ser Ser
            210                 215                 220

Tyr Cys Arg Pro Gly Thr Pro Tyr Gly Asp Ile Tyr Gly Ala Phe Gly
225                 230                 235                 240

Asp Asn Gln Phe Arg Phe Thr Leu Leu Ser His Ala Ala Cys Glu Ala
                245                 250                 255

Pro Leu Val Leu Pro Leu Gly Gly Phe Thr Tyr Gly Glu Lys Cys Leu
                260                 265                 270

Phe Leu Ala Asn Asp Trp His Ala Ala Leu Val Pro Leu Leu Leu Ala
            275                 280                 285

Ala Lys Tyr Arg Pro Tyr Gly Val Tyr Lys Asp Ala Arg Ser Ile Val
            290                 295                 300

Ala Ile His Asn Ile Ala His Gln Gly Val Glu Pro Ala Val Thr Tyr
305                 310                 315                 320

Asn Asn Leu Gly Leu Pro Pro Gln Trp Tyr Gly Ala Val Glu Trp Ile
                325                 330                 335

Phe Pro Thr Trp Ala Arg Ala His Ala Leu Asp Thr Gly Glu Thr Val
            340                 345                 350

Asn Val Leu Lys Gly Ala Ile Ala Val Ala Asp Arg Ile Leu Thr Val
            355                 360                 365

Ser Gln Gly Tyr Ser Trp Glu Ile Thr Thr Pro Glu Gly Gly Tyr Gly
            370                 375                 380

Leu His Glu Leu Leu Ser Ser Arg Gln Ser Val Leu Asn Gly Ile Thr
385                 390                 395                 400

Asn Gly Ile Asp Val Asn Asp Trp Asn Pro Ser Thr Asp Glu His Ile
                405                 410                 415

Ala Ser His Tyr Ser Ile Asn Asp Leu Ser Gly Lys Val Gln Cys Lys
                420                 425                 430

Thr Asp Leu Gln Lys Glu Leu Gly Leu Pro Ile Arg Pro Asp Cys Pro
            435                 440                 445

Leu Ile Gly Phe Ile Gly Arg Leu Asp Tyr Gln Lys Gly Val Asp Ile
450                 455                 460

Ile Leu Ser Ala Ile Pro Glu Leu Met Gln Asn Asp Val Gln Val Val
465                 470                 475                 480
```

-continued

```
Met Leu Gly Ser Gly Glu Lys Gln Tyr Glu Asp Trp Met Arg His Thr
                485                 490                 495

Glu Asn Leu Phe Lys Asp Lys Phe Arg Ala Trp Val Gly Phe Asn Val
                500                 505                 510

Pro Val Ser His Arg Ile Thr Ala Gly Cys Asp Ile Leu Leu Met Pro
                515                 520                 525

Ser Arg Phe Glu Pro Cys Gly Leu Asn Gln Leu Tyr Ala Met Arg Tyr
        530                 535                 540

Gly Thr Ile Pro Ile Val His Ser Thr Gly Gly Leu Arg Asp Thr Val
545                 550                 555                 560

Lys Asp Phe Asn Pro Tyr Ala Gln Glu Gly Ile Gly Glu Gly Thr Gly
                565                 570                 575

Trp Thr Phe Ser Pro Leu Thr Ser Glu Lys Leu Leu Asp Thr Leu Lys
                580                 585                 590

Leu Ala Ile Gly Thr Tyr Thr Glu His Lys Ser Ser Trp Glu Gly Leu
            595                 600                 605

Met Arg Arg Gly Met Gly Arg Asp Tyr Ser Trp Glu Asn Ala Ala Ile
            610                 615                 620

Gln Tyr Glu Gln Val Phe Thr Trp Ala Phe Ile Asp Pro Pro Tyr Val
625                 630                 635                 640

Arg
```

(2) INFORMATION FOR SEQ ID NO: 11:

(i) SEQUENCE CHARACTERISTICS:
        (A) LENGTH: 4168 base pairs
        (B) TYPE: nucleotide
        (C) STRANDEDNESS: single
        (D) TOPOLOGY: linear (ii) MOLECULE TYPE: cDNA to RNA (vi) ORIGINAL SOURCE:
        (A) ORGANISM: Solanum tuberosum
        (B) STRAIN: cv. D,sir,e
        (F) TISSUE TYPE: leaf tissue (vii) IMMEDIATE SOURCE:
        (A) LIBRARY: cDNA-library in Lambda ZAPII
        (D) OTHER INFORMATION: CDS (ix) FEATURE:
        (B) LOCATION:307..3897

(xi) SEQUENCE DESCRIPTION: SEQ ID NO: 11:

```
TTTTTTAATA GATTTTTAAA ACCCCATTAA AGCAAATACG TATATAATTG CAGCACAGAT      60

ACAGAGAGGG AGAGAGAAAG ATAGTGTGTT GATGAAGGAG AAGAGAGATA TTTCACATGG     120

GATGTTCTAT TTGATTCTGT GGTGAACAAG AGTTTTACAA AGAACATTCC TTTTTCTTTT    180

TTTCTTGGTT CTTGTGTGGG TCAGCCATGG ATGTTCCATT TCCACTGCAT AGACCATTGA    240

GTTGCACAAG TGTCTCCAAT GCAATAACCC ACCTCAAGAT CAAACCTTTT CTTGGGTTTG    300

TCTCTC ATG GAA CCA CAA GTC TAT CAG TAC AAT CTT CTT CAT GGA GGA       348
       Met Glu Pro Gln Val Tyr Gln Tyr Asn Leu Leu His Gly Gly
         1               5                  10

AGG ATG GAA ATG GTT ACT GGG GTT TCA TTT CCA TTT TGT GCA AAT CTC      396
Arg Met Glu Met Val Thr Gly Val Ser Phe Pro Phe Cys Ala Asn Leu
 15              20                  25                  30

TCG GGA AGA AGA CGG AGA AAA GTT TCA ACT ACT AGG AGT CAA GGA TCT      444
Ser Gly Arg Arg Arg Arg Lys Val Ser Thr Thr Arg Ser Gln Gly Ser
             35                  40                  45
```

```
TCA CCT AAG GGG TTT GTG CCA AGG AAG CCC TCA GGG ATG AGC ACG CAA      492
Ser Pro Lys Gly Phe Val Pro Arg Lys Pro Ser Gly Met Ser Thr Gln
         50                  55                  60

AGA AAG GTT CAG AAG AGC AAT GGT GAT AAA GAA AGT CAA AGT ACT TCA      540
Arg Lys Val Gln Lys Ser Asn Gly Asp Lys Glu Ser Gln Ser Thr Ser
             65                  70                  75

ACA TCT AAA GAA TCT GAA ATT TCC AAC CAG AAG ACG GTT GAA GCA AGA      588
Thr Ser Lys Glu Ser Glu Ile Ser Asn Gln Lys Thr Val Glu Ala Arg
 80                  85                  90

GTT GAA ACT AGT GAC GAT GAC ACT AAA GTA GTG GTG AGG GAC CAC AAG      636
Val Glu Thr Ser Asp Asp Asp Thr Lys Val Val Val Arg Asp His Lys
     95                 100                 105                 110

TTT CTG GAG GAT GAG GAT GAA ATC AAT GGT TCT ACT AAA TCA ATA AGT      684
Phe Leu Glu Asp Glu Asp Glu Ile Asn Gly Ser Thr Lys Ser Ile Ser
                    115                 120                 125

ATG TCA CCT GTT CGT GTA TCA TCT CAA TTT GTT GAA AGT GAA GAA ACT      732
Met Ser Pro Val Arg Val Ser Ser Gln Phe Val Glu Ser Glu Glu Thr
                130                 135                 140

GGT GGT GAT GAC AAG GAT GCT GTA AAG TTA AAC AAA TCA AAG AGA TCG      780
Gly Gly Asp Asp Lys Asp Ala Val Lys Leu Asn Lys Ser Lys Arg Ser
            145                 150                 155

GAA GAG AGT GAT TTT CTA ATT GAT TCT GTA ATA AGA GAA CAA AGT GGA      828
Glu Glu Ser Asp Phe Leu Ile Asp Ser Val Ile Arg Glu Gln Ser Gly
160                 165                 170

TCT CAG GGG GAA ACT AAT GCC AGT AGC AAG GGA AGC CAT GCT GTG GGT      876
Ser Gln Gly Glu Thr Asn Ala Ser Ser Lys Gly Ser His Ala Val Gly
175                 180                 185                 190

ACA AAA CTT TAT GAG ATA TTG CAG GTG GAT GTT GAG CCA CAA CAA TTG      924
Thr Lys Leu Tyr Glu Ile Leu Gln Val Asp Val Glu Pro Gln Gln Leu
                195                 200                 205

AAA GAA AAT AAT GCT GGG AAT GTT GAA TAC AAA GGA CCT GTA GCA AGT      972
Lys Glu Asn Asn Ala Gly Asn Val Glu Tyr Lys Gly Pro Val Ala Ser
                210                 215                 220

AAG CTA TTG GAA ATT ACT AAG GCT AGT GAT GTG GAA CAC ACT GAA AGC     1020
Lys Leu Leu Glu Ile Thr Lys Ala Ser Asp Val Glu His Thr Glu Ser
            225                 230                 235

AAT GAG ATT GAT GAC TTA GAC ACT AAT AGT TTC TTT AAA TCA GAT TTA     1068
Asn Glu Ile Asp Asp Leu Asp Thr Asn Ser Phe Phe Lys Ser Asp Leu
240                 245                 250

ATT GAA GAG GAT GAG CCA TTA GCT GCA GGA ACA GTG GAG ACT GGA GAT     1116
Ile Glu Glu Asp Glu Pro Leu Ala Ala Gly Thr Val Glu Thr Gly Asp
255                 260                 265                 270

TCT TCT CTA AAC TTA AGA TTG GAG ATG GAA GCA AAT CTA CGT AGG CAG     1164
Ser Ser Leu Asn Leu Arg Leu Glu Met Glu Ala Asn Leu Arg Arg Gln
                275                 280                 285

GCT ATA GAA AGG CTT GCC GAG GAA AAT TTA TTG CAA GGG ATC AGA TTA     1212
Ala Ile Glu Arg Leu Ala Glu Glu Asn Leu Leu Gln Gly Ile Arg Leu
            290                 295                 300

TTT TGT TTT CCA GAG GTT GTA AAA CCT GAT GAA GAT GTC GAG ATA TTT     1260
Phe Cys Phe Pro Glu Val Val Lys Pro Asp Glu Asp Val Glu Ile Phe
            305                 310                 315

CTT AAC AGA GGT CTT TCC ACT TTG AAG AAT GAG TCT GAT GTC TTG ATT     1308
Leu Asn Arg Gly Leu Ser Thr Leu Lys Asn Glu Ser Asp Val Leu Ile
            320                 325                 330

ATG GGA GCT TTT AAT GAG TGG CGC TAT AGG TCT TTT ACT ACA AGG CTA     1356
Met Gly Ala Phe Asn Glu Trp Arg Tyr Arg Ser Phe Thr Thr Arg Leu
335                 340                 345                 350

ACT GAG ACT CAT CTC AAT GGA GAT TGG TGG TCT TGC AAG ATC CAT GTT     1404
Thr Glu Thr His Leu Asn Gly Asp Trp Trp Ser Cys Lys Ile His Val
                355                 360                 365
```

```
CCC AAG GAA GCA TAC AGG GCT GAT TTT GTG TTT TTT AAT GGA CAA GAT    1452
Pro Lys Glu Ala Tyr Arg Ala Asp Phe Val Phe Phe Asn Gly Gln Asp
            370                 375                 380

GTC TAT GAC AAC AAT GAT GGA AAT GAC TTC AGT ATA ACT GTG AAA GGT    1500
Val Tyr Asp Asn Asn Asp Gly Asn Asp Phe Ser Ile Thr Val Lys Gly
            385                 390                 395

GGT ATG CAA ATC ATT GAC TTT GAA AAT TTC TTG CTT GAG GAG AAA TGG    1548
Gly Met Gln Ile Ile Asp Phe Glu Asn Phe Leu Leu Glu Glu Lys Trp
        400                 405                 410

AGA GAA CAG GAG AAA CTT GCT AAA GAA CAA GCT GAA AGA GAA AGA CTA    1596
Arg Glu Gln Glu Lys Leu Ala Lys Glu Gln Ala Glu Arg Glu Arg Leu
415                 420                 425                 430

GCG GAA GAA CAA AGA CGA ATA GAA GCA GAG AAA GCT GAA ATT GAA GCT    1644
Ala Glu Glu Gln Arg Arg Ile Glu Ala Glu Lys Ala Glu Ile Glu Ala
                435                 440                 445

GAC AGA GCA CAA GCA AAG GAA GAG GCT GCA AAG AAA AAG AAA GTA TTG    1692
Asp Arg Ala Gln Ala Lys Glu Glu Ala Ala Lys Lys Lys Lys Val Leu
            450                 455                 460

CGA GAA TTG ATG GTA AAA GCC ACG AAG ACT CGT GAT ATC ACG TGG TAC    1740
Arg Glu Leu Met Val Lys Ala Thr Lys Thr Arg Asp Ile Thr Trp Tyr
            465                 470                 475

ATA GAG CCA AGT GAA TTT AAA TGC GAG GAC AAG GTC AGG TTA TAC TAT    1788
Ile Glu Pro Ser Glu Phe Lys Cys Glu Asp Lys Val Arg Leu Tyr Tyr
480                 485                 490

AAC AAA AGT TCA GGT CCT CTC TCC CAT GCT AAG GAC TTG TGG ATC CAC    1836
Asn Lys Ser Ser Gly Pro Leu Ser His Ala Lys Asp Leu Trp Ile His
495                 500                 505                 510

GGA GGA TAT AAT AAT TGG AAG GAT GGT TTG TCT ATT GTC AAA AAG CTT    1884
Gly Gly Tyr Asn Asn Trp Lys Asp Gly Leu Ser Ile Val Lys Lys Leu
                515                 520                 525

GTT AAA TCT GAG AGA ATA GAT GGT GAT TGG TGG TAT ACA GAG GTT GTT    1932
Val Lys Ser Glu Arg Ile Asp Gly Asp Trp Trp Tyr Thr Glu Val Val
            530                 535                 540

ATT CCT GAT CAG GCA CTT TTC TTG GAT TGG GTT TTT GCT GAT GGT CCA    1980
Ile Pro Asp Gln Ala Leu Phe Leu Asp Trp Val Phe Ala Asp Gly Pro
            545                 550                 555

CCC AAG CAT GCC ATT GCT TAT GAT AAC AAT CAC CGC CAA GAC TTC CAT    2028
Pro Lys His Ala Ile Ala Tyr Asp Asn Asn His Arg Gln Asp Phe His
            560                 565                 570

GCC ATT GTC CCC AAC CAC ATT CCG GAG GAA TTA TAT TGG GTT GAG GAA    2076
Ala Ile Val Pro Asn His Ile Pro Glu Glu Leu Tyr Trp Val Glu Glu
575                 580                 585                 590

GAA CAT CAG ATC TTT AAG ACA CTT CAG GAG GAG AGA AGG CTT AGA GAA    2124
Glu His Gln Ile Phe Lys Thr Leu Gln Glu Glu Arg Arg Leu Arg Glu
                595                 600                 605

GCG GCT ATG CGT GCT AAG GTT GAA AAA ACA GCA CTT CTG AAA ACT GAA    2172
Ala Ala Met Arg Ala Lys Val Glu Lys Thr Ala Leu Leu Lys Thr Glu
            610                 615                 620

ACA AAG GAA AGA ACT ATG AAA TCA TTT TTA CTG TCT CAG AAG CAT GTA    2220
Thr Lys Glu Arg Thr Met Lys Ser Phe Leu Leu Ser Gln Lys His Val
            625                 630                 635

GTA TAT ACT GAG CCT CTT GAT ATC CAA GCT GGA AGC AGC GTC ACA GTT    2268
Val Tyr Thr Glu Pro Leu Asp Ile Gln Ala Gly Ser Ser Val Thr Val
            640                 645                 650

TAC TAT AAT CCC GCC AAT ACA GTA CTT AAT GGT AAA CCT GAA ATT TGG    2316
Tyr Tyr Asn Pro Ala Asn Thr Val Leu Asn Gly Lys Pro Glu Ile Trp
655                 660                 665                 670

TTC AGA TGT TCA TTT AAT CGC TGG ACT CAC CGC CTG GGT CCA TTG CCA    2364
Phe Arg Cys Ser Phe Asn Arg Trp Thr His Arg Leu Gly Pro Leu Pro
                675                 680                 685
```

| | |
|---|---|
| CCT CAG AAA ATG TCG CCT GCT GAA AAT GGC ACC CAT GTC AGA GCA ACT<br>Pro Gln Lys Met Ser Pro Ala Glu Asn Gly Thr His Val Arg Ala Thr<br>          690                      695                      700 | 2412 |
| GTG AAG GTT CCA TTG GAT GCA TAT ATG ATG GAT TTT GTA TTT TCC GAG<br>Val Lys Val Pro Leu Asp Ala Tyr Met Met Asp Phe Val Phe Ser Glu<br>          705                      710                      715 | 2460 |
| AGA GAA GAT GGT GGG ATT TTT GAC AAT AAG AGC GGA ATG GAC TAT CAC<br>Arg Glu Asp Gly Gly Ile Phe Asp Asn Lys Ser Gly Met Asp Tyr His<br>720                      725                      730 | 2508 |
| ATA CCT GTG TTT GGA GGA GTC GCT AAA GAA CCT CCA ATG CAT ATT GTC<br>Ile Pro Val Phe Gly Gly Val Ala Lys Glu Pro Pro Met His Ile Val<br>735                      740                      745                      750 | 2556 |
| CAT ATT GCT GTC GAA ATG GCA CCA ATT GCA AAG GTG GGA GGC CTT GGT<br>His Ile Ala Val Glu Met Ala Pro Ile Ala Lys Val Gly Gly Leu Gly<br>          755                      760                      765 | 2604 |
| GAT GTT GTT ACT AGT CTT TCC CGT GCT GTT CAA GAT TTA AAC CAT AAT<br>Asp Val Val Thr Ser Leu Ser Arg Ala Val Gln Asp Leu Asn His Asn<br>          770                      775                      780 | 2652 |
| GTG GAT ATT ATC TTA CCT AAG TAT GAC TGT TTG AAG ATG AAT AAT GTG<br>Val Asp Ile Ile Leu Pro Lys Tyr Asp Cys Leu Lys Met Asn Asn Val<br>                 785                      790                      795 | 2700 |
| AAG GAC TTT CGG TTT CAC AAA AAC TAC TTT TGG GGT GGG ACT GAA ATA<br>Lys Asp Phe Arg Phe His Lys Asn Tyr Phe Trp Gly Gly Thr Glu Ile<br>800                      805                      810 | 2748 |
| AAA GTA TGG TTT GGA AAG GTG GAA GGT CTC TCG GTC TAT TTT TTG GAG<br>Lys Val Trp Phe Gly Lys Val Glu Gly Leu Ser Val Tyr Phe Leu Glu<br>815                      820                      825                      830 | 2796 |
| CCT CAA AAC GGG TTA TTT TCG AAA GGG TGC GTC TAT GGT TGT AGC AAT<br>Pro Gln Asn Gly Leu Phe Ser Lys Gly Cys Val Tyr Gly Cys Ser Asn<br>                 835                      840                      845 | 2844 |
| GAT GGT GAA CGA TTT GGT TTC TTC TGT CAC GCG GCT TTG GAG TTT CTT<br>Asp Gly Glu Arg Phe Gly Phe Phe Cys His Ala Ala Leu Glu Phe Leu<br>          850                      855                      860 | 2892 |
| CTG CAA GGT GGA TTT AGT CCG GAT ATC ATT CAT TGC CAT GAT TGG TCT<br>Leu Gln Gly Gly Phe Ser Pro Asp Ile Ile His Cys His Asp Trp Ser<br>          865                      870                      875 | 2940 |
| AGT GCT CCT GTT GCT TGG CTC TTT AAG GAA CAA TAT ACA CAC TAT GGT<br>Ser Ala Pro Val Ala Trp Leu Phe Lys Glu Gln Tyr Thr His Tyr Gly<br>880                      885                      890 | 2988 |
| CTA AGC AAA TCT CGT ATA GTC TTC ACG ATA CAT AAT CTT GAA TTT GGG<br>Leu Ser Lys Ser Arg Ile Val Phe Thr Ile His Asn Leu Glu Phe Gly<br>895                      900                      905                      910 | 3036 |
| GCA GAT CTC ATT GGG AGA GCA ATG ACT AAC GCA GAC AAA GCT ACA ACA<br>Ala Asp Leu Ile Gly Arg Ala Met Thr Asn Ala Asp Lys Ala Thr Thr<br>                 915                      920                      925 | 3084 |
| GTT TCA CCA ACT TAC TCA CAG GAG GTG TCT GGA AAC CCT GTA ATT GCG<br>Val Ser Pro Thr Tyr Ser Gln Glu Val Ser Gly Asn Pro Val Ile Ala<br>          930                      935                      940 | 3132 |
| CCT CAC CTT CAC AAG TTC CAT GGT ATA GTG AAT GGG ATT GAC CCA GAT<br>Pro His Leu His Lys Phe His Gly Ile Val Asn Gly Ile Asp Pro Asp<br>          945                      950                      955 | 3180 |
| ATT TGG GAT CCT TTA AAC GAT AAG TTC ATT CCG ATT CCG TAC ACC TCA<br>Ile Trp Asp Pro Leu Asn Asp Lys Phe Ile Pro Ile Pro Tyr Thr Ser<br>960                      965                      970 | 3228 |
| GAA AAC GTT GTT GAA GGC AAA ACA GCA GCC AAG GAA GCT TTG CAG CGA<br>Glu Asn Val Val Glu Gly Lys Thr Ala Ala Lys Glu Ala Leu Gln Arg<br>975                      980                      985                      990 | 3276 |
| AAA CTT GGA CTG AAA CAG GCT GAC CTT CCT TTG GTA GGA ATT ATC ACC<br>Lys Leu Gly Leu Lys Gln Ala Asp Leu Pro Leu Val Gly Ile Ile Thr<br>                 995                      1000                    1005 | 3324 |

-continued

| | |
|---|---|
| CGC TTA ACT CAC CAG AAA GGA ATC CAC CTC ATT AAA CAT GCT ATT TGG<br>Arg Leu Thr His Gln Lys Gly Ile His Leu Ile Lys His Ala Ile Trp<br>          1010                1015                1020 | 3372 |
| CGC ACC TTG GAA CGG AAC GGA CAG GTA GTC TTG CTT GGT TCT GCT CCT<br>Arg Thr Leu Glu Arg Asn Gly Gln Val Val Leu Leu Gly Ser Ala Pro<br>     1025                1030                1035 | 3420 |
| GAT CCT AGG GTA CAA AAC GAT TTT GTT AAT TTG GCA AAT CAA TTG CAC<br>Asp Pro Arg Val Gln Asn Asp Phe Val Asn Leu Ala Asn Gln Leu His<br>          1040                1045                1050 | 3468 |
| TCC AAA TAT AAT GAC CGC GCA CGA CTC TGT CTA ACA TAT GAC GAG CCA<br>Ser Lys Tyr Asn Asp Arg Ala Arg Leu Cys Leu Thr Tyr Asp Glu Pro<br>1055                1060                1065                1070 | 3516 |
| CTT TCT CAC CTG ATA TAT GCT GGT GCT GAT TTT ATT CTA GTT CCT TCA<br>Leu Ser His Leu Ile Tyr Ala Gly Ala Asp Phe Ile Leu Val Pro Ser<br>                1075                1080                1085 | 3564 |
| ATA TTT GAG CCA TGT GGA CTA ACA CAA CTT ACC GCT ATG AGA TAT GGT<br>Ile Phe Glu Pro Cys Gly Leu Thr Gln Leu Thr Ala Met Arg Tyr Gly<br>          1090                1095                1100 | 3612 |
| TCA ATT CCA GTC GTG CGT AAA ACT GGA GGA CTT TAT GAT ACT GTA TTT<br>Ser Ile Pro Val Val Arg Lys Thr Gly Gly Leu Tyr Asp Thr Val Phe<br>               1105                1110                1115 | 3660 |
| GAT GTT GAC CAT GAC AAA GAG AGA GCA CAA CAG TGT GGT CTT GAA CCA<br>Asp Val Asp His Asp Lys Glu Arg Ala Gln Gln Cys Gly Leu Glu Pro<br>          1120                1125                1130 | 3708 |
| AAT GGA TTC AGC TTT GAT GGA GCA GAT GCT GGC GGA GTT GAT TAT GCT<br>Asn Gly Phe Ser Phe Asp Gly Ala Asp Ala Gly Gly Val Asp Tyr Ala<br>1135                1140                1145                1150 | 3756 |
| CTG AAT AGA GCT CTC TCT GCT TGG TAC GAT GGT CGG GAT TGG TTC AAC<br>Leu Asn Arg Ala Leu Ser Ala Trp Tyr Asp Gly Arg Asp Trp Phe Asn<br>          1155                1160                1165 | 3804 |
| TCT TTA TGC AAG CAG GTC ATG GAA CAA GAT TGG TCT TGG AAC CGA CCT<br>Ser Leu Cys Lys Gln Val Met Glu Gln Asp Trp Ser Trp Asn Arg Pro<br>          1170                1175                1180 | 3852 |
| GCT CTT GAT TAT TTG GAG CTT TAC CAT GCT GCT AGA AAG TTA GAA<br>Ala Leu Asp Tyr Leu Glu Leu Tyr His Ala Ala Arg Lys Leu Glu<br>          1185                1190                1195 | 3897 |
| TAGTTAGTTT GTGAGATGCT AGCAGAAAAA TTCACGAGAT CTGCAATCTG TACAGGTTCA | 3957 |
| GTGTTTGCGT CTGGACAGCT TTTTTATTTC CTATATCAAA GTATAAATCA AGTCTACACT | 4017 |
| GAGATCAATA GCAGACAGTC CTCAGTTCAT TTCATTTTTT GTGCAACATA TGAAAGAGCT | 4077 |
| TAGCCTCTAA TAATGTAGTC ATTGATGATT ATTTGTTTTG GAAGAAATG AGAAATCAAA | 4137 |
| GGATGCAAAA TACTCTGAAA AAAAAAAAAA A | 4168 |

(2) INFORMATION FOR SEQ ID NO: 12:

(i) SEQUENCE CHARACTERISTICS:
        (A) LENGTH: 1197 amino acids
        (B) TYPE: amino acid
        (D) TOPOLOGY: linear (ii) MOLECULE TYPE: protein (xi) SEQUENCE DESCRIPTION: SEQ ID NO: 12:

Met Glu Pro Gln Val Tyr Gln Tyr Asn Leu Leu His Gly Gly Arg Met
1               5                  10                  15

Glu Met Val Thr Gly Val Ser Phe Pro Phe Cys Ala Asn Leu Ser Gly
            20                  25                  30

Arg Arg Arg Arg Lys Val Ser Thr Thr Arg Ser Gln Gly Ser Ser Pro
        35                  40                  45

```
Lys Gly Phe Val Pro Arg Lys Pro Ser Gly Met Ser Thr Gln Arg Lys
 50                  55                  60

Val Gln Lys Ser Asn Gly Asp Lys Glu Ser Gln Ser Thr Ser Thr Ser
 65                  70                  75                  80

Lys Glu Ser Glu Ile Ser Asn Gln Lys Thr Val Ala Arg Val Glu
                 85                  90                  95

Thr Ser Asp Asp Asp Thr Lys Val Val Arg Asp His Lys Phe Leu
            100                 105                 110

Glu Asp Glu Asp Glu Ile Asn Gly Ser Thr Lys Ser Ile Ser Met Ser
            115                 120                 125

Pro Val Arg Val Ser Ser Gln Phe Val Glu Ser Glu Thr Gly Gly
            130                 135                 140

Asp Asp Lys Asp Ala Val Lys Leu Asn Lys Ser Lys Arg Ser Glu Glu
145                 150                 155                 160

Ser Asp Phe Leu Ile Asp Ser Val Ile Arg Glu Gln Ser Gly Ser Gln
                165                 170                 175

Gly Glu Thr Asn Ala Ser Ser Lys Gly Ser His Ala Val Gly Thr Lys
            180                 185                 190

Leu Tyr Glu Ile Leu Gln Val Asp Val Glu Pro Gln Gln Leu Lys Glu
        195                 200                 205

Asn Asn Ala Gly Asn Val Glu Tyr Lys Gly Pro Val Ala Ser Lys Leu
        210                 215                 220

Leu Glu Ile Thr Lys Ala Ser Asp Val Glu His Thr Glu Ser Asn Glu
225                 230                 235                 240

Ile Asp Asp Leu Asp Thr Asn Ser Phe Phe Lys Ser Asp Leu Ile Glu
                245                 250                 255

Glu Asp Glu Pro Leu Ala Ala Gly Thr Val Glu Thr Gly Asp Ser Ser
            260                 265                 270

Leu Asn Leu Arg Leu Glu Met Glu Ala Asn Leu Arg Arg Gln Ala Ile
            275                 280                 285

Glu Arg Leu Ala Glu Glu Asn Leu Leu Gln Gly Ile Arg Leu Phe Cys
        290                 295                 300

Phe Pro Glu Val Val Lys Pro Asp Glu Asp Val Glu Ile Phe Leu Asn
305                 310                 315                 320

Arg Gly Leu Ser Thr Leu Lys Asn Glu Ser Asp Val Leu Ile Met Gly
                325                 330                 335

Ala Phe Asn Glu Trp Arg Tyr Arg Ser Phe Thr Thr Arg Leu Thr Glu
            340                 345                 350

Thr His Leu Asn Gly Asp Trp Trp Ser Cys Lys Ile His Val Pro Lys
        355                 360                 365

Glu Ala Tyr Arg Ala Asp Phe Val Phe Phe Asn Gly Gln Asp Val Tyr
        370                 375                 380

Asp Asn Asn Asp Gly Asn Asp Phe Ser Ile Thr Val Lys Gly Gly Met
385                 390                 395                 400

Gln Ile Ile Asp Phe Glu Asn Phe Leu Leu Glu Glu Lys Trp Arg Glu
                405                 410                 415

Gln Glu Lys Leu Ala Lys Glu Gln Ala Glu Arg Glu Arg Leu Ala Glu
            420                 425                 430

Glu Gln Arg Arg Ile Glu Ala Glu Lys Ala Glu Ile Glu Ala Asp Arg
        435                 440                 445

Ala Gln Ala Lys Glu Glu Ala Lys Lys Lys Val Leu Arg Glu
450                 455                 460
```

```
Leu Met Val Lys Ala Thr Lys Thr Arg Asp Ile Thr Trp Tyr Ile Glu
465                 470                 475                 480

Pro Ser Glu Phe Lys Cys Glu Asp Lys Val Arg Leu Tyr Tyr Asn Lys
                485                 490                 495

Ser Ser Gly Pro Leu Ser His Ala Lys Asp Leu Trp Ile His Gly Gly
                500                 505                 510

Tyr Asn Asn Trp Lys Asp Gly Leu Ser Ile Val Lys Lys Leu Val Lys
                515                 520                 525

Ser Glu Arg Ile Asp Gly Asp Trp Trp Tyr Thr Glu Val Val Ile Pro
530                 535                 540

Asp Gln Ala Leu Phe Leu Asp Trp Val Phe Ala Asp Gly Pro Pro Lys
545                 550                 555                 560

His Ala Ile Ala Tyr Asp Asn Asn His Arg Gln Asp Phe His Ala Ile
                565                 570                 575

Val Pro Asn His Ile Pro Glu Glu Leu Tyr Trp Val Glu Glu Glu His
                580                 585                 590

Gln Ile Phe Lys Thr Leu Gln Glu Arg Arg Leu Arg Glu Ala Ala
                595                 600                 605

Met Arg Ala Lys Val Glu Lys Thr Ala Leu Leu Lys Thr Glu Thr Lys
    610                 615                 620

Glu Arg Thr Met Lys Ser Phe Leu Leu Ser Gln Lys His Val Val Tyr
625                 630                 635                 640

Thr Glu Pro Leu Asp Ile Gln Ala Gly Ser Ser Val Thr Val Tyr Tyr
                645                 650                 655

Asn Pro Ala Asn Thr Val Leu Asn Gly Lys Pro Glu Ile Trp Phe Arg
                660                 665                 670

Cys Ser Phe Asn Arg Trp Thr His Arg Leu Gly Pro Leu Pro Pro Gln
    675                 680                 685

Lys Met Ser Pro Ala Glu Asn Gly Thr His Val Arg Ala Thr Val Lys
    690                 695                 700

Val Pro Leu Asp Ala Tyr Met Met Asp Phe Val Phe Ser Glu Arg Glu
705                 710                 715                 720

Asp Gly Gly Ile Phe Asp Asn Lys Ser Gly Met Asp Tyr His Ile Pro
                725                 730                 735

Val Phe Gly Gly Val Ala Lys Glu Pro Pro Met His Ile Val His Ile
                740                 745                 750

Ala Val Glu Met Ala Pro Ile Ala Lys Val Gly Gly Leu Gly Asp Val
                755                 760                 765

Val Thr Ser Leu Ser Arg Ala Val Gln Asp Leu Asn His Asn Val Asp
    770                 775                 780

Ile Ile Leu Pro Lys Tyr Asp Cys Leu Lys Met Asn Asn Val Lys Asp
785                 790                 795                 800

Phe Arg Phe His Lys Asn Tyr Phe Trp Gly Gly Thr Glu Ile Lys Val
                805                 810                 815

Trp Phe Gly Lys Val Glu Gly Leu Ser Val Tyr Phe Leu Glu Pro Gln
                820                 825                 830

Asn Gly Leu Phe Ser Lys Gly Cys Val Tyr Gly Cys Ser Asn Asp Gly
                835                 840                 845

Glu Arg Phe Gly Phe Phe Cys His Ala Ala Leu Glu Phe Leu Leu Gln
    850                 855                 860

Gly Gly Phe Ser Pro Asp Ile Ile His Cys His Asp Trp Ser Ser Ala
865                 870                 875                 880
```

```
Pro Val Ala Trp Leu Phe Lys Glu Gln Tyr Thr His Tyr Gly Leu Ser
            885                 890                 895
Lys Ser Arg Ile Val Phe Thr Ile His Asn Leu Glu Phe Gly Ala Asp
            900                 905                 910
Leu Ile Gly Arg Ala Met Thr Asn Ala Asp Lys Ala Thr Thr Val Ser
            915                 920                 925
Pro Thr Tyr Ser Gln Glu Val Ser Gly Asn Pro Val Ile Ala Pro His
            930                 935                 940
Leu His Lys Phe His Gly Ile Val Asn Gly Ile Asp Pro Asp Ile Trp
945                 950                 955                 960
Asp Pro Leu Asn Asp Lys Phe Ile Pro Ile Pro Tyr Thr Ser Glu Asn
            965                 970                 975
Val Val Glu Gly Lys Thr Ala Ala Lys Glu Ala Leu Gln Arg Lys Leu
            980                 985                 990
Gly Leu Lys Gln Ala Asp Leu Pro Leu Val Gly Ile Ile Thr Arg Leu
            995                 1000                1005
Thr His Gln Lys Gly Ile His Leu Ile Lys His Ala Ile Trp Arg Thr
            1010                1015                1020
Leu Glu Arg Asn Gly Gln Val Val Leu Gly Ser Ala Pro Asp Pro
1025                1030                1035                1040
Arg Val Gln Asn Asp Phe Val Asn Leu Ala Asn Gln Leu His Ser Lys
            1045                1050                1055
Tyr Asn Asp Arg Ala Arg Leu Cys Leu Thr Tyr Asp Glu Pro Leu Ser
            1060                1065                1070
His Leu Ile Tyr Ala Gly Ala Asp Phe Ile Leu Val Pro Ser Ile Phe
            1075                1080                1085
Glu Pro Cys Gly Leu Thr Gln Leu Thr Ala Met Arg Tyr Gly Ser Ile
            1090                1095                1100
Pro Val Val Arg Lys Thr Gly Gly Leu Tyr Asp Thr Val Phe Asp Val
1105                1110                1115                1120
Asp His Asp Lys Glu Arg Ala Gln Gln Cys Gly Leu Glu Pro Asn Gly
            1125                1130                1135
Phe Ser Phe Asp Gly Ala Asp Ala Gly Gly Val Asp Tyr Ala Leu Asn
            1140                1145                1150
Arg Ala Leu Ser Ala Trp Tyr Asp Gly Arg Asp Trp Phe Asn Ser Leu
            1155                1160                1165
Cys Lys Gln Val Met Glu Gln Asp Trp Ser Trp Asn Arg Pro Ala Leu
            1170                1175                1180
Asp Tyr Leu Glu Leu Tyr His Ala Ala Arg Lys Leu Glu
1185                1190                1195
```

(2) INFORMATION FOR SEQ ID NO: 13:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

```
Gly Thr Gly Gly Leu Arg Asp Thr Val Glu Asn Cys
1               5                   10
```

(2) INFORMATION FOR SEQ ID NO: 14:

(i) SEQUENCE CHARACTERISTICS:
        (A) LENGTH: 30 base pairs
        (B) TYPE: nucleotide
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 14:

ACAGGATCCT GTGCTATGCG GCGTGTGAAG        30

(2) INFORMATION FOR SEQ ID NO: 15:

(i) SEQUENCE CHARACTERISTICS:
        (A) LENGTH: 32 base pairs
        (B) TYPE: nucleotide
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 15:

TTGGGATCCG CAATGCCCAC AGCATTTTTT TC        32

(2) INFORMATION FOR SEQ ID NO: 16:

(i) SEQUENCE CHARACTERISTICS:
        (A) LENGTH: 12 amino acids
        (B) TYPE: amino acid
        (C) STRANDEDNESS: <Unknown>
        (D) TOPOLOGY: linear (ii) MOLECULE TYPE: Peptide (xi) SEQUENCE DESCRIPTION: SEQ ID NO: 16:

Pro Trp Ser Lys Thr Gly Gly Leu Gly Asp Val Cys
1         5                10

(2) INFORMATION FOR SEQ ID NO: 17:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: Peptide (xi) SEQUENCE DESCRIPTION: SEQ ID NO: 17:

Pro Ser Arg Phe Glu Pro Cys Gly Leu Asn Gln Leu Tyr
1         5                10